United States Patent
Saunier et al.

(10) Patent No.: US 6,635,091 B2
(45) Date of Patent: Oct. 21, 2003

(54) COMPOSITIONS FOR THE OXIDATION DYEING OF KERATINOUS FIBERS COMPRISING AT LEAST ONE COUPLER, AND DYEING METHODS

(75) Inventors: Jean-Baptiste Saunier, Paris (FR); Laurent Vidal, Paris (FR)

(73) Assignee: L'Oreal S. A., Paris (FR)

( * ) Notice: Subject to any disclaimer, the term of this patent is extended or adjusted under 35 U.S.C. 154(b) by 19 days.

(21) Appl. No.: 09/790,524

(22) Filed: Feb. 23, 2001

(65) Prior Publication Data

US 2001/0034914 A1 Nov. 1, 2001

(30) Foreign Application Priority Data

Feb. 23, 2000 (FR) .............................................. 0002335

(51) Int. Cl.$^7$ ................................................ A61K 7/13
(52) U.S. Cl. ...................... 8/405; 8/406; 8/407; 8/408; 8/409; 8/410; 8/412
(58) Field of Search ........................... 8/405, 406, 407, 8/408, 409, 410, 412

(56) References Cited

U.S. PATENT DOCUMENTS

| | | | |
|---|---|---|---|
| 2,795,610 A | 6/1957 | Gerjovich ................... | 260/553 |
| 3,674,414 A | 7/1972 | Kalopissis et al. ............... | 8/11 |
| 3,712,158 A | 1/1973 | Kalopissis et al. ............... | 8/11 |
| 3,767,412 A | 10/1973 | Monbaliu et al. ............. | 46/100 |
| 3,961,879 A | 6/1976 | Bugaut et al. ................ | 8/10.2 |
| 4,003,699 A | 1/1977 | Rose et al. .................... | 8/10.2 |
| 4,310,527 A | 1/1982 | Jaeggi et al. ............... | 424/251 |
| 4,492,709 A | 1/1985 | Purcell ....................... | 424/273 |
| 4,823,985 A | 4/1989 | Grollier et al. ................. | 222/1 |
| 4,829,047 A | 5/1989 | Niwa et al. .................. | 503/227 |
| 5,061,289 A | 10/1991 | Clausen et al. ................ | 8/405 |
| 5,334,225 A * | 8/1994 | Ogawa et al. ................ | 8/408 |
| 5,380,340 A | 1/1995 | Neunhoeffer et al. .......... | 8/409 |
| 5,676,706 A | 10/1997 | Akram et al. .................. | 8/416 |
| 5,766,576 A | 6/1998 | Löwe et al. .................. | 424/62 |
| 5,976,195 A * | 11/1999 | de la Mettrie et al. ......... | 8/411 |

FOREIGN PATENT DOCUMENTS

| | | | | |
|---|---|---|---|---|
| DE | 21 56 480 | 7/1972 | | |
| DE | 23 59 399 | 6/1975 | | |
| DE | 208 298 | 5/1984 | | |
| DE | 35 24 519 | 1/1986 | | |
| DE | 38 43 892 | 6/1990 | | |
| DE | 41 33 957 | 4/1993 | | |
| DE | 195 43 988 | 5/1997 | | |
| EP | 0 086 126 | 8/1983 | | |
| FR | 1 596 879 | 7/1970 | | |
| FR | 2 233 984 | 1/1975 | | |
| FR | 2 586 913 | 3/1987 | | |
| FR | 2 733 749 | 11/1996 | | |
| FR | 2 750 048 | 12/1997 | | |
| GB | 1 026 978 | 4/1966 | | |
| GB | 1 153 196 | 5/1969 | | |
| JP | 43-8269 | 3/1943 | | |
| JP | 60-108844 | 6/1985 | | |
| JP | 60-237444 | 11/1985 | | |
| JP | 61-35444 | 2/1986 | | |
| JP | 2-19576 | 1/1990 | | |
| JP | 2-220047 | 9/1990 | | |
| JP | 2521636 | 5/1996 | | |
| JP | 9-110659 | 4/1997 | | |
| WO | WO 94/08969 | 4/1994 | | |
| WO | WO 94 08970 | 4/1994 | | |
| WO | WO 96/15765 | 5/1996 | | |
| WO | WO 97/19998 | * 6/1997 | ............ | A61K/7/13 |
| WO | WO 98/52519 | 11/1998 | | |

OTHER PUBLICATIONS

English language Derwent Abstract of DD 208 298, May 1984.
English language Derwent Abstract of FR 2 733 749, Nov. 1996.
English language Derwent Abstract of JP 2–19576, Jan 23, 1990.
English language Derwent Abstract of DE 21 56 480, Jul. 6, 1972.
English language Derwent Abstract of FR 2 750 048, Dec. 26, 1997.
English language Derwent Abstract of JP 60–108844, Jun. 14, 1985.
English language Derwent Abstract of JP 60–237444, Nov. 26, 1985.
English language Derwent Abstract of JP 61–35444, Feb. 19, 1986.
English language Derwent Abstract of JP 2–220047, Sep. 3, 1990.
English language Derwent Abstract of JP 2521636, May 17, 1996.
English language Derwent Abstract of JP 9–110659, Apr. 28, 1997.
Ronald J. Nachman, "o–Hydroxyphenylureas. Intermediates in the Urea Fusion Synthesis of 2–Benzoxazolinones", Journal of Heterocyclic Chemistry, vol. 20, No. 5, Sep.–Oct. 1983, pp. 1423–1425.
Iwona Wawer et al., NMR Study of $N^1N^1$–dimethyl–$N^2$–arylureas, Journal of Molecular Structure, vol. 344, No. 3, Jan. 15, 1995, pp. 251–256.

* cited by examiner

Primary Examiner—Lorna M. Douyon
Assistant Examiner—Eisa Elhilo
(74) Attorney, Agent, or Firm—Finnegan, Henderson, Farabow, Garrett & Dunner

(57) ABSTRACT

Compositions for oxidation dyeing keratinous fibers, for example, human keratinous fibers such as hair, comprising at least one oxidation base and at least one coupler chosen from N-(2-hydroxybenzene)carbamate and N-(2-hydroxybenzene)urea compounds and their acid addition salts of formula (I) and processes comprising such compositions.

82 Claims, No Drawings

COMPOSITIONS FOR THE OXIDATION DYEING OF KERATINOUS FIBERS COMPRISING AT LEAST ONE COUPLER, AND DYEING METHODS

A subject of the invention is a composition for the oxidation dyeing of keratinous fibers, such as human keratinous fibers such as hair, comprising at least one oxidation base and at least one coupler chosen from N-(2-hydroxybenzene)carbamate and N-(2-hydroxybenzene)urea compounds of formula (I), their use as coupler for the oxidation dyeing of keratinous fibers, and the oxidation dyeing methods using them.

It is known to dye keratinous fibers, for example, human hair with dyeing compositions containing oxidation dye precursors, such as para-phenylenediamines, ortho-, and para-aminophenols, heterocyclic compounds such as diaminopyrazole derivatives, generally called oxidation bases. Oxidation dye precursors, i.e., oxidation bases, are colorless or weakly colored compounds which when combined with oxidizing products, can give rise, through a process of oxidative condensation, to colored or coloring compounds.

It is also known that it is possible to vary the shades obtained with these oxidation bases by combining them with couplers or color modifiers, the latter being chosen, for example, from aromatic meta-diamines, meta-aminophenols, meta-diphenols, noncationic naphthols or alternatively certain heterocyclic compounds such as indolic couplers.

The variety of molecules used in oxidation bases and couplers allows a rich palette of colors to be obtained.

The "permanent" color obtained using these oxidation dyes should moreover satisfy at least one of a number of objectives. Thus, it should, for example, satisfy at least one of the following: be without drawbacks from the toxicological point of view, make it possible to obtain shades in the desired intensity and exhibit good resistance towards external agents (at least one of light, adverse weather conditions, washing, permanent waving, perspiration, and rubbing).

The dyes may also cover grey hair and may also be the least selective possible, that is to say, make it possible to obtain the smallest possible differences in color right along the same keratinous fiber, which may indeed be differently sensitized (i.e. damaged) between its tip and its root.

Oxidation dyeing compositions containing certain derivatives of N-(2-hydroxy-4-aminophenyl)acetamide as couplers have already been described, for example, in patent applications WO 98/52519, JP2521636, FR-A-1 596 879 and FR-A-2 233 984. However, such compositions are not always satisfactory based on the intensity of the colors which may be obtained.

However, the inventors have discovered, completely unexpectedly and surprisingly, that compounds of N-(2-hydroxybenzene)carbamate and N-(2-hydroxybenzene)urea compounds of formula (I) defined below are suitable as couplers for oxidation dyeing, and that they make it possible to obtain dyeing compositions leading to at least one of the following advantages: intense colors which are particularly chromatic and brilliant, colors which are not very selective, a broad palette of colors, and properties of resistance to the various treatments to which keratinous fibers may be subjected.

One embodiment of the invention is therefore a composition for oxidation dyeing keratinous fibers, for example, human keratinous fibers such as hair, comprising in a medium suitable for dyeing:

(a) at least one oxidation base; and (b) at least one coupler chosen from compounds of formula (I) and acid addition salts thereof:

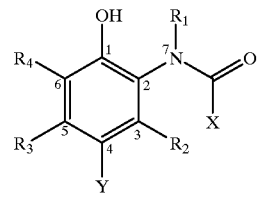

(I)

in which:

$R_1$ is chosen from a hydrogen atom, linear and branched, saturated and unsaturated (comprising, for example, at least one double bond and at least one triple bond) groups comprising from 1–15 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the provisos that:

(i) said $R_1$ does not comprise a group chosen from a peroxide group, a diazo group, a nitro group, and a nitroso group, and (ii) said $SO_2$ group is not directly linked to the nitrogen at the 7-position of formula (I);

X is chosen from groups $OR_5$ and $NR_6R_7$, wherein $R_5$ is chosen from linear and branched, saturated and unsaturated (comprising, for example, at least one double bond and at least one triple bond) groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:

(i) said $R_5$ does not comprise a group chosen from a peroxide group, a diazo group, a nitro group, and a nitroso group;

$R_6$ and $R_7$, which are identical or different, are each chosen from a hydrogen atom, linear and branched, saturated and unsaturated (comprising, for example, at least one double bond and at least one triple bond) groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:

(i) both said $R_6$ and $R_7$ do not comprise a group chosen from a peroxide group, a diazo group, a nitro group, and a nitroso group, and said $R_6$ and $R_7$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R, wherein R is chosen from linear, branched, saturated and unsaturated (comprising, for example, at least one double bond and at least one triple bond), $C_1$–$C_6$ alkyl groups, optionally substituted with at least one halogen atom, wherein at least one carbon atom is optionally replaced by a unit chosen from an oxygen atom, a nitrogen atom, a sulfur atom, and a $SO_2$ group, and at least one branch of said branched $C_1$–$C_6$ alkyl group optionally forms at least one saturated or unsaturated 3- to 6-membered ring; with the proviso that:
(i) said R does not comprise a group chosen from a peroxide group, a diazo group, a nitro group, and a nitroso group;

wherein said $R_1$ and said $R_5$ optionally form a ring chosen from a saturated and an unsaturated (comprising, for example, at least one double bond and at least one triple bond) ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group; and said $R_1$ and said $R_6$ optionally form a ring, chosen from a saturated and an unsaturated (comprising, for example, at least one double bond and at least one triple bond) ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

$R_2$, $R_3$, and $R_4$, which are identical or different, are each chosen from a hydrogen atom, a halogen atom, and linear and branched, saturated and unsaturated (comprising, for example, at least one double bond and at least one triple bond) groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally form at least one 3- to 7-membered ring comprising at least one carbon atom, with the provisos that:
(i) said $R_2$, $R_3$ and $R_4$ do not comprise a group chosen from a peroxide group, a diazo group, a nitro group, and a nitroso group;
(ii) said $R_4$ is chosen from a group other than a hydroxyl group, a thio group, an amino group, and a substituted or unsubstituted sulphonylamino group; and
(iii) said $R_2$, $R_3$ and $R_4$ are not directly linked to the benzene ring of formula (I) by a —NH—NH—;

wherein said $R_1$ and said $R_2$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

wherein said $R_2$ and said $R_5$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_5$ form a saturated ring comprising 5- to 7-members, said $R_5$ optionally is a bond;

wherein said $R_2$ and said $R_6$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_6$ form a saturated ring comprising 5- to 7-members, said $R_6$ optionally is a bond;

Y is chosen from:

a hydrogen atom;

a halogen atom;

a group chosen from —$OR_8$, —$SR_8$, and —NH—$SO_2R_8$, wherein $R_8$ is chosen from:
linear and branched $C_1$–$C_8$ alkyl groups, optionally substituted with at least one group chosen from a halogen atom, a hydroxyl group, $C_1$–$C_4$ alkoxy groups, an amino group, amino($C_1$–$C_4$ alkyl) groups, a carboxyl group, and $C_1$–$C_4$ alkoxycarbonyl groups, wherein at least one branch of said branched $C_1$–$C_8$ alkyl groups optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino ($C_1$–$C_4$ alkyl) groups; and
a benzyl group, optionally substituted with one or two oxy groups, with the proviso that:
(i) when $R_2$ is a hydroxyl group, Y is not a —NH—$SO_2R_8$ group;

provided that:
(i) when said $R_2$ and said $R_4$ are hydrogen atoms, and when said $R_3$ is chosen from substituted and unsubstituted $C_1$–$C_4$ alkyl groups, X is not a an —$OR_5$ group, wherein $R_5$ is chosen from substituted and unsubstituted $C_1$–$C_4$ alkyl groups;
(ii) when said $R_2$ and said $R_4$ are hydrogen atoms, and when said $R_3$ is chosen form substituted and unsubstituted $C_1$–$C_4$ alkyl groups, X is not a $NR_6R_7$ group; and
(iii) when said $R_2$, said $R_4$, and said Y, are hydrogen atoms, and when said X is a $NR_6R_7$ group, wherein said $R_6$ and $R_7$ are hydrogen atoms, said $R_3$ is not chosen from a fluorine atom, a chlorine atom and a bromine atom.

As indicated above, the colors obtained with the oxidation dyeing composition comprising a compound of formula (I)

in accordance with the invention can be intense or brilliant and can contribute to a palette of highly chromatic colors. Such compositions may also exhibit properties of resistance towards the action of various external agents (at least one of light, adverse weather conditions, washing, permanent waving, perspiration, and rubbing).

In one embodiment of the invention, when either one or both of the following conditions are present: (1) when one or more carbon atoms of the radical(s) $R_1$ to $R_7$ are replaced by a substituent chosen from an oxygen atom, a nitrogen atom, a sulfur atom, and a $SO_2$ group, and (2) when said radicals $R_1$ to $R_7$ are saturated (e.g., contain one or more double bonds and/or one or more triple bonds); it is possible, by way of example, to make the following conversions:

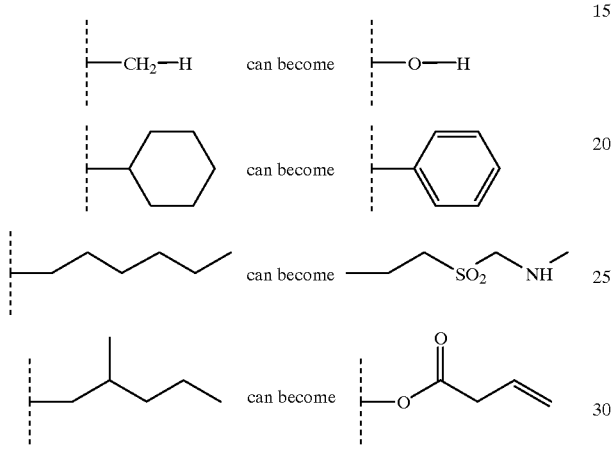

In one embodiment, $R_1$ is chosen from a hydrogen atom, and a group chosen from $A_1$, $A_2$, $A_3$, $A_4$ and $A_5$ as defined below, provided that when $R_1$ is chosen from Groups $A_1$, $A_2$, $A_3$, $A_4$, and $A_5$, $R_1$ is optionally attached to the nitrogen at the 7-position by way of a group —(CO)—.

a Group $A_1$, wherein said Group $A_1$ is chosen from a hydroxyl group, a dimethylamino group, and linear and branched $C_1$–$C_8$ alkyl groups optionally unsaturated (optionally comprising one double bond, two double bonds, or one triple bond) and optionally substituted with at least one unit chosen from:
  a group $A_2$, $A_4$, or $A_5$ as defined below;
  one or two groups, which may be identical or different, chosen from N—($C_1$–$C_3$)alkylamino, N—($C_1$–$C_3$)alkyl-N—($C_1$–$C_3$)alkylamino, ($C_1$–$C_6$)alkoxy, oxo, alkoxycarbonyl, acyloxy, amide, acylamino, ureyl, sulphoxy, sulphonyl, sulphonamido, sulphonylamino, bromo, cyano, amino, and carboxyl; and
  at least one group chosen from a hydroxyl group, a fluoro group and a chloro group;

a Group $A_2$, wherein said Group $A_2$ is an aromatic group chosen from a phenyl group, and a naphthyl group, wherein said aromatic group is optionally substituted with one to three groups, which are identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl, amino, an oxy, and cyano;

a Group $A_3$, wherein said Group $A_3$ is a heteroaromatic group chosen from furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl, wherein said heteroaromatic group is optionally substituted with 1 to 3 groups chosen from linear and branched $C_1$–$C_4$ alkyl groups, a $C_1$–$C_4$ monohydroxyalkyl group, a $C_2$–$C_4$ polyhydroxyalkyl group, a carboxyl group, an alkoxycarbonyl group, an amido group, an amino group, a hydroxyl group, and a halogen atom.

a Group $A_4$, wherein said Group $A_4$ is chosen from a $C_3$–$C_7$ cycloalkyl group and a norbornyl group; wherein said $C_3$–$C_7$ cycloalkyl group and said norbornyl group further comprise at least one double bond and wherein said $C_3$–$C_7$ cycloalkyl group and said norbornyl group are optionally substituted with 1 or 2 units chosen from linear and branched $C_1$–$C_4$ alkyl groups, a $C_1$–$C_4$ monohydroxyalkyl group, a $C_2$–$C_4$ polyhydroxyalkyl group, a carboxyl group, an alkoxycarbonyl group, an amido group, an amino group, a hydroxyl group, an oxy group, and a halogen atom.

a Group $A_5$, wherein said Group $A_5$ is a heterocycle chosen from dihydrofuranyl, tetrahydrofuranyl, butyrolactonyl, dihydrothiophenyl, tetrahydrothiophenyl, tetrahydrothiophenonyl, iminothiolane, dihydropyrrolyl, pyrrolidinyl, pyrrolidinonyl, imidazolidinonyl, imidazolidinethionyl, oxazolidinyl, oxazolidinonyl, oxazolanethione, thiazolidinyl, isothiazolonyl, mercaptothiazolinyl, pyrazolidinonyl, iminothiolane, dioxolanyl, pentalactone, dioxanyl, dihydropyridinyl, piperidinyl, pentalactam, morpholinyl, pyrazoli(di)nyl, pyrimi(di)nyl, pyrazinyl, piperazinyl, and azepinyl.

In another embodiment, $R_1$ is a chosen from:
a hydrogen atom;
a group chosen from methyl, ethyl, isopropyl, allyl, phenyl, benzyl, fluorobenzyl, difluorobenzyl, trifluorobenzyl, chlorobenzyl, bromobenzyl, methoxybenzyl, dimethoxybenzyl, (trifluoromethoxy) benzyl, 3,4-methylenedioxybenzyl, 6-chloropiperonyl, 4-methylthiobenzyl, 4-methylsulphonylbenzyl, 4-acetylaminobenzyl, 4-carboxybenzyl, 1-naphthomethyl and 2-naphthomethyl; and
a group chosen from 2-hydroxyethyl, 2-methoxyethyl and 2-ethoxyethyl.

In another embodiment, $R_1$ is chosen from a hydrogen atom and a methyl group.

In one embodiment, $R_5$ is chosen from Groups $A_1$, $A_2$, $A_3$, $A_4$, and $A_5$, as defined above. In yet another embodiment of the invention, $R_5$ is a group chosen from:
methyl, ethyl, propyl, isopropyl, butyl, isobutyl, tert-butyl, pentyl, isopentyl, neopentyl, hexyl, cyclopropyl, cyclobutyl, cyclopentyl, cyclohexyl, vinyl, 1-methylvinyl, 2-methylvinyl, 2,2-dimethylvinyl, allyl, propargyl, chloromethyl, 2-chloroethyl, 2-hydroxyethyl, 2-methoxyethyl, 4-chlorobutyl, phenyl, 4-methylphenyl, 4-ethylphenyl, 4-(trifluoromethyl)phenyl, 4-hydroxyphenyl, 4-methoxyphenyl, 4-ethoxyphenyl, 4-acetoxyphenyl, 4-aminophenyl, 4-fluorophenyl, 4-chlorophenyl, 4-bromophenyl, naphth-1-yl, naphth-2-yl, and benzyl.

In another embodiment, when $R_1$ and $R_5$ form a ring, the ring is a group chosen from 2-oxazolidon-1-yl, 4-methyloxazolidon-1-yl, and 5,5-dimethyloxazoline-2,4-dion-1-yl.

In another embodiment, $R_5$ is a group chosen from methyl, ethyl, propyl, isopropyl, butyl, isobutyl, 2-hydroxyethyl, 2-methoxyethyl, allyl, phenyl, benzyl, cyclopentyl, and cyclohexyl.

In one embodiment of the invention, $R_6$ and $R_7$, which are identical or different, are each chosen from $A_1$, $A_2$, $A_3$, $A_4$, and $A_5$, as defined above. In another embodiment, these substituents, $R_6$ and $R_7$, which are identical or different, are each chosen from:

a hydrogen atom, and
  a group chosen from methyl, ethyl, propyl, isopropyl, butyl, isobutyl, tert-butyl, pentyl, isopentyl, neopentyl, hexyl, cyclopentyl, cyclohexyl, allyl, propargyl, 2-chloroethyl, 2-hydroxyethyl, 2-methoxyethyl, 3-chloropropyl, 3-hydroxypropyl, 2,3-dihydroxypropyl, carboxymethyl, phenyl, fluorophenyl, (trifluoromethyl)phenyl, chlorophenyl, bromophenyl, methylphenyl, 4-acetylphenyl, methoxyphenyl, (trifluoromethoxy)phenyl, naphth-1-yl, benzyl, phenethyl and pyrid-3-yl.

In another embodiment, when $R_6$ and $R_7$ form a ring, said ring may be a group chosen from pyrrolidin-1-yl, 3-hydroxypyrrolidin-1-yl, 3,4-dihydroxypyrrolidin-1-yl, piperidin-1-yl, 3-hydroxypiperidin-1-yl, 4-hydroxypiperidin-1-yl, 4-morpholin-1-yl, piperazin-1-yl, 4-methylpiperazin-1-yl, and 4-(2-hydroxyethyl)piperazin-1-yl.

In still another embodiment, when $R_1$ and $R_6$ form a ring, the ring may be a group chosen from imidazolidin-2-on-1-yl and tetrahydropyrimidin-2-on-1-yl.

In one embodiment, $R_6$ and $R_7$, which are identical or different, are each chosen from a hydrogen atom, a methyl group, an ethyl group, a propyl group, an isopropyl group, a butyl group, an isobutyl group, an allyl group, a 2-hydroxyethyl group, a 2-methoxyethyl group, a 3-hydroxypropyl group, a 2,3-dihydroxypropyl group, a benzyl group, a cyclopentyl group, and cyclohexyl group.

In another embodiment, $R_2$ and $R_3$, which are identical or different, are each chosen from:

a hydrogen atom,
  a halogen atom,
  a hydroxyl group,
  an amino group,
  a group chosen from Group $A_1$, Group $A_4$, and Group $A_5$, as defined above,
  a group chosen from Group $A_1$, Group $A_2$, Group $A_3$, Group $A_4$ and Group $A_5$, as defined above, wherein said groups are attached to the phenolic nucleus in formula (I) by way of a group chosen from an oxygen atom, and a group chosen from —NH—, —Nalkyl($C_1$–$C_3$)—, —O(CO)—, —NH(CO)—, —Nalkyl($C_1$–$C_3$)(CO)—, —NH[C=NH]—, —NH(CO)NH—, —NH(CO)Nalkyl($C_1$–$C_3$)—, —NH(CO)O—, —NHSO$_2$—, —NHSO$_2$NH— and —NHSO$_2$Nalkyl($C_1$–$C_3$)—.

In another embodiment, among these substituents, $R_2$ is chosen from:

a hydrogen atom,
  a chlorine atom,
  a group chosen from methyl, hydroxymethyl, methoxymethyl, 2-hydroxyethyl, aminomethyl, methylaminomethyl, hydroxyl, methoxy, acetoxy, amino, methylamino and 2-hydroxyethylamino,
  a group —NH(CO)$R_9$, wherein in $R_9$ is a moiety of a group (G1) chosen from:
    methyl, ethyl, propyl, isopropyl, butyl, isobutyl, tert-butyl, pentyl, isopentyl, neopentyl, hexyl, cyclopropyl, cyclobutyl, cyclopentyl, cyclopentylmethyl, 3-cyclopentylpropyl, cyclohexyl, 2-cyclohexylethyl, norborn-2-yl, vinyl, 1-methylvinyl, 2-methylvinyl, 2,2-dimethylvinyl, allyl, 3-butenyl, phenyl, methylphenyl, dimethylphenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, naphth-1-yl, naphth-2-yl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl)methyl, (2-naphthyl)methyl, tetrahydrofuran-2-yl, furan-2-yl, 5-methyl-2-(trifluoromethyl)furan-3-yl, 2-methyl-5-phenylfuran-3-yl, thiophen-2-yl, (thiophen-2-yl)methyl, 3-chlorothiophen-2-yl, 2,5-dichlorothiophen-3-yl, benzothiophen-2-yl, 3-chlorobenzothiophen-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, indol-3-ylcarboxyl, pyridinyl, chloropyridinyl, dichloropyridinyl, 5-(bromo)pyridin-3-yl, piperazin-2-yl, quinoxal-2-yl, fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane, methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy, amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyridylamino, pyrid-3-ylamino, dimethylamino, 1-pyrrolidinyl and 4-morpholinyl radical,
  a group —NHSO$_2$R$_{10}$, wherein $R_{10}$ is a unit of a group (G2), chosen from:
    methyl, trifluoromethyl, ethyl, 2-chloroethyl, propyl, 3-chloropropyl, isopropyl, butyl, thiophen-2-yl, hydroxyl, ethoxy and dimethylamino.

In one embodiment, when $R_1$ and $R_2$ form a ring together with the nitrogen atom at the 7-position of the compound of formula (I), wherein —$R_1R_2$— may be —$CH_2CH_2CH_2$—.

In another embodiment, when $R_2$ and $R_5$ form a ring, together with the nitrogen atom at the 7-position of the compound of formula (I), wherein —$R_2R_5$— is chosen from —$CH_2$— and —$C(CH_3)_2$—.

In yet another embodiment of the invention, when $R_2$ and $R_6$ form a ring, together with the nitrogen atom at the 7-position of the compound of formula (I), wherein —$R_2R_6$— is chosen from —$CH_2$— and —$C(CH_3)_2$—.

In another embodiment of the invention, $R_2$ is chosen from:
- a hydrogen atom,
- a group chosen from methyl, hydroxymethyl, aminomethyl, hydroxyl, methoxy, amino, and methylamino,
- a group chosen from methanesulphonylamino, ethanesulphonylamino, and dimethylaminosulphonylamino, and
- a group —NH(CO)$R_{11}$ wherein $R_{11}$ is a radical of a group (G3) chosen from:
  methyl, ethyl, propyl, allyl, phenyl, tetrahydrofuran-2-yl, furan-2-yl, thiophen-2-yl, pyridinyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl and 4-morpholinyl.

Among these substituents, in one embodiment of the invention, $R_3$ is chosen from:
- a hydrogen atom,
- a chlorine atom,
- a group chosen from methyl, ethyl, hydroxymethyl, 2-hydroxyethyl, methoxymethyl, aminomethyl, methylaminomethyl, hydroxyl, methoxy, acetoxy, amino, methylamino, 2-hydroxyethylamino, N-piperidino and N-morpholino,
- a group —NH(CO)$R_{12}$, wherein $R_{12}$ is a unit of said group (G1), as defined above, and
- a group —NHSO$_2$$R_{13}$, wherein $R_{13}$ is a unit of said group (G2), as defined above.

In another embodiment, $R_3$ is chosen from
- a hydrogen atom,
- a chlorine atom,
- a group chosen from methyl, hydroxymethyl, aminomethyl, hydroxyl, methoxy, amino and methylamino,
- a group chosen from methanesulphonylamino, ethanesulphonylamino, and dimethylaminosulphonylamino, and
- a group —NH(CO)$R_{14}$ wherein $R_{14}$ is a unit of said group (G3), as defined above.

In one embodiment, $R_4$ is chosen from:
- a hydrogen atom,
- a halogen atom,
- a group chosen from $A_1$, $A_4$ and $A_5$, as defined above,
- a group chosen from $A_1$, $A_2$, $A_3$, $A_4$ and $A_5$, as defined above, wherein said groups are attached to the phenolic nucleus in formula (I) by way of a group chosen from an oxygen atom, a sulfur atom, and a group chosen from —NH—, —Nalkyl($C_1$–$C_3$)—, —O(CO)—, —NH(CO)—, —Nalkyl($C_1$–$C_3$)(CO)—, —NH[C=NH]—, —NH(CO)NH—, —NH(CO)Nalkyl($C_1$–$C_3$)—, and —NH(CO)O—.

In another embodiment, among these substituents, $R_4$ is chosen from:
- an atom chosen from hydrogen, chlorine, fluorine, and bromine,
- a group chosen from methyl, trifluoromethyl, allyl, hydroxymethyl, methoxymethyl, 2-hydroxyethyl, aminomethyl, methylaminomethyl, methoxy, acetoxy and methylamino, and
- a group —NH(CO)$R_{15}$ wherein $R_{15}$ is a unit of said group (G1), as defined above.

in yet another embodiment, $R_4$ is chosen from:
- an atom chosen from hydrogen, chlorine, and fluorine,
- a group chosen from methyl, hydroxymethyl, aminomethyl, methoxy and methylamino,
- a group —NH(CO)$R_{16}$ wherein $R_{16}$ is a unit of said group (G3), as defined above.

In one embodiment, Y is chosen from:
- an atom chosen from hydrogen, chlorine, fluorine, and bromine,
- a group chosen from methoxy, ethoxy, propoxy, benzyloxy, phenoxy, —OCH$_2$CH$_2$OCH$_3$, —OCH$_2$OCH$_2$OCH$_3$, —OCH$_2$CH$_2$N(CH$_3$)$_2$, —OCH$_2$(CO)OH, —OCH$_2$(CO)OCH$_3$, —OCH$_2$(CO)OC$_2$H$_5$, —SCH$_2$CH$_2$CO$_2$H, and —NHSO$_2$CH$_3$, with the proviso that when $R_2$ is a hydroxyl group, Y is other than a —NHSO$_2$CH$_3$ group.

In another embodiment, Y is chosen from a hydrogen atom, a chlorine atom, a methoxy group, a —OCH$_2$(CO)OH group, and a —OCH$_2$(CO)OCH$_3$ group.

In one embodiment, at least one coupler of formula (I), is chosen from the Groups (i), (ii), (iii), and (iv) in which:

Group (i) is said at least one coupler of formula (I), wherein:
  $R_1$ is a hydrogen atom,
  X is a group chosen from methoxy, ethoxy, propyloxy, isopropyloxy, butyloxy, isobutyloxy, 2-hydroxyethoxy, 2-methoxyethoxy, allyloxy, amino, methylamino, ethylamino, propylamino, isopropylamino, butylamino, isobutylamino, 2-hydroxyethylamino, 2-methoxyethylamino, 3-hydroxypropylamino, 2,3-dihydroxypropylamino, allylamino, dimethylamino, diethylamino, di(2-hydroxyethyl)amino, pyrrolidin-1-yl, 3-hydroxypyrrolidin-1-yl, and 3,4-dihydroxypyrrolidin-1-yl,
  $R_2$ is chosen from:
    a group chosen from hydroxyl, amino, methylamino, 2-hydroxyethylamino and diethylamino,
    a group —NH(CO)$R_{17}$, wherein $R_{17}$ is a unit of group (G4), said moiety is chosen from a methyl group, a methoxymethyl group, a 2-carboxyethyl group, a methoxy group, an amino group, an ethylamino group, a 1-pyrrolidinyl group, a methanesulphonylamino group, an ethanesulphonylamino group, and a dimethylaminosulphonylamino group,
  $R_3$ is chosen from a hydrogen atom, a chlorine atom, and a methyl group,
  $R_4$ is chosen from a hydrogen atom, a chlorine atom, a fluorine atom, and a methyl group, and
  Y is chosen from a hydrogen atom, a chlorine atom, a methoxy group, and a —OCH$_2$(CO)OCH$_3$ group, Group (ii) is said at least one coupler of formula (I), wherein:

$R_1$ is a hydrogen atom,

X is a group chosen from methoxy, ethoxy, propyloxy, isopropyloxy, butyloxy, isobutyloxy, 2-hydroxyethoxy, 2-methoxyethoxy, allyloxy, amino, methylamino, ethylamino, propylamino, isopropylamino, butylamino, isobutylamino, 2-hydroxyethylamino, 2-methoxyethylamino, 3-hydroxypropylamino, 2,3-dihydroxypropylamino, allylamino, dimethylamino, diethylamino, di(2-hydroxyethyl)amino, pyrrolidin-1-yl, 3-hydroxypyrrolidin-1-yl, and 3,4-dihydroxypyrrolidin-1-yl, $R_2$ is chosen from a hydrogen atom and a methyl group;

$R_3$ is chosen from:
  a group chosen from hydroxyl, amino, methylamino, 2-hydroxyethylamino, diethylamino, methanesulphonylamino, ethanesulphonylamino and dimethylaminosulphonylamino; and
  a group —NH(CO)$R_{18}$, wherein $R_{18}$ is a unit of group (G4), said moiety is chosen from a methyl group, a methoxymethyl group, a 2-carboxyethyl group, a methoxy group, an amino group, an ethylamino group, a 1-pyrrolidinyl group, a methanesulphonylamino group, an ethanesulphonylamino group, and a dimethylaminosulphonylamino group;

$R_4$ is chosen from a hydrogen atom, a chlorine atom, a fluorine atom, and a methyl group; and Y is a moiety chosen from a hydrogen atom, a chlorine atom, a methoxy group, and a —OCH$_2$(CO)OCH$_3$ group;

Group (iii) is said at least one coupler of formula (I) wherein:

$R_1$ is a hydrogen atom;

X is a group chosen from methoxy, ethoxy, propyloxy, isopropyloxy, butyloxy, isobutyloxy, 2-hydroxyethoxy, 2-methoxyethoxy, allyloxy, amino, methylamino, ethylamino, propylamino, isopropylamino, butylamino, isobutylamino, 2-hydroxyethylamino, 2-methoxyethylamino, 3-hydroxypropylamino, 2,3-dihydroxypropylamino, allylamino, dimethylamino, diethylamino, di(2-hydroxyethyl)amino, pyrrolidin-1-yl, 3-hydroxypyrrolidin-1-yl, and 3,4-dihydroxypyrrolidin-1-yl;

$R_2$ is chosen from a hydrogen atom, and a methyl group;

$R_3$ is chosen from a hydrogen atom, a chlorine atom, a methyl group, a methoxy group and a methylamino group;

$R_4$ represents a group —NH(CO)$R_{19}$, wherein $R_{19}$ is a unit of group (G4), said moiety is chosen from a methyl group, a methoxymethyl group, a 2-carboxyethyl group, a methoxy group, an amino group, an ethylamino group, a 1-pyrrolidinyl group; a methanesulphonylamino group, an ethanesulphonylamino group, and a dimethylaminosulphonylamino group; and Y is chosen from a hydrogen atom, a chlorine atom, a methoxy group, and a —OCH$_2$(CO)OCH$_3$ group; and Group (iv) is said at least one coupler of formula (I) wherein:

$R_1$ is a hydrogen atom;

X is a group chosen from methoxy, ethoxy, propyloxy, isopropyloxy, butyloxy, isobutyloxy, 2-hydroxyethoxy, 2-methoxyethoxy, allyloxy, amino, methylamino, ethylamino, propylamino, isopropylamino, butylamino, isobutylamino, 2-hydroxyethylamino, 2-methoxyethylamino, 3-hydroxypropylamino, 2,3-dihydroxypropylamino, allylamino, dimethylamino, diethylamino, di(2-hydroxyethyl)amino, pyrrolidin-1-yl, 3-hydroxypyrrolidin-1-yl, and 3,4-dihydroxypyrrolidin-1-yl;

$R_2$ is chosen from a hydrogen atom and a methyl group;

$R_3$ is chosen from a hydrogen atom, a methyl group and an ethyl group;

$R_4$ is chosen from a hydrogen atom, a chlorine atom, and a fluorine atom; and

Y is chosen from a hydrogen atom, a chlorine atom and a —OCH$_2$(CO)OCH$_3$ group.

In one embodiment of the invention, the at least one coupler of formula (I) is chosen from:

(2-Hydroxyphenyl)carbamic acid methyl ester,
(2-Hydroxyphenyl)carbamic acid ethyl ester,
(2-Hydroxyphenyl)carbamic acid 2-hydroxyethyl ester,
(2-Hydroxyphenyl)carbamic acid isopropyl ester,
1-(2-Hydroxyphenyl)urea,
3-(2-Hydroxyphenyl)-1-methylurea,
3-(2-Hydroxyphenyl)-1-ethylurea,
3-(2-Hydroxyphenyl)-1-(2-hydroxyethyl)urea,
3-(2-Hydroxyphenyl)-1-isopropylurea,
3-(2-Hydroxyphenyl)-1,1-dimethylurea,
3-(2-Hydroxyphenyl)-1,1-diethylurea,
3-(2-Hydroxyphenyl)-1,1-di(2-hydroxyethyl)urea,
(2-Hydroxy-5-chlorophenyl)carbamic acid methyl ester,
(2-Hydroxy-5-chlorophenyl)carbamic acid ethyl ester,
(2-Hydroxy-5-chlorophenyl)carbamic acid 2-hydroxyethyl ester,
(2-Hydroxy-5-chlorophenyl)carbamic acid isopropyl ester,
1-(2-Hydroxy-5-chlorophenyl)urea,
3-(2-Hydroxy-5-chlorophenyl)-1-methylurea,
3-(2-Hydroxy-5-chlorophenyl)-1-ethylurea,
3-(2-Hydroxy-5-chlorophenyl)-1-(2-hydroxyethyl)urea,
3-(2-Hydroxy-5-chlorophenyl)-1-isopropylurea,
3-(2-Hydroxy-5-chlorophenyl)-1,1-dimethylurea,
3-(2-Hydroxy-5-chlorophenyl)-1,1-diethylurea,
3-(2-Hydroxy-5-chlorophenyl)-1,1-di(2-hydroxyethyl)urea,
(2-Hydroxy-5-methoxyphenyl)carbamic acid methyl ester,
(2-Hydroxy-5-methoxyphenyl)carbamic acid ethyl ester,
(2-Hydroxy-5-methoxyphenyl)carbamic acid 2-hydroxyethyl ester,
(2-Hydroxy-5-methoxyphenyl)carbamic acid isopropyl ester,
3-(2-Hydroxy-5-methoxyphenyl)-1-(2-hydroxyethyl)urea,
3-(2-Hydroxy-5-methoxyphenyl)-1,1-di(2-hydroxyethyl)urea,
(2-Hydroxy-6-aminophenyl)carbamic acid methyl ester,
(2-Hydroxy-6-aminophenyl)carbamic acid ethyl ester,
(2-Hydroxy-6-aminophenyl)carbamic acid 2-hydroxyethyl ester,
(2-Hydroxy-6-aminophenyl)carbamic acid isopropyl ester,
1-(2-Hydroxy-6-aminophenyl)urea, 3-(2-Hydroxy-6-aminophenyl)-1-methylurea,
3-(2-Hydroxy-6-aminophenyl)-1-ethylurea,
3-(2-Hydroxy-6-aminophenyl)-1-(2-hydroxyethyl)urea,
3-(2-Hydroxy-6-aminophenyl)-1-isopropylurea,
3-(2-Hydroxy-6-aminophenyl)-1,1-dimethylurea,
3-(2-Hydroxy-6-aminophenyl)-1,1-diethylurea,
3-(2-Hydroxy-6-aminophenyl)-1,1-di(2-hydroxyethyl)urea,
(2-Hydroxy-4-aminophenyl)carbamic acid methyl ester,
(2-Hydroxy-4-aminophenyl)carbamic acid ethyl ester,
(2-Hydroxy-4-aminophenyl)carbamic acid 2-hydroxyethyl ester,
(2-Hydroxy-4-aminophenyl)carbamic acid isopropyl ester,
1-(2-Hydroxy-4-aminophenyl)urea,
3-(2-Hydroxy-4-aminophenyl)-1-methylurea,
3-(2-Hydroxy-4-aminophenyl)-1-ethylurea,
3-(2-Hydroxy-4-aminophenyl)-1-(2-hydroxyethyl)urea,
3-(2-Hydroxy-4-aminophenyl)-1-isopropylurea,
3-(2-Hydroxy-4-aminophenyl)-1,1-dimethylurea,
3-(2-Hydroxy-4-aminophenyl)-1,1-diethylurea,
3-(2-Hydroxy-4-aminophenyl)-1,1-di(2-hydroxyethyl)urea,
Pyrrolidine-1-carboxylic acid (4-amino-2-hydroxyphenyl)amide,
3-Hydroxypyrrolidine-1-carboxylic acid (4-amino-2-hydroxyphenyl)amide,
(2-Hydroxy-4-methylaminophenyl)carbamic acid methyl ester,
(2-Hydroxy-4-methylaminophenyl)carbamic acid ethyl ester,
(2-Hydroxy-4-methylaminophenyl)carbamic acid 2-hydroxyethyl ester,
(2-Hydroxy-4-methylaminophenyl)carbamic acid isopropyl ester,
1-(2-Hydroxy-4-methylaminophenyl)urea,
3-(2-Hydroxy-4-methylaminophenyl)-1-methylurea,
3-(2-Hydroxy-4-methylaminophenyl)-1-ethylurea,
3-(2-Hydroxy-4-methylaminophenyl)-1-(2-hydroxyethyl)urea,
3-(2-Hydroxy-4-methylaminophenyl)-1-isopropylurea,
3-(2-Hydroxy-4-methylaminophenyl)-1,1-dimethylurea,
3-(2-Hydroxy-4-methylaminophenyl)-1,1-diethylurea,
3-(2-Hydroxy-4-methylaminophenyl)-1,1-di(2-hydroxyethyl)urea,
(2-Hydroxy-4-(2-hydroxyethyl)aminophenyl)carbamic acid methyl ester,
(2-Hydroxy-4-(2-hydroxyethyl)aminophenyl)carbamic acid ethyl ester,
(2-Hydroxy-4-(2-hydroxyethyl)aminophenyl)carbamic acid 2-hydroxyethyl ester,
(2-Hydroxy-4-(2-hydroxyethyl)aminophenyl)carbamic acid isopropyl ester,
1-(2-Hydroxy-4-(2-hydroxyethyl)aminophenyl)urea,
3-(2-Hydroxy-4-(2-hydroxyethyl)aminophenyl)-1-methylurea,
3-(2-Hydroxy-4-(2-hydroxyethyl)aminophenyl)-1-ethylurea,
3-(2-Hydroxy-4-(2-hydroxyethyl)aminophenyl)-1-(2-hydroxyethyl)urea,
3-(2-Hydroxy-4-(2-hydroxyethyl)aminophenyl)-1-isopropylurea,
3-(2-Hydroxy-4-(2-hydroxyethyl)aminophenyl)-1,1-dimethylurea,
3-(2-Hydroxy-4-(2-hydroxyethyl)aminophenyl)-1,1-diethylurea,
3-(2-Hydroxy-4-(2-hydroxyethyl)aminophenyl)-1,1-di(2-hydroxyethyl)urea,
(2-Hydroxy-4-amino-5-chlorophenyl)carbamic acid methyl ester,
(2-Hydroxy-4-amino-5-chlorophenyl)carbamic acid ethyl ester,
(2-Hydroxy-4-amino-5-chlorophenyl)carbamic acid 2-hydroxyethyl ester,
(2-Hydroxy-4-amino-5-chlorophenyl)carbamic acid isopropyl ester,
1-(2-Hydroxy-4-amino-5-chlorophenyl)urea,
3-(2-Hydroxy-4-amino-5-chlorophenyl)-1-methylurea,
3-(2-Hydroxy-4-amino-5-chlorophenyl)-1-ethylurea,
3-(2-Hydroxy-4-amino-5-chlorophenyl)-1-(2-hydroxyethyl)urea,
3-(2-Hydroxy-4-amino-5-chlorophenyl)-1-isopropylurea,
3-(2-Hydroxy-4-amino-5-chlorophenyl)-1,1-dimethylurea,
3-(2-Hydroxy-4-amino-5-chlorophenyl)-1,1-diethylurea,
3-(2-Hydroxy-4-amino-5-chlorophenyl)-1,1-di(2-hydroxyethyl)urea,
(2-Hydroxy-4-methylamino-5-chlorophenyl)carbamic acid methyl ester,
(2-Hydroxy-4-methylamino-5-chlorophenyl)carbamic acid ethyl ester,
(2-Hydroxy-4-methylamino-5-chlorophenyl)carbamic acid 2-hydroxyethyl ester,
(2-Hydroxy-4-methylamino-5-chlorophenyl)carbamic acid isopropyl ester,
1-(2-Hydroxy-4-methylamino-5-chlorophenyl)urea,
3-(2-Hydroxy-4-methylamino-5-chlorophenyl)-1-methylurea,
3-(2-Hydroxy-4-methylamino-5-chlorophenyl)-1-ethylurea,
3-(2-Hydroxy-4-methylamino-5-chlorophenyl)-1-(2-hydroxyethyl)urea,
3-(2-Hydroxy-4-methylamino-5-chlorophenyl)-1-isopropylurea,
3-(2-Hydroxy-4-methylamino-5-chlorophenyl)-1,1-dimethylurea,
3-(2-Hydroxy-4-methylamino-5-chlorophenyl)-1,1-diethylurea,
3-(2-Hydroxy-4-methylamino-5-chlorophenyl)-1,1-di(2-hydroxyethyl)urea,
(2-Hydroxy-4-(2-hydroxyethyl)amino-5-chlorophenyl)carbamic acid methyl ester,
(2-Hydroxy-4-(2-hydroxyethyl)amino-5-chlorophenyl)carbamic acid ethyl ester,
(2-Hydroxy-4-(2-hydroxyethyl)amino-5-chlorophenyl)carbamic acid 2-hydroxyethyl ester,
(2-Hydroxy-4-(2-hydroxyethyl)amino-5-chlorophenyl)carbamic acid isopropyl ester,
1(2-Hydroxy-4-(2-hydroxyethyl)amino-5-chlorophenyl)urea,
3-(2-Hydroxy-4-(2-hydroxyethyl)amino-5-chlorophenyl)-1-methylurea, 3-(2-Hydroxy-4-(2-hydroxyethyl)amino-5-chlorophenyl)-1-ethylurea,
3-(2-Hydroxy-4-(2-hydroxyethyl)amino-5-chlorophenyl)-1-(2-hydroxyethyl)urea,
3-(2-Hydroxy-4-(2-hydroxyethyl)amino-5-chlorophenyl)-1-isopropylurea,
3-(2-Hydroxy-4-(2-hydroxyethyl)amino-5-chlorophenyl)-1,1-dimethylurea,
3-(2-Hydroxy-4-(2-hydroxyethyl)amino-5-chlorophenyl)-1,1-diethylurea,
3-(2-Hydroxy-4-(2-hydroxyethyl)amino-5-chlorophenyl)-1,1-di(2-hydroxyethyl)urea,
(2-Hydroxy-4-amino-5-methoxyphenyl)carbamic acid methyl ester,
(2-Hydroxy-4-amino-5-methoxyphenyl)carbamic acid ethyl ester,
(2-Hydroxy-4-amino-5-methoxyphenyl)carbamic acid 2-hydroxyethyl ester,
(2-Hydroxy-4-amino-5-methoxyphenyl)carbamic acid isopropyl ester,
3-(2-Hydroxy-4-amino-5-methoxyphenyl)-1-(2-hydroxyethyl)urea,
3-(2-Hydroxy-4-amino-5-methoxyphenyl)-1,1-di(2-hydroxyethyl)urea,
(2-Hydroxy-4-methylamino-5-methoxyphenyl)carbamic acid methyl ester,
(2-Hydroxy-4-methylamino-5-methoxyphenyl)carbamic acid ethyl ester,
(2-Hydroxy-4-methylamino-5-methoxyphenyl)carbamic acid 2-hydroxyethyl ester,
(2-Hydroxy-4-methylamino-5-methoxyphenyl)carbamic acid isopropyl ester,
1-(2-Hydroxy-4-methylamino-5-methoxyphenyl)urea,
3-(2-Hydroxy-4-methylamino-5-methoxyphenyl)-1-methylurea,
3-(2-Hydroxy-4-methylamino-5-methoxyphenyl)-1-ethylurea,
3-(2-Hydroxy-4-methylamino-5-methoxyphenyl)-1-(2-hydroxyethyl)urea,
3-(2-Hydroxy-4-methylamino-5-methoxyphenyl)-1-isopropylurea,
3-(2-Hydroxy-4-methylamino-5-methoxyphenyl)-1,1-dimethylurea,
3-(2-Hydroxy-4-methylamino-5-methoxyphenyl)-1,1-diethylurea,
3-(2-Hydroxy-4-methylamino-5-methoxyphenyl)-1,1-di(2-hydroxyethyl)urea,
(2-Hydroxy-4-(2-hydroxyethyl)amino-5-methoxyphenyl)carbamic acid methyl ester,
(2-Hydroxy-4-(2-hydroxyethyl)amino-5-methoxyphenyl)carbamic acid ethyl ester,
(2-Hydroxy-4-(2-hydroxyethyl)amino-5-methoxyphenyl)carbamic acid 2-hydroxyethyl ester,
(2-Hydroxy-4-(2-hydroxyethyl)amino-5-methoxyphenyl)carbamic acid isopropyl ester,
1(2-Hydroxy-4-(2-hydroxyethyl)amino-5-methoxyphenyl)urea,
3(2-Hydroxy-4-(2-hydroxyethyl)amino-5-methoxyphenyl)-1-methylurea,
3(2-Hydroxy-4-(2-hydroxyethyl)amino-5-methoxyphenyl)-1-ethylurea,
3-(2-Hydroxy-4-(2-hydroxyethyl)amino-5-methoxyphenyl)-1-(2-hydroxyethyl)urea,
3-(2-Hydroxy-4-(2-hydroxyethyl)amino-5-methoxyphenyl)-1-isopropylurea,
3-(2-Hydroxy-4-(2-hydroxyethyl)amino-5-methoxyphenyl)-1,1-dimethylurea,
3-(2-Hydroxy-4-(2-hydroxyethyl)amino-5-methoxyphenyl)-1,1-diethylurea,
3-(2-Hydroxy-4-(2-hydroxyethyl)amino-5-methoxyphenyl)-1,1-di(2-hydroxyethyl)urea,
(2-Hydroxy-3-methoxycarbonylaminophenyl)carbamic acid methyl ester,
(2-Hydroxy-3-ethoxycarbonylaminophenyl)carbamic acid ethyl ester,
(2-Hydroxy-3-(2-hydroxyethoxy)carbonylaminophenyl)-carbamic acid 2-hydroxyethyl ester,
(2-Hydroxy-3-isopropoxycarbonylaminophenyl)carbamic acid isopropyl ester,
1-(2-Hydroxy-3-ureidophenyl)urea,
3-(2-Hydroxy-3-(3-methylureido)phenyl)-1-methylurea,
3-(2-Hydroxy-3-(3-ethylureido)phenyl)-1-ethylurea,
3-(2-Hydroxy-3-(3-(2-hydroxyethyl)ureido)phenyl)-1-(2-hydroxyethyl)urea,
3-(2-Hydroxy-3-(3-isopropylureido)phenyl)-1-isopropylurea,
3-(2-Hydroxy-3-(3,3-dimethylureido)phenyl)-1,1-dimethylurea, and their acid addition salts.

In another embodiment, at least one coupler of formula (I) is chosen from:
(2-Hydroxy-4-aminophenyl)carbamic acid methyl ester,
(2-Hydroxy-4-aminophenyl)carbamic acid ethyl ester,
(2-Hydroxy-4-aminophenyl)carbamic acid 2-hydroxyethyl ester,
(2-Hydroxy-4-aminophenyl)carbamic acid isopropyl ester,
1-(2-Hydroxy-4-aminophenyl)urea,
3-(2-Hydroxy-4-aminophenyl)-1-methylurea,
3-(2-Hydroxy-4-aminophenyl)-1-ethylurea,
3-(2-Hydroxy-4-aminophenyl)-1-(2-hydroxyethyl)urea,
3-(2-Hydroxy-4-aminophenyl)-1-isopropylurea,
3-(2-Hydroxy-4-aminophenyl)-1,1-dimethylurea,
(2-Hydroxy-4-methylaminophenyl)carbamic acid methyl ester,
(2-Hydroxy-4-methylaminophenyl)carbamic acid ethyl ester,
(2-Hydroxy-4-methylaminophenyl)carbamic acid 2-hydroxyethyl ester,
(2-Hydroxy-4-methylaminophenyl)carbamic acid isopropyl ester,
1(2-Hydroxy-4-methylaminophenyl)urea,
3-(2-Hydroxy-4-methylaminophenyl)-1-methylurea,
3-(2-Hydroxy-4-methylaminophenyl)-1-ethylurea,
3-(2-Hydroxy-4-methylaminophenyl)-1-(2-hydroxyethyl)urea,
3-(2-Hydroxy-4-methylaminophenyl)-1-isopropylurea,
3-(2-Hydroxy-4-methylaminophenyl)-1,1-dimethylurea,
(2-Hydroxy-4-(2-hydroxyethyl)aminophenyl)carbamic acid methyl ester,
(2-Hydroxy-4-(2-hydroxyethyl)aminophenyl)carbamic acid ethyl ester, (2-Hydroxy-4-(2-hydroxyethyl)aminophenyl)carbamic acid 2-hydroxyethyl ester,
(2-Hydroxy-4-(2-hydroxyethyl)aminophenyl)carbamic acid isopropyl ester,
1-(2-Hydroxy-4-(2-hydroxyethyl)aminophenyl)urea,
3-(2-Hydroxy-4-(2-hydroxyethyl)aminophenyl)-1-methylurea,
3-(2-Hydroxy-4-(2-hydroxyethyl)aminophenyl)-1-ethylurea,
3-(2-Hydroxy-4-(2-hydroxyethyl)aminophenyl)-1-(2-hydroxyethyl)urea,
3-(2-Hydroxy-4-(2-hydroxyethyl)aminophenyl)-1-isopropylurea,
3-(2-Hydroxy-4-(2-hydroxyethyl)aminophenyl)-1,1-dimethylurea,
(2-Hydroxy-4-amino-5-chlorophenyl)carbamic acid methyl ester,
(2-Hydroxy-4-amino-5-chlorophenyl)carbamic acid ethyl ester,
(2-Hydroxy-4-amino-5-chlorophenyl)carbamic acid 2-hydroxyethyl ester,
(2-Hydroxy-4-amino-5-chlorophenyl)carbamic acid isopropyl ester,
1-(2-Hydroxy-4-amino-5-chlorophenyl)urea,
3-(2-Hydroxy-4-amino-5-chlorophenyl)-1-methylurea,
3-(2-Hydroxy-4-amino-5-chlorophenyl)-1-ethylurea,
3-(2-Hydroxy-4-amino-5-chlorophenyl)-1-(2-hydroxyethyl)urea,
3-(2-Hydroxy-4-amino-5-chlorophenyl)-1-isopropylurea,
3-(2-Hydroxy-4-amino-5-chlorophenyl)-1,1-dimethylurea,
(2-Hydroxy-4-methylamino-5-chlorophenyl)carbamic acid methyl ester,
(2-Hydroxy-4-methylamino-5-chlorophenyl)carbamic acid ethyl ester,
(2-Hydroxy-4-methylamino-5-chlorophenyl)carbamic acid 2-hydroxyethyl ester,
(2-Hydroxy-4-methylamino-5-chlorophenyl)carbamic acid isopropyl ester,
(2-Hydroxy-4-methylamino-5-chlorophenyl)urea,
3-(2-Hydroxy-4-methylamino-5-chlorophenyl)-1-methylurea,
3-(2-Hydroxy-4-methylamino-5-chlorophenyl)-1-ethylurea,
3-(2-Hydroxy-4-methylamino-5-chlorophenyl)-1-(2-hydroxyethyl)urea,
3-(2-Hydroxy-4-methylamino-5-chlorophenyl)-1-isopropylurea,
3-(2-Hydroxy-4-methylamino-5-chlorophenyl)-1,1-dimethylurea,
(2-Hydroxy-4-(2-hydroxyethyl)amino-5-chlorophenyl) carbamic acid methyl ester,
(2-Hydroxy-4-(2-hydroxyethyl)amino-5-chlorophenyl) carbamic acid ethyl ester,
(2-Hydroxy-4-(2-hydroxyethyl)amino-5-chlorophenyl) carbamic acid 2-hydroxyethyl ester,
(2-Hydroxy-4-(2-hydroxyethyl)amino-5-chlorophenyl) carbamic acid isopropyl ester,
1-(2-Hydroxy-4-(2-hydroxyethyl)amino-5-chlorophenyl) urea,
3-(2-Hydroxy-4-(2-hydroxyethyl)amino-5-chlorophenyl)-1-methylurea,
3-(2-Hydroxy-4-(2-hydroxyethyl)amino-5-chlorophenyl)-1-ethylurea,
3-(2-Hydroxy-4-(2-hydroxyethyl)amino-5-chlorophenyl)-1-(2-hydroxyethyl)urea,
3-(2-Hydroxy-4-(2-hydroxyethyl)amino-5-chlorophenyl)-1-isopropylurea,
3-(2-Hydroxy-4-(2-hydroxyethyl)amino-5-chlorophenyl)-1,1-dimethylurea,
(2-Hydroxy-4-amino-5-methoxyphenyl)carbamic acid methyl ester,
(2-Hydroxy-4-amino-5-methoxyphenyl)carbamic acid ethyl ester,
(2-Hydroxy-4-amino-5-methoxyphenyl)carbamic acid 2-hydroxyethyl ester,
(2-Hydroxy-4-amino-5-methoxyphenyl)carbamic acid isopropyl ester,
3-(2-Hydroxy-4-amino-5-methoxyphenyl)-1-(2-hydroxyethyl)urea,
(2-Hydroxy-4-methylamino-5-methoxyphenyl)carbamic acid methyl ester,
(2-Hydroxy-4-methylamino-5-methoxyphenyl)carbamic acid ethyl ester,
(2-Hydroxy-4-methylamino-5-methoxyphenyl)carbamic acid 2-hydroxyethyl ester,
(2-Hydroxy-4-methylamino-5-methoxyphenyl)carbamic acid isopropyl ester,
1-(2-Hydroxy-4-methylamino-5-methoxyphenyl)urea,
3-(2-Hydroxy-4-methylamino-5-methoxyphenyl)-1-methylurea,
3-(2-Hydroxy-4-methylamino-5-methoxyphenyl)-1-ethylurea,
3-(2-Hydroxy-4-methylamino-5-methoxyphenyl)-1-(2-hydroxyethyl)urea,
3-(2-Hydroxy-4-methylamino-5-methoxyphenyl)-1-isopropylurea,
3-(2-Hydroxy-4-methylamino-5-methoxyphenyl)-1,1-dimethylurea,
(2-Hydroxy-4-(2-hydroxyethyl)amino-5-methoxyphenyl) carbamic acid methyl ester,
(2-Hydroxy-4-(2-hydroxyethyl)amino-5-methoxyphenyl) carbamic acid ethyl ester,
(2-Hydroxy-4-(2-hydroxyethyl)amino-5-methoxyphenyl) carbamic acid 2-hydroxyethyl ester,
(2-Hydroxy-4-(2-hydroxyethyl)amino-5-ethoxyphenyl) carbamic acid isopropyl ester,
1-(2-Hydroxy-4-(2-hydroxyethyl)amino-5-methoxyphenyl)urea,
3-(2-Hydroxy-4-(2-hydroxyethyl)amino-5-methoxyphenyl)-1-methylurea,
3-(2-Hydroxy-4-(2-hydroxyethyl)amino-5-methoxyphenyl)-1-ethylurea,
3-(2-Hydroxy-4-(2-hydroxyethyl)amino-5-methoxyphenyl)-1-(2-hydroxyethyl)urea,
3-(2-Hydroxy-4-(2-hydroxyethyl)amino-5-methoxyphenyl)-1-isopropylurea,
3-(2-Hydroxy-4-(2-hydroxyethyl)amino-5-methoxyphenyl)-1,1-dimethylurea, and their acid addition salts.

In another embodiment of the invention, the at least one coupler of formula (I) is chosen from:
(2-Hydroxy-4-aminophenyl)carbamic acid methyl ester,
(2-Hydroxy-4-aminophenyl)carbamic acid ethyl ester,
(2-Hydroxy-4-aminophenyl)carbamic acid 2-hydroxyethyl ester, (2-Hydroxy-4-aminophenyl)carbamic acid isopropyl ester, 1-(2-Hydroxy-4-aminophenyl)urea, 3-(2-Hydroxy-4-aminophenyl)-1-methylurea, 3-(2-Hydroxy-4-aminophenyl)-1-ethylurea, 3-(2-Hydroxy-4-aminophenyl)-1-(2-hydroxyethyl)urea, 3-(2-Hydroxy-4-aminophenyl)-1-isopropylurea, 3-(2-Hydroxy-4-aminophenyl)-1,1-dimethylurea, (2-Hydroxy-4-amino-5-chlorophenyl)carbamic acid methyl ester, (2-Hydroxy-4-amino-5-chlorophenyl)carbamic acid ethyl ester, (2-Hydroxy-4-amino-5-chlorophenyl)carbamic acid 2-hydroxyethyl ester, (2-Hydroxy-4-amino-5-chlorophenyl)carbamic acid isopropyl ester, 1-(2-Hydroxy-4-amino-5-chlorophenyl)urea, 3-(2-Hydroxy-4-amino-5-chlorophenyl)-1-methylurea, 3-(2-Hydroxy-4-amino-5-chlorophenyl)-1-ethylurea, 3-(2-Hydroxy-4-amino-5-chlorophenyl)-1-(2-hydroxyethyl)urea, 3-(2-Hydroxy-4-amino-5-chlorophenyl)-1-isopropylurea, 3-(2-Hydroxy-4-amino-5-chlorophenyl)-1,1-dimethylurea, (2-Hydroxy-4-amino-5-methoxyphenyl)carbamic acid methyl ester, (2-Hydroxy-4-amino-5-methoxyphenyl)carbamic acid ethyl ester, (2-Hydroxy-4-amino-5-methoxyphenyl)carbamic acid 2-hydroxyethyl ester, (2-Hydroxy-4-amino-5-methoxyphenyl)carbamic acid isopropyl ester, 3-(2-Hydroxy-4-amino-5-methoxyphenyl)-1-(2-hydroxyethyl)urea, and their acid addition salts.

The compounds of formula (I) in accordance with the invention are known compounds which may be prepared according to conventional methods well known in the state of the art and which are described, for, example, in patent applications and patents JP 43008269, DE 2 156 480, U.S. Pat. No. 4,310,527, JP 60108844, CS 235432, U.S. Pat. No. 3,767,412, JP 02220047, JP 61035444, JP 60237444, DE 3 524 519, EP 0 086 126, U.S. Pat. No. 2,795,610 or in *J. Heterocyclic Chem.* 1983, 20, 1423, *J. Mol. Struct.* 1995, 344, 251, which are incorporated by reference herein.

The at least one coupler of formula (I) in accordance with the invention is present, for example, in an amount ranging from 0.0005 to 12% by weight relative to the total weight of the dyeing composition. In another embodiment, at least one coupler of formula (I) is present, for example, in an amount ranging from 0.005 to 6% by weight relative to the total weight of the dyeing composition.

The nature of the at least one oxidation base which may be used in the dyeing composition in accordance with the invention is not critical. The at least one oxidation base may be chosen from oxidation bases conventionally used in oxidation dyeing, for example, para-phenylenediamines, bisphenylalkylenediamines, para-aminophenols, ortho-aminophenols and heterocyclic bases.

Examples of para-phenylenediamines comprise para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and their acid addition salts.

In one embodiment of the invention, the para-phenylenediamines are chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, and 2-β-acetylaminoethyloxy-para-phenylenediamine, and their acid addition salts.

Examples of the bisphenylalkylenediamines may include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,5-dioxaoctane, and their acid addition salts.

Examples of the para-aminophenols may include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their acid addition salts.

Examples of the ortho-aminophenols may include 2-aminophenol, 2-amino-5-methylphenol, 2-amino-6-methylphenol, 5-acetamido-2-aminophenol, and their acid addition salts.

Examples of the heterocyclic bases may include pyridine derivatives, pyrimidine derivatives and pyrazole derivatives.

Examples of the pyridine derivatives may include the compounds described, for example, in Patents GB 1,026,978 and GB 1,153,196, incorporated by reference herein, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their acid addition salts.

Examples of the pyrimidine derivatives may include compounds described in German Patent DE 2,359,399, Japanese Patents JP 88-169,571 and JP 91-10659, and Patent Application WO 96/15765, incorporated by reference herein, such as 2,4,5,6-tetraaminopyrimidine, 4-hydroxy-2,5,6-triaminopyrimidine, 2-hydroxy-4,5,6-triaminopyrimidine, 2,4-dihydroxy-5,6- diaminopyrimidine, 2,5,6-triaminopyrimidine; and the pyrazolopyrimidine derivatives such as those mentioned in Patent Application FR-A-2,750,048, incorporated by reference herein, and among which may include pyrazolo [1,5-a]pyrimidine-3,7-diamine, 2-methylpyrazolo[1,5-a] pyrimidine-3,7-diamine; 5-methylpyrazolo[1,5-a] pyrimidine-3,7-diamine; 2,5-dimethylpyrazolo[1,5-a] pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]-pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1, 5-a]pyrimidine, their tautomeric forms, when a tautomeric equilibrium exists and their acid addition salts.

Examples of pyrazole derivatives may include the compounds described in Patents DE 3,843,892, DE 4,133,957, and Patent Applications WO 94/08969, WO 94/08970, FR-A-2,733,749 and DE 195 43 988, incorporated by reference herein, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, and their acid addition salts.

In one embodiment of the invention, the at least one oxidation base can be present in an amount ranging, for example, from 0.0005 to 12% by weight relative to the total weight of the dyeing composition. In another embodiment, the at least one oxidation base can be present in an amount ranging, for example, from 0.005 to 6% by weight relative to the total weight of the dyeing composition.

The dyeing composition in accordance with the invention may also contain, in addition to the at least one coupler chosen from formula (I) above, at least one additional coupler which may be chosen from couplers conventionally used in oxidation dyeing, for example, meta-phenylenediamines, meta-aminophenols, meta-diphenols and heterocyclic couplers such as, indole derivatives, indoline derivatives, pyridine derivatives and pyrazolones, and their acid addition salts.

In one embodiment of the invention, the at least one additional coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, and their acid addition salts.

When present, the at least one additional coupler is present in an amount ranging, for example, from 0.0001 to 10% by weight relative to the total weight of the dyeing composition. In another embodiment of the invention, the at least one additional coupler is present in an amount ranging, for example, from 0.005 to 5% by weight relative to the total weight of the dyeing composition.

In general, the acid addition salts which can be used in the context of the dyeing compositions of the invention (compounds of formula (I), oxidation bases and additional couplers) may be chosen from hydrochlorides, hydrobromides, sulphates, citrates, succinates, tartrates, lactates, and acetates.

The medium suitable for dyeing (or carrier) generally comprises water, and a mixture of water and at least one organic solvent for solubilizing the compounds which might not be sufficiently soluble in water. Examples of the at least one organic solvent may include $C_1$–$C_4$ alkanols such as ethanol and isopropanol, glycerol, glycols, and glycol ethers, such as 2-butoxyethanol, propylene glycol, monomethyl ether of propylene glycol, monoethyl ether and monomethyl ether of diethylene glycol, as well as, aromatic alcohols such as benzyl alcohol and phenoxyethanol, and similar products.

The at least one organic solvent may be present in an amount ranging, for example, from 1 to 40% by weight relative to the total weight of the dyeing composition. In another embodiment, the at least one organic solvent may be present in a amount ranging, for example, from 5 to 30% by weight relative to the total weight of the dyeing composition.

In one embodiment of the invention, the pH of the dyeing composition ranges, for example, from 3 to 12. In another embodiment, the pH ranges, for example, from 5 to 11. The pH may be adjusted to the desired value by means of acidifying or alkalinizing agents normally used in dyeing keratinous fibers.

Examples of acidifying agents may include inorganic and organic acids such as hydrochloric acid, orthophosphoric acid, sulphuric acid, carboxylic acids such as acetic acid, tartaric acid, citric acid, lactic acid and sulphonic acids.

Examples of alkalinizing agents may include aqueous ammonia, alkali metal carbonates, alkanolamines such as mono-, di- and triethanolamines and their derivatives, sodium or potassium hydroxides and the compounds of the following formula (II):

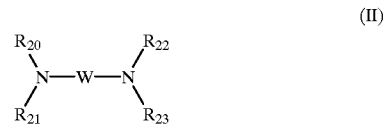

wherein:
W is a propylene residue, optionally substituted with a group chosen from a hydroxyl group and a $C_1$–$C_6$ alkyl group, $R_{20}$, $R_{21}$, $R_{22}$ and $R_{23}$, which are identical or different, are each chosen from a hydrogen atom, and $C_1$–$C_6$ alkyl and $C_1$–$C_6$ hydroxyalkyl groups.

The oxidation dyeing compositions in accordance with the invention may also contain at least one direct dye, which may be helpful in modifying the shades and enriching them with glints.

In one embodiment, the dyeing composition in accordance with the invention, may also contain various adjuvants conventionally used in hair-dyeing compositions, such as, anionic, cationic, nonionic, amphoteric and zwitterionic surfactants and mixtures thereof, anionic, cationic, nonionic, amphoteric and zwitterionic polymers and mixtures thereof, inorganic and organic thickeners, antioxidants, penetrating agents, sequestering agents, perfumes, buffers, dispersing agents, conditioning agents, for example, modified or unmodified, volatile and nonvolatile, silicones, film-forming agents, ceramides, preservatives, and opacifying agents.

Of course persons skilled in the art may choose these possible additional compounds such that the advantageous properties intrinsically attached to the oxidation dyeing composition in accordance with the invention are not substantially impaired by the additions envisaged.

The dyeing composition according to the invention may be provided in various forms, such as, liquids, creams, gels, or in any other form suitable for dyeing keratinous fibers, such as human hair.

One embodiment of the invention is the use of the compounds of formula (I) as defined above as a coupler for the oxidation dyeing of keratinous fibers, for example, human keratinous fibers such as hair.

Another embodiment of the invention is a method of oxidation dyeing keratinous fibers, for example, human keratinous fibers such as hair, using the dyeing composition as defined above.

According to this method, at least one dyeing composition, as defined above, is applied to the fibers, the color being developed at acidic, neutral or alkaline pH with the aid of an oxidizing agent which (1) may be added just at the time of use to the dyeing composition, or (2) may be present in an oxidizing composition applied simultaneously or sequentially.

In one embodiment of the dyeing method, the dyeing composition described above may be mixed, at the time of use, with an oxidizing composition comprising, in a medium suitable for dyeing, at least one oxidizing agent present in a sufficient quantity to develop a color. The mixture obtained may then be applied to the keratinous fibers and allowed to act for 3 to 50 minutes after which they may be rinsed, washed with shampoo, rinsed again and dried.

In another embodiment, the dyeing composition described above may be mixed, at the time of use, with an oxidizing composition comprising, in a medium suitable for dyeing, at least one oxidizing agent present in a sufficient quantity to develop a color. The mixture obtained may then be applied to the keratinous fibers and allowed to act for 5 to 30 minutes after which they may be rinsed, washed with shampoo, rinsed again and dried.

The oxidizing agent may be chosen from the oxidizing agents conventionally used for the oxidation dyeing of keratinous fibers, such as hydrogen peroxide, urea peroxide, alkali metal bromates, persalts, such as perborates and persulphates, peracids, and enzymes such as peroxidases, laccases, tyrosinases and oxidoreductases. Examples of the enzymes may include pyranose oxidases, glucose oxidases, glycerol oxidases, lactate oxidases, pyruvate oxidases and uricases.

The pH of the oxidizing composition containing the oxidizing agent as defined above may be such that after mixing with the dyeing composition, the pH of the resulting composition applied to the keratinous fibers ranges, for example, from 3 to 12. In another embodiment of the invention, the pH of the resulting composition applied to the keratinous fibers ranges, for example, from 5 to 11. The pH may be adjusted to the desired value by means of acidifying and alkalinizing agents normally used in dyeing keratinous fibers and as defined above.

The oxidizing composition as defined above may also comprise various adjuvants conventionally used in hair-dyeing compositions and as defined above.

The composition finally applied to the keratinous fibers, may be provided in various forms, such as liquids, creams, gels, and any other form suitable for dyeing keratinous fibers, such as human hair.

Another embodiment of the invention is chosen from a multicompartment device, dyeing "kit" and any other multicompartment packaging system wherein a first compartment comprises the dyeing composition as defined above and a second compartment comprises the oxidizing composition as defined above. These devices may be equipped with a means to deliver the desired mixture to the hair, such as the devices described in Patent FR-2,586,913, which is incorporated by reference herein.

Unless otherwise indicated, all numbers expressing quantities of ingredients, properties such as molecular weight, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The following examples are intended to illustrate the invention without in anyway limiting the scope thereof.

EXAMPLES OF DYEING

Examples 1 to 5 of Dyeing in Alkaline Medium

Table 1 shows the prepared dyeing compositions (contents in grams):

TABLE 1

| EXAMPLE | 1 | 2 | 3 | 4 | 5 |
|---|---|---|---|---|---|
| Para-phenylenediamine (oxidation base) | 0.72 | — | — | -1 | — |
| Para-aminophenol (oxidation base) | — | 0.73 | — | — | — |
| 4,5-Diamino-1-ethyl-3-methyl-pyrazole.2HCl (oxidation base) | — | — | 1.42 | — | — |
| Pyrazolo[1,5-a]pyrimidine-3,7-diamino.2HCl (oxidation base) | — | — | — | 1.48 | — |
| N,N-Bishydroxyethyl-para-phenylenediamine, sulphate (oxidation base) | — | — | — | — | 1.96 |
| (2-Hydroxy-4-aminophenyl)carbamic acid ethyl ester (compound of formula (I)) | 1.31 | 1.31 | 1.31 | 1.31 | 1.31 |
| Common dye carrier | (*) | (*) | (*) | (*) | (*) |
| Demineralized water qs | 100 g | 100 g | 100 g | 100 g | 100 g |

(*) Common dye carrier

The common dye carrier used in Examples 1–5 of the dye compositions described in Table 1 is:

| | |
|---|---|
| Polyglycerolated oleyl alcohol containing 2 mol of glycerol | 4.0 g |
| Polyglycerolated oleyl alcohol containing 4 mol of glycerol, containing 78% of active substances (AS) | 5.69 g AS |
| Oleic acid | 3.0 g |
| Oleylamine containing 2 mol of ethylene oxide, sold under the trade name ETHOMEEN O12 by the company AKZO | 7.0 g |
| Diethylaminopropyl laurylamino succinamate, sodium salt, containing 55% AS | 3.0 g AS |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite as an aqueous solution containing 35% AS | 0.455 g AS |
| Ammonium acetate | 0.8 g |
| Antioxidant, sequestrant | qs |
| Perfume, preservative | qs |
| Aqueous ammonia containing 20% $NH_3$ | 10.2 g |

At the time of use, each dyeing composition was mixed with an equal quantity of an oxidizing composition comprising a solution of hydrogen peroxide at 20 volumes (6% by weight) and having a pH of about 3.

Each mixture obtained had a pH of about 9.5 and was applied for 30 minutes to locks of natural grey hair which was 90% white. The locks of hair were then rinsed, washed with a standard shampoo and then dried.

The locks of hair were dyed in the shades which are presented in Table 2.

TABLE 2

| EXAMPLE | SHADE ON NATURAL HAIR |
|---|---|
| 1 | Violet mahogany |
| 2 | Golden coppery blond |
| 3 | Red iridescent blond |
| 4 | Golden coppery blond |
| 5 | Violet blue |

Examples 6 to 12 of Dyeing in an Alkaline Medium

Table 3 illustrate the dyeing compositions of Examples 6 to 12 (contents in grams):

TABLE 3

| | EXAMPLE | | | | | | |
|---|---|---|---|---|---|---|---|
| | 6 | 7 | 8 | 9 | 10 | 11 | 12 |
| Para-phenylenediamine (oxidation base) | 0.72 | — | 0.72 | 0.72 | — | — | — |
| 4,5-Diamino-1-ethyl-3-methyl-pyrazole.2HCl (oxidation base) | — | 1.42 | — | — | 1.42 | — | 1.42 |
| Pyrazolo[1,5-a]pyrimidine-3,7-diamino.2HCl (oxidation base) | — | — | — | — | — | 1.48 | — |
| (2-Hydroxy-3,5-dichloro-4-methyl-phenyl)carbamic acid 2-chloroethyl ester (compound of formula (I)) | 1.98 | — | — | — | — | — | — |

TABLE 3-continued

| | EXAMPLE | | | | | | |
|---|---|---|---|---|---|---|---|
| | 6 | 7 | 8 | 9 | 10 | 11 | 12 |
| (2-Hydroxy-4-amino-5-methoxyphenyl) carbamic acid methyl ester (compound of formula (I)) | — | 1.66 | — | — | — | — | — |
| (2-Hydroxy-3,5-dichloro-4-methyl-phenyl)carbamic acid ethyl ester (compound of formula (I)) | — | — | 1.76 | — | — | — | — |
| 3-(2-Hydroxy-4-aminophenyl)-1-benzylurea (compound of formula (I)) | — | — | — | 1.71 | — | — | — |
| 3-(2-Hydroxy-4-aminophenyl)-1-ethyl-urea (compound of formula (I)) | — | — | — | — | 1.30 | — | — |
| 3-(2-Hydroxy-4-aminophenyl)-1-(2-hydroxyethyl) urea (compound of formula (I)) | — | — | — | — | — | 1.41 | — |
| 3-(2-Hydroxy-4-aminophenyl)-1,1-dimethylurea hydrochloride (compound of formula (I)) | — | — | — | — | — | — | 1.54 |
| Common dye carrier | (*) | (*) | (*) | (*) | (*) | (*) | (*) |
| Demineralized water qs | 100 | 100 | 100 | 100 | 100 | 100 | 100 |

(*)Common dye carrier is identical to that used for Examples 1 to 5 above.

At the time of use, each dyeing composition was mixed with an equal quantity of an oxidizing composition comprising a solution of hydrogen peroxide at 20 volumes (6% by weight) and having a pH of about 3.

Each mixture obtained had a pH of about 9.5 and was applied for 30 minutes to locks of natural grey hair which was 90% white. The locks of hair were then rinsed, washed with a standard shampoo and then dried.

The locks of hair were dyed in the shades which are presented in the table 4.

TABLE 4

| EXAMPLE | SHADE ON NATURAL HAIR |
|---|---|
| 6 | Slightly iridescent ash dark blond |
| 7 | Iridescent dark purple |
| 8 | Slightly violet ash dark blond |
| 9 | Ash blond |
| 10 | Red iridescent blond |
| 11 | Slightly iridescent coppery blond |
| 12 | Red iridescent blond |

What is claimed is:

1. A composition for oxidation dyeing keratinous fibers comprising, in a medium suitable for dyeing:

(a) at least one oxidation base; and (b) at least one coupler chosen from compounds of formula (I) and acid addition salts thereof:

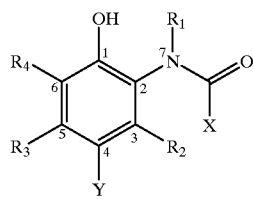
(I)

wherein:
R₁ is chosen from a hydrogen atom, linear and branched, saturated and unsaturated groups comprising from 1–15 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the provisos that:
  (i) said R₁ does not comprise a group chosen from a peroxide group, a diazo group, a nitro group, and a nitroso group, and
  (ii) said $SO_2$ group is not directly linked to the nitrogen at the 7-position of formula (I);
X is chosen from groups $OR_5$ and $NR_6R_7$, wherein
  R₅ is chosen from linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
    (i) said R₅ does not comprise a group chosen from a peroxide group, a diazo group, a nitro group, and a nitroso group;
  R₆ and R₇, which are identical or different, are each chosen from a hydrogen atom, linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
    (i) both said R₆ and R₇ do not comprise a group chosen from a peroxide group, a diazo group, a nitro group, and a nitroso group, and
  said R₆ and R₇ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R, wherein
    R is chosen from linear, branched, saturated, and unsaturated, $C_1$–$C_6$ alkyl groups, optionally substituted with at least one halogen atom, wherein at least one carbon atom is optionally replaced by a unit chosen from an oxygen atom, a nitrogen atom, a sulfur atom, and a $SO_2$ group, and at least one branch of said branched $C_1$–$C_6$ alkyl group optionally forms at least one saturated or unsaturated 3- to 6-membered ring; with the proviso that:
      (i) said R does not comprise a group chosen from a peroxide group, a diazo group, a nitro group, and a nitroso group;
wherein
  said R₁ and said R₅ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
    (i) said R does not comprise a group chosen from a peroxide group, a diazo group, a nitro group, and a nitroso group; and
  said R₁ and said R₆ optionally form a ring, chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
    (i) said R does not comprise a group chosen from a peroxide group, a diazo group, a nitro group, and a nitroso group;
R₂, R₃, and R₄, which are identical or different, are each chosen from a hydrogen atom, a halogen atom, and linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally form at least one 3- to 7-membered ring comprising at least one carbon atom, with the provisos that:
  (i) said R₂, R₃ and R₄ do not comprise a group chosen from a peroxide group, a diazo group, a nitro group, and a nitroso group;
  (ii) said R₄ is chosen from a group other than a hydroxyl group, a thio group, an amino group, and a substituted or unsubstituted sulphonylamino group; and
  (iii) said R₂, R₃ and R₄ are not directly linked to the benzene ring of formula (I) by a —NH—NH—;
wherein
  said R₁ and said R₂ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
    (i) said R does not comprise a group chosen from a peroxide group, a diazo group, a nitro group, and a nitroso group;
wherein
  said R₂ and said R₅ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
    (i) said R does not comprise a group chosen from a peroxide group, a diazo group, a nitro group, and a nitroso group; and (ii) when said $R_2$ and said $R_5$ form a saturated ring comprising 5- to 7-members, said $R_5$ optionally is a bond;

wherein said $R_2$ and said $R_6$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_6$ form a saturated ring comprising 5- to 7-members, said $R_6$ optionally is a bond;

Y is chosen from:
a hydrogen atom;
a halogen atom;
a group chosen from —$OR_8$, —$SR_8$, and —NH—$SO_2R_8$, wherein
$R_8$ is chosen from:
linear and branched $C_1$–$C_8$ alkyl groups, optionally substituted with at least one group chosen from a halogen atom, a hydroxyl group, $C_1$–$C_4$ alkoxy groups, an amino group, amino($C_1$–$C_4$ alkyl) groups, a carboxyl group, and $C_1$–$C_4$ alkoxycarbonyl groups, wherein at least one branch of said branched $C_1$–$C_8$ alkyl groups optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
a benzyl group, optionally substituted with one or two oxy groups, with the proviso that:
(i) when $R_2$ is a hydroxyl group, Y is not a —NH—$SO_2R_8$ group;

provided that:
(i) when said $R_2$ and said $R_4$ are hydrogen atoms, and when said $R_3$ is chosen from substituted and unsubstituted $C_1$–$C_4$ alkyl groups, X is not a an —$OR_5$ group, wherein $R_5$ is chosen from substituted and unsubstituted $C_1$–$C_4$ alkyl groups;
(ii) when said $R_2$ and said $R_4$ are hydrogen atoms, and when said $R_3$ is chosen from substituted and unsubstituted $C_1$–$C_4$ alkyl groups, X is not a $NR_6R_7$ group; and
(iii) when said $R_2$, said $R_4$, and said Y, are hydrogen atoms, and when said X is a $NR_6R_7$ group, wherein said $R_6$ and $R_7$ are hydrogen atoms, said $R_3$ is not chosen from a fluorine atom, a chlorine atom and a bromine atom.

2. A composition for oxidation dyeing keratinous fibers comprising, in a medium suitable for dyeing:
(a) at least one oxidation base; and
(b) at least one coupler chosen from compounds of formula (I) and acid addition salts thereof:

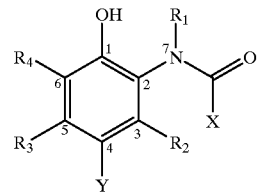

(I)

wherein:
$R_1$ is chosen from:
a hydrogen atom;
a Group $A_1$, wherein said Group $A_1$ is chosen from a hydroxyl group, a dimethylamino group, and linear and branched $C_1$–$C_8$ alkyl groups optionally unsaturated and optionally substituted with at least one unit chosen from:
a group $A_2$, $A_4$, or $A_5$ as defined below;
one or two groups, which are identical or different, chosen from N—($C_1$–$C_3$)alkylamino, N—($C_1$–$C_3$)alkyl-N—($C_1$–$C_3$)alkylamino, ($C_1$–$C_6$)alkoxy, oxo, alkoxycarbonyl, acyloxy, amide, acylamino, ureyl, sulphoxy, sulphonyl, sulphonamido, sulphonylamino, bromo, cyano, amino, and carboxyl; and one or more groups chosen from a hydroxyl group, a fluoro group, and chloro;
a Group $A_2$, wherein said Group $A_2$ is an aromatic group is chosen from a phenyl group, and a naphthyl group, wherein said aromatic group optionally substituted with one to three groups, which are identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl, amino, oxy, and cyano;
a Group $A_3$, wherein said Group $A_3$ is a heteroaromatic group chosen from furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl, wherein said heteroaromatic group is optionally substituted with 1 to 3 groups chosen from linear and branched $C_1$–$C_4$ alkyl groups, a $C_1$–$C_4$ monohydroxyalkyl group, a $C_2$–$C_4$ polyhydroxyalkyl group, a carboxyl group, an alkoxycarbonyl group, an amido group, an amino group, a hydroxyl group, and a halogen atom;
a Group $A_4$ is a group chosen from $C_3$–$C_7$ cycloalkyl and norbornyl; wherein said $C_3$–$C_7$ cycloalkyl group and said norbornyl group further comprise at least one double bond, and wherein said $C_3$–$C_7$ cycloalkyl group and said norbornyl group are optionally substituted with 1 or 2 units chosen from linear and branched $C_1$–$C_4$ alkyl groups, a $C_1$–$C_4$ monohydroxyalkyl group, a $C_2$–$C_4$ polyhydroxyalkyl group, a carboxyl group, an alkoxycarbonyl group, an amido group, an amino group, a hydroxyl group, an oxy group, and a halogen atom; and
a Group $A_5$, wherein said Group $A_5$ is a heterocycle chosen from dihydrofuranyl, tetrahydrofuranyl, butyrolactonyl, dihydrothiophenyl, tetrahydrothiophenyl, tetrahydrothiophenonyl iminothiolane, dihydropyrrolyl, pyrrolidinyl, pyrrolidinonyl, imidazolidinonyl, imidazolidinethionyl, oxazolidinyl, oxazolidinonyl, oxazolanethione, thiazolidinyl, isothiazolonyl, mercaptothiazolinyl, pyrazolidinonyl, iminothiolane, dioxolanyl, pentalactone, dioxanyl, dihydropyridinyl, piperidinyl, pentalactam, morpholinyl, pyrazoli(di)nyl, pyrimi(di)nyl, pyrazinyl, piperazinyl, and azepinyl;

provided that when $R_1$ is chosen from Groups $A_1$, $A_2$, $A_3$, $A_4$, and $A_5$, $R_1$ is optionally attached to the nitrogen at the 7-position by way of a group —(CO)—;

X is chosen from groups $OR_5$ and $NR_6R_7$, wherein
  $R_5$ is chosen from linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
    (i) said $R_5$ does not comprise a group chosen from a peroxide group, a diazo group, a nitro group, and a nitroso group;
  $R_6$ and $R_7$, which are identical or different, are each chosen from a hydrogen atom, linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
    (i) both said $R_6$ and $R_7$ do not comprise a group chosen from a peroxide group, a diazo group, a nitro group, and a nitroso group, and
  said $R_6$ and $R_7$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R, wherein
    R is chosen from linear, branched, saturated, and unsaturated, $C_1$–$C_6$ a alkyl groups, optionally substituted with at least one halogen atom, wherein at least one carbon atom is optionally replaced by a unit chosen from an oxygen atom, a nitrogen atom, a sulfur atom, and a $SO_2$ group, and at least one branch of said branched $C_1$–$C_6$ alkyl group optionally forms at least one saturated or unsaturated 3- to 6-membered ring; with the proviso that:
      (i) said R does not comprise a group chosen from a peroxide group, a diazo group, a nitro group, and a nitroso group;
wherein
  said $R_1$ and said $R_5$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
    (i) said R does not comprise a group chosen from a peroxide group, a diazo group, a nitro group, and a nitroso group; and
  said $R_1$ and said $R_6$ optionally form a ring, chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
    (i) said R does not comprise a group chosen from a peroxide group, a diazo group, a nitro group, and a nitroso group;
  $R_2$, $R_3$, and $R_4$, which are identical or different, are each chosen from a hydrogen atom, a halogen atom, and linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally form at least one 3- to 7-membered ring comprising at least one carbon atom, with the provisos that:
    (i) said $R_2$, $R_3$ and $R_4$ do not comprise a group chosen from a peroxide group, a diazo group, a nitro group, and a nitroso group;
    (ii) said $R_4$ is chosen from a group other than a hydroxyl group, a thio group, an amino group, and a substituted or unsubstituted sulphonylamino group; and
    (iii) said $R_2$, $R_3$ and $R_4$ are not directly linked to the benzene ring of formula (I) by a —NH—NH—;
wherein
  said $R_1$ and said $R_2$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
    (i) said R does not comprise a group chosen from a peroxide group, a diazo group, a nitro group, and a nitroso group;
wherein
  said $R_2$ and said $R_5$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
    (i) said R does not comprise a group chosen from a peroxide group, a diazo group, a nitro group, and a nitroso group; and
    (ii) when said $R_2$ and said $R_5$ form a saturated ring comprising 5- to 7-members, said $R_5$ optionally is a bond;
wherein
  said $R_2$ and said $R_6$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:

(i) said R does not comprise a group chosen from a peroxide group, a diazo group, a nitro group, and a nitroso group; and (ii) when said $R_2$ and said $R_6$ form a saturated ring comprising 5- to 7-members, said $R_6$ optionally is a bond;

Y is chosen from:
a hydrogen atom;
a halogen atom;
a group chosen from —$OR_8$, —$SR_8$, and —NH—$SO_2R_8$, wherein
$R_8$ is chosen from:
linear and branched $C_1$–$C_8$ alkyl groups, optionally substituted with at least one group chosen from a halogen atom, a hydroxyl group, $C_1$–$C_4$ alkoxy groups, an amino group, amino($C_1$–$C_4$ alkyl) groups, a carboxyl group, and $C_1$–$C_4$ alkoxycarbonyl groups, wherein at least one branch of said branched $C_1$–$C_8$ alkyl groups optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
a benzyl group, optionally substituted with one or two oxy groups, with the proviso that:
(i) when $R_2$ is a hydroxyl group, Y is not a —NH—$SO_2R_8$ group;

provided that:
(i) when said $R_2$ and said $R_4$ are hydrogen atoms, and when said $R_3$ is chosen from substituted and unsubstituted $C_1$–$C_4$ alkyl groups, X is not a an —$OR_5$ group, wherein $R_5$ is chosen from substituted and unsubstituted $C_1$–$C_4$ alkyl groups;

(ii) when said $R_2$ and said $R_4$ are hydrogen atoms, and when said $R_3$ is chosen from substituted and unsubstituted $C_1$–$C_4$ alkyl groups, X is not a $NR_6R_7$ group; and (iii) when said $R_2$, said $R_4$, and said Y, are hydrogen atoms, and when said X is a $NR_6R_7$ group, wherein said $R_6$ and $R_7$ are hydrogen atoms, said $R_3$ is not chosen from a fluorine atom, a chlorine atom and a bromine atom.

3. A composition according to claim 1, wherein $R_1$ is chosen from:
a hydrogen atom;
a group chosen from a methyl, ethyl, isopropyl, allyl, phenyl, benzyl, fluorobenzyl, difluorobenzyl, trifluorobenzyl, chlorobenzyl, bromobenzyl, methoxybenzyl, dimethoxybenzyl, (trifluoromethoxy) benzyl, 3,4-methylenedioxybenzyl, 6-chloropiperonyl, 4-methylthiobenzyl, 4-methylsulphonylbenzyl, 4-acetylaminobenzyl, 4-carboxybenzyl, 1-naphthomethyl and 2-naphthomethyl; and
a group chosen from 2-hydroxyethyl, 2-methoxyethyl and 2-ethoxyethyl.

4. A composition according to claim 3, wherein $R_1$ is chosen from a methyl group and a hydrogen atom.

5. A composition for oxidation dyeing keratinous fibers comprising, in a medium suitable for dyeing:
(a) at least one oxidation base; and
(b) at least one coupler chosen from compounds of formula (I) and acid addition salts thereof:

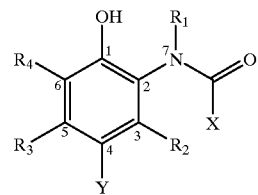

(I)

in which:
$R_1$ is chosen from a hydrogen atom, linear and branched, saturated and unsaturated groups comprising from 1–15 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the provisos that:
(i) said $R_1$ does not comprise a group chosen from a peroxide group, a diazo group, a nitro group, and a nitroso group, and
(ii) said $SO_2$ group is not directly linked to the nitrogen at the 7-position of formula (I);

X is chosen from groups $OR_5$ and $NR_6R_7$, wherein
$R_5$ is chosen from:
a Group $A_1$, wherein said Group $A_1$ is chosen from a hydroxyl group, a dimethylamino group, and linear and branched $C_1$–$C_8$ alkyl groups optionally unsaturated and optionally substituted with at least one unit chosen from:
a Group $A_2$, $A_4$, or $A_5$ as defined below;
one or two groups, which are identical or different, chosen from N—($C_1$–$C_3$) alkylamino, N—($C_1$–$C_3$)alkyl-N—($C_1$–$C_3$) alkylamino, ($C_1$–$C_6$)alkoxy, oxo, alkoxycarbonyl, acyloxy, amide, acylamino, ureyl, sulphoxy, sulphonyl, sulphonamido, sulphonylamino, bromo, cyano, amino, and carboxyl; and
one or more groups chosen from a hydroxyl group, a fluoro group, and chloro group;
a Group $A_2$, wherein said Group $A_2$ is an aromatic group chosen from a phenyl group, and a naphthyl group, wherein said aromatic group is optionally substituted with one to three groups, which are identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl, amino, oxy, and cyano;
a Group $A_3$, wherein said Group $A_3$ is a heteroaromatic group chosen from furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl, wherein said heteroaromatic group is optionally substituted with 1 to 3 groups chosen from linear and branched $C_1$–$C_4$ alkyl groups, a $C_1$–$C_4$ monohydroxyalkyl group, a $C_2$–$C_4$ polyhydroxyalkyl group, a carboxyl group, an alkoxycarbonyl group, an amido group, an amino group, a hydroxyl group, and a halogen atom;

a Group $A_4$ is a group chosen from $C_3$–$C_7$ cycloalkyl and norbornyl; wherein said $C_3$–$C_7$ cycloalkyl group and said norbornyl group further comprise at least one double bond, and wherein said $C_3$–$C_7$ cycloalkyl group and said norbornyl group are optionally substituted with 1 or 2 units chosen from linear and branched $C_1$–$C_4$ alkyl groups, a $C_1$–$C_4$ monohydroxyalkyl group, a $C_2$–$C_4$ polyhydroxyalkyl group, a carboxyl group, an alkoxycarbonyl group, an amido group, an amino group, a hydroxyl group, an oxy group, and a halogen atom; and a Group $A_5$, wherein said Group $A_5$ is a heterocycle chosen from dihydrofuranyl; tetrahydrofuranyl; butyrolactonyl; dihydrothiophenyl; tetrahydrothiophenyl; tetrahydrothiophenonyl; iminothiolane; dihydropyrrolyl; pyrrolidinyl; pyrrolidinonyl; imidazolidinonyl; imidazolidinethionyl; oxazolidinyl; oxazolidinonyl; oxazolanethione; thiazolidinyl; isothiazolonyl; mercaptothiazolinyl; pyrazolidinonyl; iminothiolane; dioxolanyl; pentalactone; dioxanyl; dihydropyridinyl; piperidinyl; pentalactam; morpholinyl; pyrazoli(di)nyl; pyrimi(di)nyl; pyrazinyl; piperazinyl; and azepinyl;

$R_6$ and $R_7$, which are identical or different, are each chosen from a hydrogen atom, linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) both said $R_6$ and $R_7$ do not comprise a group chosen from a peroxide group, a diazo group, a nitro group, and a nitroso group, and said $R_6$ and $R_7$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R, wherein R is chosen from linear, branched, saturated, and unsaturated, $C_1$–$C_6$ alkyl groups, optionally substituted with at least one halogen atom, wherein at least one carbon atom is optionally replaced by a unit chosen from an oxygen atom, a nitrogen atom, a sulfur atom, and a $SO_2$ group, and at least one branch of said branched $C_1$–$C_6$ alkyl group optionally forms at least one saturated or unsaturated 3- to 6-membered ring; with the proviso that:
(i) said R does not comprise a group chosen from a peroxide group, a diazo group, a nitro group, and a nitroso group;

wherein
said $R_1$ and said $R_5$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group; and said $R_1$ and said $R_6$ optionally form a ring, chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

$R_2$, $R_3$, and $R_4$, which are identical or different, are each chosen from a hydrogen atom, a halogen atom, and linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally form at least one 3- to 7-membered ring comprising at least one carbon atom, with the provisos that:
(i) said $R_2$, $R_3$ and $R_4$ do not comprise a group chosen from a peroxide group, a diazo group, a nitro group, and a nitroso group;
(ii) said $R_4$ is chosen from a group other than a hydroxyl group, a thio group, an amino group, and a substituted or unsubstituted sulphonylamino group; and
(iii) said $R_2$, $R_3$ and $R_4$ are not directly linked to the benzene ring of formula (I) by a —NH—NH—;

wherein
said $R_1$ and said $R_2$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

wherein
said $R_2$ and said $R_5$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_5$ form a saturated ring comprising 5- to 7-members, said $R_5$ optionally is a bond;

wherein
said $R_2$ and said $R_6$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:

(i) said R does not comprise a group chosen from a peroxide group, a diazo group, a nitro group, and a nitroso group; and
(ii) when said $R_2$ and said $R_6$ form a saturated ring comprising 5- to 7-members, said $R_6$ optionally is a bond;

Y is chosen from:
a hydrogen atom;
a halogen atom;
a group chosen from —$OR_8$, —$SR_8$, and —NH—$SO_2R_8$, wherein
$R_8$ is chosen from:
linear and branched $C_1$–$C_8$ alkyl groups, optionally substituted with at least one group chosen from a halogen atom, a hydroxyl group, $C_1$–$C_4$ alkoxy groups, an amino group, amino($C_1$–$C_4$ alkyl) groups, a carboxyl group, and $C_1$–$C_4$ alkoxycarbonyl groups, wherein at least one branch of said branched $C_1$–$C_8$ alkyl groups optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
a benzyl group, optionally substituted with one or two oxy groups, with the proviso that:
(i) when $R_2$ is a hydroxyl group, Y is not a —NH—$SO_2R_8$ group;
provided that:
(i) when said $R_2$ and said $R_4$ are hydrogen atoms, and when said $R_3$ is chosen from substituted and unsubstituted $C_1$–$C_4$ alkyl groups, X is not a an —$OR_5$ group, wherein $R_5$ is chosen from substituted and unsubstituted $C_1$–$C_4$ alkyl groups;
(ii) when said $R_2$ and said $R_4$ are hydrogen atoms, and when said $R_3$ is chosen from substituted and unsubstituted $C_1$–$C_4$ alkyl groups, X is not a $NR_6R_7$ group; and
(iii) when said $R_2$, said $R_4$, and said Y, are hydrogen atoms, and when said X is a $NR_6R_7$ group, wherein said $R_6$ and $R_7$ are hydrogen atoms, said $R_3$ is not chosen from a fluorine atom, a chlorine atom and a bromine atom.

6. A composition according to claim 5, wherein $R_5$ is a group chosen from methyl, ethyl, propyl, isopropyl, butyl, isobutyl, tert-butyl, pentyl, isopentyl, neopentyl, hexyl, cyclopropyl, cyclobutyl, cyclopentyl, cyclohexyl, vinyl, 1-methylvinyl, 2-methylvinyl, 2,2-dimethylvinyl, allyl, propargyl, chloromethyl, 2-chloroethyl, 2-hydroxyethyl, 2-methoxyethyl, 4-chlorobutyl, phenyl, 4-methylphenyl, 4-ethylphenyl, 4-(trifluoromethyl)phenyl, 4-hydroxyphenyl, 4-methoxyphenyl, 4-ethoxyphenyl, 4-acetoxyphenyl, 4-aminophenyl, 4-fluorophenyl, 4-chlorophenyl, 4-bromophenyl, naphth-1-yl, naphth-2-yl, and benzyl.

7. A composition according to claim 6, wherein $R_5$ is a group chosen from methyl, ethyl, propyl, isopropyl, butyl, isobutyl, 2-hydroxyethyl, 2-methoxyethyl, allyl, phenyl, benzyl, cyclopentyl, and cyclohexyl.

8. A composition according to claim 1, wherein $R_1$ and $R_5$ form a ring, said ring being chosen from 2-oxazolidon-1-yl, 4-methyloxazolidon-1-yl, and 5,5-dimethyloxazoline-2,4-dion-1-yl.

9. A composition for oxidation dyeing keratinous fibers comprising, in a medium suitable for dyeing:

(a) at least one oxidation base; and
(b) at least one coupler chosen from compounds of formula (I) and acid addition salts thereof:

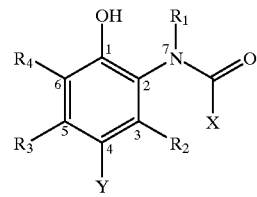

(I)

in which:
$R_1$ is chosen from a hydrogen atom, linear and branched, saturated and unsaturated groups comprising from 1–15 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the provisos that:
(i) said $R_1$ does not comprise a group chosen from a peroxide group, a diazo group, a nitro group, and a nitroso group, and
(ii) said $SO_2$ group is not directly linked to the nitrogen at the 7-position of formula (I);
X is chosen from groups $OR_5$ and $NR_6R_7$, wherein
$R_5$ is chosen from linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) said $R_5$ does not comprise a group chosen from a peroxide group, a diazo group, a nitro group, and a nitroso group;
$R_6$ and $R_7$, which are identical or different, are each chosen from:
a hydrogen atom,
a Group $A_1$, wherein said Group $A_1$ is chosen from a hydroxyl group, a dimethylamino group, and linear and branched $C_1$–$C_8$ alkyl groups optionally unsaturated and optionally substituted with at least one unit chosen from:
a Group $A_2$, $A_4$ or $A_5$ as defined below;
one or two groups, which are identical or different, chosen from N—($C_1$–$C_3$)alkylamino, N—($C_1$–$C_3$)alkyl-N—($C_1$–$C_3$)alkylamino ($C_1$–$C_6$)alkoxy, oxo, alkoxycarbonyl, acyloxy, amide, acylamino, ureyl, sulphoxy, sulphonyl, sulphonamido, sulphonylamino, bromo, cyano, amino, and carboxyl; and
one or more groups chosen from a hydroxyl group, a fluoro group, and chloro group;
a Group $A_2$, wherein said Group $A_2$ is an aromatic group chosen from a phenyl group, and a naphthyl group, wherein said aromatic group is optionally substituted with one to three groups, which are identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl, amino, oxy, and cyano;

a Group $A_3$, wherein said Group $A_3$ is a heteroaromatic group chosen from furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl, wherein said heteroaromatic group is optionally substituted with 1 to 3 groups chosen from linear and branched $C_1$–$C_4$ alkyl groups, a $C_1$–$C_4$ monohydroxyalkyl group, a $C_2$–$C_4$ polyhydroxyalkyl group, a carboxyl group, an alkoxycarbonyl group, an amido group, an amino group, a hydroxyl group, and a halogen atom;

a Group $A_4$ is a group chosen from $C_3$–$C_7$ cycloalkyl and norbornyl; wherein said $C_3$–$C_7$ cycloalkyl group and said norbornyl group further comprise at least one double bond, and wherein said $C_3$–$C_7$ cycloalkyl group and said norbornyl group are optionally substituted with 1 or 2 units chosen from linear and branched $C_1$–$C_4$ alkyl groups, a $C_1$–$C_4$ monohydroxyalkyl group, a $C_2$–$C_4$ polyhydroxyalkyl group, a carboxyl group, an alkoxycarbonyl group, an amido group, an amino group, a hydroxyl group, an oxy group, and a halogen atom; and a Group $A_5$, wherein said Group $A_5$ is a heterocycle chosen from dihydrofuranyl; tetrahydrofuranyl; butyrolactonyl; dihydrothiophenyl; tetrahydrothiophenyl; tetrahydrothiophenonyl; iminothiolane; dihydropyrrolyl; pyrrolidinyl; pyrrolidinonyl; imidazolidinonyl; imidazolidinethionyl; oxazolidinyl; oxazolidinonyl; oxazolanethione; thiazolidinyl; isothiazolonyl; mercaptothiazolinyl; pyrazolidinonyl; iminothiolane; dioxolanyl; pentalactone; dioxanyl; dihydropyridinyl; piperidinyl; pentalactam; morpholinyl; pyrazoli(di)nyl; pyrimi(di)nyl; pyrazinyl; piperazinyl; and azepinyl;

wherein said $R_1$ and said $R_5$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group; and said $R_1$ and said $R_6$ optionally form a ring, chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

$R_2$, $R_3$, and $R_4$, which are identical or different, are each chosen from a hydrogen atom, a halogen atom, and linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally form at least one 3- to 7-membered ring comprising at least one carbon atom, with the provisos that:
(i) said $R_2$, $R_3$ and $R_4$ do not comprise a group chosen from a peroxide group, a diazo group, a nitro group, and a nitroso group;
(ii) said $R_4$ is chosen from a group other than a hydroxyl group, a thio group, an amino group, and a substituted or unsubstituted sulphonylamino group; and
(iii) said $R_2$, $R_3$ and $R_4$ are not directly linked to the benzene ring of formula (I) by a —NH—NH—;

wherein said $R_1$ and said $R_2$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

wherein said $R_2$ and said $R_5$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_5$ form a saturated ring comprising 5- to 7-members, said $R_5$ optionally is a bond;

wherein said $R_2$ and said $R_6$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_6$ form a saturated ring comprising 5- to 7-members, said $R_6$ optionally is a bond;

Y is chosen from:
a hydrogen atom;
a halogen atom;
a group chosen from —$OR_8$, —$SR_8$, and —NH—$SO_2R_8$, wherein
$R_8$ is chosen from:
linear and branched $C_1$–$C_8$ alkyl groups, optionally substituted with at least one group chosen from a halogen atom, a hydroxyl group, $C_1$–$C_4$ alkoxy groups, an amino group, amino($C_1$–$C_4$ alkyl) groups, a carboxyl group, and $C_1$–$C_4$ alkoxycarbonyl groups, wherein at least one branch of said branched $C_1$–$C_8$ alkyl groups optionally forms at least one 3- to 6-membered ring;

a phenyl group, optionally substituted with one or
two groups chosen from $C_1$–$C_4$ alkyl groups, a
trifluoromethyl group, a carboxyl group,
$C_1$–$C_4$ alkoxycarbonyl groups, a halogen atom,
a hydroxyl group, $C_1$–$C_4$ alkoxy groups, an
amino group and amino($C_1$–$C_4$ alkyl) groups;
and
a benzyl group, optionally substituted with one or
two oxy groups, with the proviso that:
(i) when $R_2$ is a hydroxyl group, Y is not a
—NH—$SO_2R_8$ group;
provided that:
(i) when said $R_2$ and said $R_4$ are hydrogen atoms, and
when said $R_3$ is chosen from substituted and unsubstituted $C_1$–$C_4$ alkyl groups, X is not a an —$OR_5$ group, wherein $R_5$ is chosen from substituted and unsubstituted $C_1$–$C_4$ alkyl groups;
(ii) when said $R_2$ and said $R_4$ are hydrogen atoms, and when said $R_3$ is chosen from substituted and unsubstituted $C_1$–$C_4$ alkyl groups, X is not a $NR_6R_7$ group; and
(iii) when said $R_2$, said $R_4$, and said Y, are hydrogen atoms, and when said X is a $NR_6R_7$ group, wherein said $R_6$ and $R_7$ are hydrogen atoms, said $R_3$ is not chosen from a fluorine atom, a chlorine atom and a bromine atom.

10. A composition according to claim 1, wherein $R_6$ and $R_7$, which are identical or different, are each chosen from:
a hydrogen atom; and
a group chosen from methyl, ethyl, propyl, isopropyl, butyl, isobutyl, tert-butyl, pentyl, isopentyl, neopentyl, hexyl, cyclopentyl, cyclohexyl, allyl, propargyl, 2-chloroethyl, 2-hydroxyethyl, 2-methoxyethyl, 3-chloropropyl, 3-hydroxypropyl, 2,3-dihydroxypropyl carboxymethyl, phenyl, fluorophenyl, (trifluoromethyl) phenyl, chlorophenyl, bromophenyl, methylphenyl, 4-acetylphenyl, methoxyphenyl, (trifluoromethoxy) phenyl, naphth-1-yl, benzyl, phenethyl and pyrid-3-yl.

11. A composition according to claim 10, wherein $R_6$ and $R_7$, which are identical or different, are each chosen from a hydrogen atom, a methyl group, an ethyl group, a propyl group, an isopropyl group, a butyl group, an isobutyl group, an allyl group, a 2-hydroxyethyl group, a 2-methoxyethyl group, a 3-hydroxypropyl group, a 2,3-dihydroxypropyl group, a benzyl group, a cyclopentyl group, and cyclohexyl group.

12. A composition according to claim 1, wherein $R_6$ and $R_7$ from a ring, said ring being chosen from pyrrolidin-1-yl, 3-hydroxypyrrolidin-1-yl, 3,4-dihydroxypyrrolidin-1-yl, piperidin-1-yl, 3-hydroxypiperidin-1-yl, 4-hydroxypiperidin-1-yl, 4-morpholin-1-yl, piperazin-1-yl, 4-methylpiperazin-1-yl, and 4-(2-hydroxyethyl)piperazin-1-yl.

13. A composition according to claim 1, wherein $R_1$ and $R_6$ from a ring, said ring being chosen from imidazolidin-2-on-1-yl and tetrahydropyrimidin-2-on-1-yl.

14. A composition for oxidation dyeing keratinous fibers comprising, in a medium suitable for dyeing:
(a) at least one oxidation base; and
(b) at least one coupler chosen from compounds of formula (I) and acid addition salts thereof:

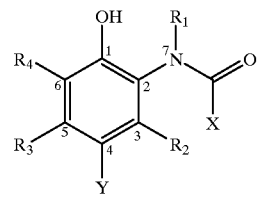

(I)

wherein:
$R_1$ is chosen from a hydrogen atom, linear and branched, saturated and unsaturated groups comprising from 1–15 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the provisos that:
(i) said $R_1$ does not comprise a group chosen from a peroxide group, a diazo group, a nitro group, and a nitroso group, and
(ii) said $SO_2$ group is not directly linked to the nitrogen at the 7-position of formula (I);
X is chosen from groups $OR_5$ and $NR_6R_7$, wherein
$R_5$ is chosen from linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) said $R_5$ does not comprise a group chosen from a peroxide group, a diazo group, a nitro group, and a nitroso group;
$R_6$ and $R_7$, which are identical or different, are each chosen from a hydrogen atom, linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) both said $R_6$ and $R_7$ do not comprise a group chosen from a peroxide group, a diazo group, a nitro group, and a nitroso group, and
said $R_6$ and $R_7$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R, wherein
R is chosen from linear, branched, saturated, and unsaturated, $C_1$–$C_6$ alkyl groups, optionally substituted with at least one halogen atom, wherein at least one carbon atom is optionally replaced by a unit chosen from an oxygen atom, a nitrogen atom, a sulfur atom, and a $SO_2$ group, and at least one branch of said branched $C_1$–$C_6$ alkyl group optionally forms at least one saturated or unsaturated 3- to 6-membered ring; with the proviso that:
  (i) said R does not comprise a group chosen from a peroxide group, a diazo group, a nitro group, and a nitroso group;

wherein
said $R_1$ and said $R_5$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
  (i) said R does not comprise a group chosen from a peroxide group, a diazo group, a nitro group, and a nitroso group; and said $R_1$ and said $R_6$ optionally form a ring, chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
  (i) said R does not comprise a group chosen from a peroxide group, a diazo group, a nitro group, and a nitroso group;

$R_2$, and $R_3$ which are identical or different, are each chosen from:
a hydrogen atom;
a halogen atom;
a hydroxyl group;
an amino group;
a group chosen from Group $A_1$, Group $A_4$, and Group $A_5$, as defined below;
a group chosen from Group $A_1$, Group $A_2$, Group $A_3$, Group $A_4$ and Group $A_5$, as defined below, wherein said groups are attached to the phenolic nucleus in formula (I) by way of a group chosen from an oxygen atom, and a group chosen from —NH—, —Nalkyl($C_1$–$C_3$)—, —O(CO)—, —NH(CO)—, —Nalkyl($C_1$–$C_3$)(CO)—, —NH[C=NH]—, —NH(CO)NH—, —NH(CO)Nalkyl($C_1$–$C_3$)—, —NH(CO)O—, —NHSO$_2$—, —NHSO$_2$NH— and —NHSO$_2$Nalkyl($C_1$–$C_3$)—;

wherein:
said Group $A_1$ is chosen from a hydroxyl group, a dimethylamino group, and linear and branched $C_1$–$C_8$ alkyl groups optionally unsaturated and optionally substituted with at least one unit chosen from:
a Group $A_2$, $A_4$, or $A_5$ as defined below;
one or two groups, which are identical or different, chosen from N—($C_1$–$C_3$)alkylamino, N—($C_1$–$C_3$) alkyl-N—($C_1$–$C_3$)alkylamino, ($C_1$–$C_6$)alkoxy, oxo, alkoxycarbonyl, acyloxy, amide, acylamino, ureyl, sulphoxy, sulphonyl, sulphonamido, sulphonylamino, bromo, cyano, amino, and carboxyl; and
one or more groups chosen from a hydroxyl group, a fluoro group, and chloro group;
said Group $A_2$ is an aromatic group chosen from a phenyl group, and a naphthyl group, wherein said aromatic group is optionally substituted with one to three groups, which are identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl, amino, oxy, and cyano;

said Group $A_3$, is a heteroaromatic group chosen from furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl, wherein said heteroaromatic group is optionally substituted with 1 to 3 groups chosen from linear and branched $C_1$–$C_4$ alkyl groups, a $C_1$–$C_4$ monohydroxyalkyl group, a $C_2$–$C_4$ polyhydroxyalkyl group, a carboxyl group, an alkoxycarbonyl group, an amido group, an amino group, a hydroxyl group, and a halogen atom;

said Group $A_4$ is chosen from $C_3$–$C_7$ cycloalkyl and norbornyl; wherein said $C_3$–$C_7$ cycloalkyl group and said norbornyl group further comprise at least one double bond, and wherein said $C_3$–$C_7$ cycloalkyl group and said norbornyl group are optionally substituted with 1 or 2 units chosen from linear and branched $C_1$–$C_4$ alkyl groups, a $C_1$–$C_4$ monohydroxyalkyl group, a $C_2$–$C_4$ polyhydroxyalkyl group, a carboxyl group, an alkoxycarbonyl group, an amido group, an amino group, a hydroxyl group, an oxy group, and a halogen atom; and said Group $A_5$ is a heterocycle chosen from dihydrofuranyl; tetrahydrofuranyl; butyrolactonyl; dihydrothiophenyl; tetrahydrothiophenyl; tetrahydrothiophenonyl; iminothiolane; dihydropyrrolyl; pyrrolidinyl; pyrrolidinonyl; imidazolidinonyl; imidazolidinethionyl; oxazolidinyl; oxazolidinonyl; oxazolanethione; thiazolidinyl; isothiazolonyl; mercaptothiazolinyl; pyrazolidinonyl; iminothiolane; dioxolanyl; pentalactone; dioxanyl; dihydropyridinyl; piperidinyl; pentalactam; morpholinyl; pyrazoli(di)nyl; pyrimi(di)nyl; pyrazinyl; piperazinyl; and azepinyl;

$R_4$ is chosen from a hydrogen atom, a halogen atom, and linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally form at least one 3- to 7-membered ring comprising at least one carbon atom, with the provisos that:
  (i) said $R_4$ does not comprise a group chosen from a peroxide group, a diazo group, a nitro group, and a nitroso group;
  (ii) said $R_4$ is chosen from a group other than a hydroxyl group, a thio group, an amino group, and a substituted or unsubstituted sulphonylamino group; and
  (iii) said $R_4$ is not directly linked to the benzene ring of formula (I) by a —NH—NH—;

wherein
said $R_1$ and said $R_2$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:

(i) said R does not comprise a group chosen from a peroxide group, a diazo group, a nitro group, and a nitroso group;

wherein said $R_2$ and said $R_5$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
  (i) said R does not comprise a group chosen from a peroxide group, a diazo group, a nitro group, and a nitroso group; and
  (ii) when said $R_2$ and said $R_5$ form a saturated ring comprising 5- to 7-members, said $R_5$ optionally is a bond;

wherein said $R_2$ and said $R_6$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
  (i) said R does not comprise a group chosen from a peroxide group, a diazo group, a nitro group, and a nitroso group; and
  (ii) when said $R_2$ and said $R_6$ form a saturated ring comprising 5- to 7-members, said $R_6$ optionally is a bond;

Y is chosen from:
  a hydrogen atom;
  a halogen atom;
  a group chosen from $-OR_8$, $-SR_8$, and $-NH-SO_2R_8$, wherein
    $R_8$ is chosen from:
      linear and branched $C_1-C_8$ alkyl groups, optionally substituted with at least one group chosen from a halogen atom, a hydroxyl group, $C_1-C_4$ alkoxy groups, an amino group, amino($C_1-C_4$ alkyl) groups, a carboxyl group, and $C_1-C_4$ alkoxycarbonyl groups, wherein at least one branch of said branched $C_1-C_8$ alkyl groups optionally forms at least one 3- to 6-membered ring;
      a phenyl group, optionally substituted with one or two groups chosen from $C_1-C_4$ alkyl groups, a trifluoromethyl group, a carboxyl group, $C_1-C_4$ alkoxycarbonyl groups, a halogen atom, a hydroxyl group, $C_1-C_4$ alkoxy groups, an amino group and amino($C_1-C_4$ alkyl) groups; and
      a benzyl group, optionally substituted with one or two oxy groups, with the proviso that:
        (i) when $R_2$ is a hydroxyl group, Y is not a $-NH-SO_2R_8$ group;

provided that:
  (i) when said $R_2$ and said $R_4$ are hydrogen atoms, and when said $R_3$ is chosen from substituted and unsubstituted $C_1-C_4$ alkyl groups, X is not a an $-OR_5$ group, wherein $R_5$ is chosen from substituted and unsubstituted $C_1-C_4$ alkyl groups;
  (ii) when said $R_2$ and said $R_4$ are hydrogen atoms, and when said $R_3$ is chosen from substituted and unsubstituted $C_1-C_4$ alkyl groups, X is not a $NR_6R_7$ group; and
  (iii) when said $R_2$, said $R_4$, and said Y, are hydrogen atoms, and when said X is a $NR_6R_7$ group, wherein said $R_6$ and $R_7$ are hydrogen atoms, said $R_3$ is not chosen from a fluorine atom, a chlorine atom and a bromine atom.

15. A composition for oxidation dyeing keratinous fibers comprising, in a medium suitable for dyeing:
  (a) at least one oxidation base; and
  (b) at least one coupler chosen from compounds of formula (I) and acid addition salts thereof:

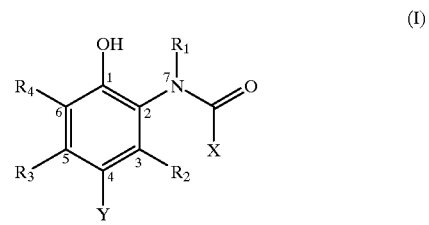

wherein:
  $R_1$ is chosen from a hydrogen atom, linear and branched, saturated and unsaturated groups comprising from 1–15 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the provisos that:
    (i) said $R_1$ does not comprise a group chosen from a peroxide group, a diazo group, a nitro group, and a nitroso group, and
    (ii) said $SO_2$ group is not directly linked to the nitrogen at the 7-position of formula (I);
  $R_2$ is chosen from:
    a hydrogen atom;
    a chlorine atom;
    a group chosen from methyl, hydroxymethyl, methoxymethyl, 2-hydroxyethyl, aminomethyl, methylaminomethyl, hydroxyl, methoxy, acetoxy, amino, methylamino and 2-hydroxyethylamino;
    a group $-NH(CO)R_9$, wherein in $R_9$ is a unit of a group (G1) chosen from:
      methyl, ethyl, propyl, isopropyl, butyl, isobutyl, tert-butyl, pentyl, isopentyl, neopentyl, hexyl; cyclopropyl, cyclobutyl, cyclopentyl, cyclopentylmethyl, 3-cyclopentylpropyl, cyclohexyl, 2-cyclohexylethyl, norborn-2-yl, vinyl, 1-methylvinyl, 2-methylvinyl, 2,2-dimethylvinyl, allyl, 3-butenyl; phenyl, methylphenyl, dimethylphenyl, 2,4,6-trimethylphenyl, 4-ethylphenyl, (trifluoromethyl) phenyl, hydroxyphenyl, methoxyphenyl, ethoxyphenyl, acetoxyphenyl, (trifluoromethoxy) phenyl, aminophenyl,
      4-dimethylaminophenyl, fluorophenyl, difluorophenyl, fluoro(trifluoromethyl)phenyl, chlorophenyl, dichlorophenyl, bromophenyl, naphth-1-yl, naphth-2-yl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl)methyl, (2-naphthyl) methyl; tetrahydrofuran-2-yl, furan-2-yl, 5-methyl-2-(trifluoromethyl)furan-3-yl, 2-methyl-5-phenylfuran-3-yl, thiophen-2-yl, (thiophen-2-yl)methyl, 3-chlorothiophen-2-yl, 2,5-dichlorothiophen-3-yl, benzothiophen-2-yl, 3-chlorobenzothiophen-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, indol-3-ylcarboxyl, pyridinyl, chloropyridinyl, dichloropyridinyl, 5-(bromo)pyridin-3-yl, piperazin-2-yl, quinoxal-2-yl; fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane; methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 2-chloroethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy; amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyridylamino, pyrid-3-ylamino, dimethylamino, 1-pyrrolidinyl, and 4-morpholinyl;

a group —$NHSO_2R_{10}$, wherein $R_{10}$ is a unit of a group (G2), chosen from methyl, trifluoromethyl, ethyl, 2-chloroethyl, propyl, 3-chloropropyl, isopropyl, butyl, thiophen-2-yl, hydroxyl, ethoxy and dimethylamino;

X is chosen from groups $OR_5$ and $NR_6R_7$, wherein $R_5$ is chosen from linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) said $R_5$ does not comprise a group chosen from a peroxide group, a diazo group, a nitro group, and a nitroso group;

$R_6$ and $R_7$, which are identical or different, are each chosen from a hydrogen atom, linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) both said $R_6$ and $R_7$ do not comprise a group chosen from a peroxide group, a diazo group, a nitro group, and a nitroso group, and said $R_6$ and $R_7$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R, wherein R is chosen from linear, branched, saturated, and unsaturated, $C_1$–$C_6$ alkyl groups, optionally substituted with at least one halogen atom, wherein at least one carbon atom is optionally replaced by a unit chosen from an oxygen atom, a nitrogen atom, a sulfur atom, and a $SO_2$ group, and at least one branch of said branched $C_1$–$C_6$ alkyl group optionally forms at least one saturated or unsaturated 3- to 6-membered ring; with the proviso that:
(i) said R does not comprise a group chosen from a peroxide group, a diazo group, a nitro group, and a nitroso group;

wherein said $R_1$ and said $R_5$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group; and said $R_1$ and said $R_6$ optionally form a ring, chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

$R_3$ and $R_4$, which are identical or different, are each chosen from a hydrogen atom, a halogen atom, and linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally form at least one 3- to 7-membered ring comprising at least one carbon atom, with the provisos that:
(i) said $R_3$ and $R_4$ do not comprise a group chosen from a peroxide group, a diazo group, a nitro group, and a nitroso group;
(ii) said $R_4$ is chosen from a group other than a hydroxyl group, a thio group, an amino group, and a substituted or unsubstituted sulphonylamino group; and (iii) said $R_3$ and said $R_4$ are not directly linked to the benzene ring of formula (I) by a —NH—NH—;

wherein said $R_1$ and said $R_2$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

wherein said $R_2$ and said $R_5$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_5$ form a saturated ring comprising 5- to 7-members, said $R_5$ optionally is a bond;

wherein said $R_2$ and said $R_6$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_6$ form a saturated ring comprising 5- to 7-members, said $R_6$ optionally is a bond;

Y is chosen from:
a hydrogen atom;
a halogen atom;
a group chosen from —$OR_8$, —$SR_8$, and —NH—$SO_2R_8$, wherein
$R_8$ is chosen from:
linear and branched $C_1$–$C_8$ alkyl groups, optionally substituted with at least one group chosen from a halogen atom, a hydroxyl group, $C_1$–$C_4$ alkoxy groups, an amino group, amino($C_1$–$C_4$ alkyl) groups, a carboxyl group, and $C_1$–$C_4$ alkoxycarbonyl groups, wherein at least one branch of said branched $C_1$–$C_8$ alkyl groups optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
a benzyl group, optionally substituted with one or two oxy groups, with the proviso that:
(i) when $R_2$ is a hydroxyl group, Y is not a —NH—$SO_2R_8$ group;

provided that:
(i) when said $R_2$ and said $R_4$ are hydrogen atoms, and when said $R_3$ is chosen from substituted and unsubstituted $C_1$–$C_4$ alkyl groups, X is not a an —$OR_5$ group, wherein $R_5$ is chosen from substituted and unsubstituted $C_1$–$C_4$ alkyl groups;
(ii) when said $R_2$ and said $R_4$ are hydrogen atoms, and when said $R_3$ is chosen from substituted and unsubstituted $C_1$–$C_4$ alkyl groups, X is not a $NR_6R_7$ group; and
(iii) when said $R_2$, said $R_4$, and said Y, are hydrogen atoms, and when said X is a $NR_6R_7$ group, wherein said $R_6$ and $R_7$ are hydrogen atoms, said $R_3$ is not chosen from a fluorine atom, a chlorine atom and a bromine atom.

16. A composition for oxidation dyeing keratinous fibers comprising, in a medium suitable for dyeing:
(a) at least one oxidation base; and
(b) at least one coupler chosen from compounds of formula (I) and acid addition salts thereof:

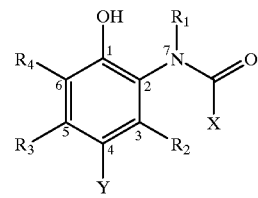

wherein:
$R_1$ is chosen from a hydrogen atom, linear and branched, saturated and unsaturated groups comprising from 1–15 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the provisos that:
(i) said $R_1$ does not comprise a group chosen from a peroxide group, a diazo group, a nitro group, and a nitroso group, and
(ii) said $SO_2$ group is not directly linked to the nitrogen at the 7-position of formula (I);
$R_2$ is chosen from:
a hydrogen atom;
a group chosen from methyl; hydroxymethyl; aminomethyl; hydroxyl; methoxy; amino; and methylamino;
a group chosen from methanesulphonylamino; ethanesulphonylamino; and dimethylaminosulphonylamino; and
a group —NH(CO)$R_{11}$ wherein $R_{11}$ is a unit of a group (G3) chosen from:
methyl, ethyl, propyl, allyl, phenyl, tetrahydrofuran-2-yl, furan-2-yl, thiophen-2-yl, pyridinyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl and 4-morpholinyl;
X is chosen from groups $OR_5$ and $NR_6R_7$, wherein
$R_5$ is chosen from linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) said $R_5$ does not comprise a group chosen from a peroxide group, a diazo group, a nitro group, and a nitroso group;

$R_6$ and $R_7$, which are identical or different, are each chosen from a hydrogen atom, linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) both said $R_6$ and $R_7$ do not comprise a group chosen from a peroxide group, a diazo group, a nitro group, and a nitroso group, and said $R_6$ and $R_7$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R, wherein
R is chosen from linear, branched, saturated, and unsaturated, $C_1$–$C_6$ alkyl groups, optionally substituted with at least one halogen atom, wherein at least one carbon atom is optionally replaced by a unit chosen from an oxygen atom, a nitrogen atom, a sulfur atom, and a $SO_2$ group, and at least one branch of said branched $C_1$–$C_6$ alkyl group optionally forms at least one saturated or unsaturated 3- to 6-membered ring; with the proviso that:
(i) said R does not comprise a group chosen from a peroxide group, a diazo group, a nitro group, and a nitroso group;

wherein
said $R_1$ and said $R_5$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group; and said $R_1$ and said $R_6$ optionally form a ring, chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

$R_3$ and $R_4$, which are identical or different, are each chosen from a hydrogen atom, a halogen atom, and linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally form at least one 3- to 7-membered ring comprising at least one carbon atom, with the provisos that:
(i) said $R_3$ and $R_4$ do not comprise a group chosen from a peroxide group, a diazo group, a nitro group, and a nitroso group;
(ii) said $R_4$ is chosen from a group other than a hydroxyl group, a thio group, an amino group, and a substituted or unsubstituted sulphonylamino group; and
(iii) said $R_3$ and said $R_4$ are not directly linked to the benzene ring of formula (I) by a —NH—NH—;

wherein
said $R_1$ and said $R_2$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

wherein
said $R_2$ and said $R_5$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_5$ form a saturated ring comprising 5- to 7-members, said $R_5$ optionally is a bond;

wherein
said $R_2$ and said $R_6$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_6$ form a saturated ring comprising 5- to 7-members, said $R_6$ optionally is a bond;

Y is chosen from:
a hydrogen atom;
a halogen atom;
a group chosen from —$OR_8$, —$SR_8$, and —NH—$SO_2R_8$, wherein
$R_8$ is chosen from:
linear and branched $C_1$–$C_8$ alkyl groups, optionally substituted with at least one group chosen from a halogen atom, a hydroxyl group, $C_1$–$C_4$ alkoxy groups, an amino group, amino($C_1$–$C_4$ alkyl) groups, a carboxyl group, and $C_1$–$C_4$ alkoxycarbonyl groups, wherein at least one branch of said branched $C_1$–$C_8$ alkyl groups optionally forms at least one 3- to 6-membered ring;

a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and a benzyl group, optionally substituted with one or two oxy groups, with the proviso that:
(i) when $R_2$ is a hydroxyl group, Y is not a —NH—$SO_2R_8$ group;

provided that:
(i) when said $R_2$ and said $R_4$ are hydrogen atoms, and when said $R_3$ is chosen from substituted and unsubstituted $C_1$–$C_4$ alkyl groups, X is not a an —$OR_5$ group, wherein $R_5$ is chosen from substituted and unsubstituted $C_1$–$C_4$ alkyl groups;
(ii) when said $R_2$ and said $R_4$ are hydrogen atoms, and when said $R_3$ is chosen from substituted and unsubstituted $C_1$–$C_4$ alkyl groups, X is not a $NR_6R_7$ group; and
(iii) when said $R_2$, said $R_4$, and said Y, are hydrogen atoms, and when said X is a $NR_6R_7$ group, wherein said $R_6$ and $R_7$ are hydrogen atoms, said $R_3$ is not chosen from a fluorine atom, a chlorine atom and a bromine atom.

17. A composition according to claim 1, wherein $R_1$ and $R_2$ form a ring together with the nitrogen atom at the 7-position of the at least one coupler of formula (I), wherein —$R_1R_2$— is —$CH_2CH_2CH_2$—.

18. A composition according to claim 1, wherein $R_2$ and $R_5$ form a ring, together with the nitrogen atom at the 7-position of the at least one coupler of formula (I), wherein —$R_2R_5$— is chosen from —$CH_2$— and —$C(CH_3)_2$—.

19. A composition according to claim 1, wherein $R_2$ and $R_6$ form a ring, together with the nitrogen atom at the 7-position of the at least one coupler of formula (I), wherein —$R_2R_6$— is chosen from —$CH_2$— and —$C(CH_3)_2$—.

20. A composition for oxidation dyeing keratinous fibers comprising, in a medium suitable for dyeing:
(a) at least one oxidation base; and
(b) at least one coupler chosen from compounds of formula (I) and acid addition salts thereof:

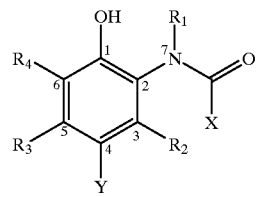

(I)

wherein:
$R_1$ is chosen from a hydrogen atom, linear and branched, saturated and unsaturated groups comprising from 1–15 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the provisos that:
(i) said $R_1$ does not comprise a group chosen from a peroxide group, a diazo group, a nitro group, and a nitroso group, and (ii) said $SO_2$ group is not directly linked to the nitrogen at the 7-position of formula (I);
X is chosen from groups $OR_5$ and $NR_6R_7$, wherein
$R_5$ is chosen from linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) said $R_5$ does not comprise a group chosen from a peroxide group, a diazo group, a nitro group, and a nitroso group;
$R_6$ and $R_7$, which are identical or different, are each chosen from a hydrogen atom, linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) both said $R_6$ and $R_7$ do not comprise a group chosen from a peroxide group, a diazo group, a nitro group, and a nitroso group, and
said $R_6$ and $R_7$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R, wherein
R is chosen from linear, branched, saturated, and unsaturated, $C_1$–$C_6$ alkyl groups, optionally substituted with at least one halogen atom, wherein at least one carbon atom is optionally replaced by a unit chosen from an oxygen atom, a nitrogen atom, a sulfur atom, and a $SO_2$ group, and at least one branch of said branched $C_1$–$C_6$ alkyl group optionally forms at least one saturated or unsaturated 3- to 6-membered ring; with the proviso that:
(i) said R does not comprise a group chosen from a peroxide group, a diazo group, a nitro group, and a nitroso group;
wherein
said $R_1$ and said $R_5$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group; and
said $R_1$ and said $R_6$ optionally form a ring, chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:

(i) said R does not comprise a group chosen from a peroxide group, a diazo group, a nitro group, and a nitroso group;

$R_3$ is chosen from:
- a hydrogen atom;
- a chlorine atom;
- a group chosen from methyl, ethyl, hydroxymethyl, 2-hydroxyethyl, methoxymethyl, aminomethyl, methylaminomethyl, hydroxyl, methoxy, acetoxy, amino, methylamino, 2-hydroxyethylamino, N-piperidino and N-morpholino;
- a group —NH(CO)$R_{12}$, wherein $R_{12}$ is a unit of a group (G1), chosen from
  - methyl, ethyl, propyl, isopropyl, butyl, isobutyl, tert-butyl, pentyl, isopentyl, neopentyl, hexyl; cyclopropyl, cyclobutyl, cyclopentyl, cyclopentylmethyl, 3-cyclopentylpropyl, cyclohexyl, 2-cyclohexylethyl, norborn-2-yl, vinyl, 1-methylvinyl, 2-methylvinyl, 2,2-dimethylvinyl, allyl, 3-butenyl; phenyl, methylphenyl, dimethylphenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, naphth-1-yl, naphth-2-yl, (2-methoxy)naphth-1-yl, benzyl, 4'-methoxybenzyl, 2',5'-dimethoxybenzyl, '3,4'-dimethoxybenzyl, 4'-fluorobenzyl, 4'-chlorobenzyl, phenethyl, 2-phenylvinyl, (1-naphthyl)methyl, (2-naphthyl)methyl; tetrahydrofuran-2-yl, furan-2-yl, 5-methyl-2-(trifluoromethyl)furan-3-yl, 2-methyl-5-phenylfuran-3-yl, thiophen-2-yl, (thiophen-2-yl)methyl, 3-chlorothiophen-2-yl, 2,5-dichlorothiophen-3-yl, benzothiophen-2-yl, 3-chlorobenzothiophen-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, indol-3-ylcarboxyl, pyridinyl, chloropyridinyl, dichloropyridinyl, 5-(bromo)pyridin-3-yl, piperazin-2-yl, quinoxal-2-yl; fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane; methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 2-chloroethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy; amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyridylamino, pyrid-3-ylamino, dimethylamino, 1-pyrrolidinyl and 4-morpholinyl; and
- a group —NHSO$_2$R$_{13}$, wherein R$_{13}$ is a unit of a group (G2), chosen from
  - methyl, trifluoromethyl, ethyl, 2-chloroethyl, propyl, 3-chloropropyl, isopropyl, butyl, thiophen-2-yl, hydroxyl, ethoxy and dimethylamino;

$R_2$ and $R_4$, which are identical or different, are each chosen from a hydrogen atom, a halogen atom, and linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a SO$_2$ group, and at least one branch of said branched groups optionally form at least one 3- to 7-membered ring comprising at least one carbon atom, with the provisos that:
(i) said $R_2$ and $R_4$ do not comprise a group chosen from a peroxide group, a diazo group, a nitro group, and a nitroso group;
(ii) said $R_4$ is chosen from a group other than a hydroxyl group, a thio group, an amino group, and a substituted or unsubstituted sulphonylamino group; and
(iii) said $R_2$ and $R_4$ are not directly linked to the benzene ring of formula (I) by a —NH—NH—;

wherein
said $R_1$ and said $R_2$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

wherein
said $R_2$ and said $R_5$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_5$ form a saturated ring comprising 5- to 7-members, said $R_5$ optionally is a bond;

wherein
said $R_2$ and said $R_6$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_6$ form a saturated ring comprising 5- to 7-members, said $R_6$ optionally is a bond;

Y is chosen from:
a hydrogen atom;
a halogen atom;
a group chosen from —$OR_8$, —$SR_8$, and —NH—$SO_2R_8$, wherein
$R_8$ is chosen from:
linear and branched $C_1$–$C_8$ alkyl groups, optionally substituted with at least one group chosen from a halogen atom, a hydroxyl group, $C_1$–$C_4$ alkoxy groups, an amino group, amino($C_1$–$C_4$ alkyl) groups, a carboxyl group, and $C_1$–$C_4$ alkoxycarbonyl groups, wherein at least one branch of said branched $C_1$–$C_8$ alkyl groups optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
a benzyl group, optionally substituted with one or two oxy groups, with the proviso that:
(i) when $R_2$ is a hydroxyl group, Y is not a —NH—$SO_2R_8$ group;

provided that:
(i) when said $R_2$ and said $R_4$ are hydrogen atoms, and when said $R_3$ is chosen from substituted and unsubstituted $C_1$–$C_4$ alkyl groups, X is not a an —$OR_5$ group, wherein $R_5$ is chosen from substituted and unsubstituted $C_1$–$C_4$ alkyl groups;
(ii) when said $R_2$ and said $R_4$ are hydrogen atoms, and when said $R_3$ is chosen from substituted and unsubstituted $C_1$–$C_4$ alkyl groups, X is not a $NR_6R_7$ group; and
(iii) when said $R_2$, said $R_4$, and said Y, are hydrogen atoms, and when said X is a $NR_6R_7$ group, wherein said $R_6$ and $R_7$ are hydrogen atoms, said $R_3$ is not chosen from a fluorine atom, a chlorine atom and a bromine atom.

21. A composition for oxidation dyeing keratinous fibers comprising, in a medium suitable for dyeing:
(a) at least one oxidation base; and
(b) at least one coupler chosen from compounds of formula (I) and acid addition salts thereof:

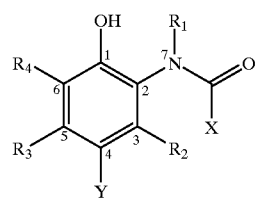

(I)

wherein:
$R_1$ is chosen from a hydrogen atom, linear and branched, saturated and unsaturated groups comprising from 1–15 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the provisos that:
(i) said $R_1$ does not comprise a group chosen from a peroxide group, a diazo group, a nitro group, and a nitroso group, and
(ii) said $SO_2$ group is not directly linked to the nitrogen at the 7-position of formula (I);
X is chosen from groups $OR_5$ and $NR_6R_7$, wherein
$R_5$ is chosen from linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) said $R_5$ does not comprise a group chosen from a peroxide group, a diazo group, a nitro group, and a nitroso group;
$R_6$ and $R_7$, which are identical or different, are each chosen from a hydrogen atom, linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) both said $R_6$ and $R_7$ do not comprise a group chosen from a peroxide group, a diazo group, a nitro group, and a nitroso group, and
said $R_6$ and $R_7$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R, wherein
R is chosen from linear, branched, saturated, and unsaturated, $C_1$–$C_6$ alkyl groups, optionally substituted with at least one halogen atom, wherein at least one carbon atom is optionally replaced by a unit chosen from an oxygen atom, a nitrogen atom, a sulfur atom, and a $SO_2$ group, and at least one branch of said branched $C_1$–$C_6$ alkyl group optionally forms at least one saturated or unsaturated 3- to 6-membered ring; with the proviso that:
(i) said R does not comprise a group chosen from a peroxide group, a diazo group, a nitro group, and a nitroso group;

wherein
said $R_1$ and said $R_5$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group; and said $R_1$ and said $R_6$ optionally form a ring, chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

$R_3$ is chosen from:
a hydrogen atom;
a chlorine atom;
a group chosen from methyl, hydroxymethyl, aminomethyl, hydroxyl, methoxy, amino and methylamino;
a group chosen from methanesulphonylamino; ethanesulphonylamino; and dimethylaminosulphonylamino; and
a group —NH(CO)$R_{14}$ wherein $R_{14}$ is a unit of a group (G3), chosen from:
methyl, ethyl, propyl, allyl, phenyl, tetrahydrofuran-2-yl, furan-2-yl, thiophen-2-yl, pyridinyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl and 4-morpholinyl;

$R_2$ and $R_4$, which are identical or different, are each chosen from a hydrogen atom, a halogen atom, and linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally form at least one 3- to 7-membered ring comprising at least one carbon atom, with the provisos that:
(i) said $R_2$ and said $R_4$ do not comprise a group chosen from a peroxide group, a diazo group, a nitro group, and a nitroso group;
(ii) said $R_4$ is chosen from a group other than a hydroxyl group, a thio group, an amino group, and a substituted or unsubstituted sulphonylamino group; and
(iii) said $R_2$ and said $R_4$ are not directly linked to the benzene ring of formula (I) by a —NH—NH—;
wherein
said $R_1$ and said $R_2$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

wherein
said $R_2$ and said $R_5$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_5$ form a saturated ring comprising 5- to 7-members, said $R_5$ optionally is a bond;

wherein
said $R_2$ and said $R_6$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_6$ form a saturated ring comprising 5- to 7-members, said $R_6$ optionally is a bond;

Y is chosen from:
a hydrogen atom;
a halogen atom;
a group chosen from —$OR_8$, —$SR_8$, and —NH—$SO_2R_8$, wherein
$R_8$ is chosen from:
linear and branched $C_1$–$C_8$ alkyl groups, optionally substituted with at least one group chosen from a halogen atom, a hydroxyl group, $C_1$–$C_4$ alkoxy groups, an amino group, amino($C_1$–$C_4$ alkyl) groups, a carboxyl group, and $C_1$–$C_4$ alkoxycarbonyl groups, wherein at least one branch of said branched $C_1$–$C_8$ alkyl groups optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
a benzyl group, optionally substituted with one or two oxy groups, with the proviso that:
(i) when $R_2$ is a hydroxyl group, Y is not a —NH—$SO_2R_8$ group;
provided that:
(i) when said $R_2$ and said $R_4$ are hydrogen atoms, and when said $R_3$ is chosen from substituted and unsubstituted $C_1$–$C_4$ alkyl groups, X is not a an —$OR_5$ group, wherein $R_5$ is chosen from substituted and unsubstituted $C_1$–$C_4$ alkyl groups;
(ii) when said $R_2$ and said $R_4$ are hydrogen atoms, and when said $R_3$ is chosen from substituted and unsubstituted $C_1$–$C_4$ alkyl groups, X is not a $NR_6R_7$ group; and
(iii) when said $R_2$, said $R_4$, and said Y, are hydrogen atoms, and when said X is a $NR_6R_7$ group, wherein said $R_6$ and $R_7$ are hydrogen atoms, said $R_3$ is not chosen from a fluorine atom, a chlorine atom and a bromine atom.

22. A composition for oxidation dyeing keratinous fibers comprising, in a medium suitable for dyeing:
(a) at least one oxidation base; and
(b) at least one coupler chosen from compounds of formula (I) and acid addition salts thereof:

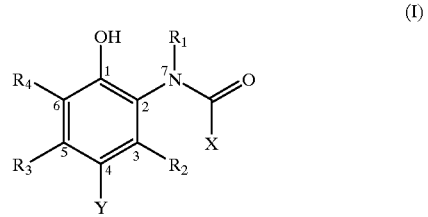

(I)

wherein:
$R_1$ is chosen from a hydrogen atom, linear and branched, saturated and unsaturated groups comprising from 1–15 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the provisos that:
  (i) said $R_1$ does not comprise a group chosen from a peroxide group, a diazo group, a nitro group, and a nitroso group, and
  (ii) said $SO_2$ group is not directly linked to the nitrogen at the 7-position of formula (I);
X is chosen from groups $OR_5$ and $NR_6R_7$, wherein
  $R_5$ is chosen from linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
    (i) said $R_5$ does not comprise a group chosen from a peroxide group, a diazo group, a nitro group, and a nitroso group;
  $R_6$ and $R_7$, which are identical or different, are each chosen from a hydrogen atom, linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
    (i) both said $R_6$ and $R_7$ do not comprise a group chosen from a peroxide group, a diazo group, a nitro group, and a nitroso group, and
  said $R_6$ and $R_7$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R, wherein
    R is chosen from linear, branched, saturated, and unsaturated, $C_1$–$C_6$ alkyl groups, optionally substituted with at least one halogen atom, wherein at least one carbon atom is optionally replaced by a unit chosen from an oxygen atom, a nitrogen atom, a sulfur atom, and a $SO_2$ group, and at least one branch of said branched $C_1$–$C_6$ alkyl group optionally forms at least one saturated or unsaturated 3- to 6-membered ring; with the proviso that:
      (i) said R does not comprise a group chosen from a peroxide group, a diazo group, a nitro group, and a nitroso group;
wherein
  said $R_1$ and said $R_5$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
    (i) said R does not comprise a group chosen from a peroxide group, a diazo group, a nitro group, and a nitroso group; and
  said $R_1$ and said $R_6$ optionally form a ring, chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
    (i) said R does not comprise a group chosen from a peroxide group, a diazo group, a nitro group, and a nitroso group;
  $R_2$ and $R_3$, which are identical or different, are each chosen from a hydrogen atom, a halogen atom, and linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally form at least one 3- to 7-membered ring comprising at least one carbon atom, with the provisos that:
    (i) said $R_2$ and $R_3$ do not comprise a group chosen from a peroxide group, a diazo group, a nitro group, and a nitroso group;
    (iii) said $R_2$ and $R_3$ are not directly linked to the benzene ring of formula (I) by a —NH—NH—;
wherein
  said $R_1$ and said $R_2$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
    (i) said R does not comprise a group chosen from a peroxide group, a diazo group, a nitro group, and a nitroso group;
  $R_4$ is chosen from:
    a hydrogen atom;
    a halogen atom;
    a group chosen from Group $A_1$, Group $A_4$ and Group $A_5$ as defined below;
    a group chosen from Group $A_1$, Group $A_2$, Group $A_3$, Group $A_4$ and Group $A_5$, as defined below, wherein said groups are attached to the phenolic nucleus in formula (I) by way of a group chosen from an oxygen atom; a sulfur atom and a group chosen from —NH—, —Nalkyl($C_1$–$C_3$)—, —O(CO)—, —NH(CO)—, —Nalkyl($C_1$–$C_3$)(CO)—, —NH[C=NH]—, —NH(CO)NH—, —NH(CO)Nalkyl($C_1$–$C_3$)— and —NH(CO)O—;

wherein:

said Group $A_1$ is chosen from a hydroxyl gruop, a dimethylamino group, and linear and branched $C_1$–$C_8$ alkyl groups optionally unsaturated and optionally substituted with at least one unit chosen from:

a Group $A_2$, $A_4$, or $A_5$ as defined below;

one or two groups, which are identical or different, chosen from N—($C_1$–$C_3$)alkylamino, N—($C_1$–$C_3$)alkyl-N—($C_1$–$C_3$)alkylamino, ($C_1$–$C_6$)alkoxy, oxo, alkoxycarbonyl, acyloxy, amide, acylamino, ureyl, sulphoxy, sulphonyl, sulphonamido, sulphonylamino, bromo, cyano, amino, and carboxyl; and one or more groups chosen from a hydroxyl group, a fluoro group, and a chloro group;

said Group $A_2$, is an aromatic group chosen from a phenyl group, and a naphthyl group, wherein said aromatic group is optionally substituted with one to three groups, which are identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl, amino, oxy, and cyano;

said Group $A_3$, is a heteroaromatic group chosen from furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzoimidazolyl, benzoxazolyl, benzothiazolyl, indolyl, indolidinyl, isoindolyl, indazolyl, benzotriazolyl, quinolinyl, benzoimidazolyl and benzopyrimidyl, wherein said heteroaromatic group is optionally substituted with 1 to 3 groups chosen from linear and branched $C_1$–$C_4$ alkyl groups, a $C_1$–$C_4$ monohydroxyalkyl group, a $C_2$–$C_4$ polyhydroxyalkyl group, a carboxyl group, an alkoxycarbonyl group, an amido group, an amino group, a hydroxyl group, and a halogen atom;

said Group $A_4$ is chosen from $C_3$–$C_7$ cycloalkyl and norbornyl; wherein said $C_3$–$C_7$ cycloalkyl group and said norbornyl group further comprise at least one double bond, and wherein said $C_3$–$C_7$ cycloalkyl group and said norbornyl group are optionally substituted with 1 or 2 units chosen from linear and branched $C_1$–$C_4$ alkyl groups, a $C_1$–$C_4$ monohydroxyalkyl group, a $C_2$–$C_4$ polyhydroxyalkyl group, a carboxyl group, an alkoxycarbonyl group, an amido group, an amino group, a hydroxyl group, an oxy group, and a halogen atom; and said Group $A_5$ is a heterocycle chosen from dihydrofuranyl; tetrahydrofuranyl; butyrolactonyl; dihydrothiophenyl; tetrahydrothiophenyl; tetrahydrothiophenonyl; iminothiolane; dihydropyrrolyl; pyrrolidinyl; pyrrolidinonyl; imidazolidinonyl; imidazolidinethionyl; oxazolidinyl; oxazolidinonyl; oxazolanethione; thiazolidinyl; isothiazolonyl; mercaptothiazolinyl; pyrazolidinonyl; iminothiolane; dioxolanyl; pentalactone; dioxanyl; dihydropyridinyl; piperidinyl; pentalactam; morpholinyl; pyrazoli(di)nyl; pyrimi(di)nyl; pyrazinyl; piperazinyl; and azepinyl;

wherein said $R_2$ and said $R_5$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:

(i) said R does not comprise a group chosen from a peroxide group, a diazo group, a nitro group, and a nitroso group; and (ii) when said $R_2$ and said $R_5$ form a saturated ring comprising 5- to 7-members, said $R_5$ optionally is a bond;

wherein said $R_2$ and said $R_6$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:

(i) said R does not comprise a group chosen from a peroxide group, a diazo group, a nitro group, and a nitroso group; and (ii) when said $R_2$ and said $R_6$ form a saturated ring comprising 5- to 7-members, said $R_6$ optionally is a bond;

Y is chosen from:

a hydrogen atom;

a halogen atom;

a group chosen from —$OR_8$, —$SR_8$, and —NH—$SO_2R_8$, wherein $R_8$ is chosen from:

linear and branched $C_1$–$C_8$ alkyl groups, optionally substituted with at least one group chosen from a halogen atom, a hydroxyl group, $C_1$–$C_4$ alkoxy groups, an amino group, amino($C_1$–$C_4$ alkyl) groups, a carboxyl group, and $C_1$–$C_4$ alkoxycarbonyl groups, wherein at least one branch of said branched $C_1$–$C_8$ alkyl groups optionally forms at least one 3- to 6-membered ring;

a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and a benzyl group, optionally substituted with one or two oxy groups, with the proviso that:

(i) when $R_2$ is a hydroxyl group, Y is not a —NH—$SO_2R_8$ group;

provided that:

(i) when said $R_2$ and said $R_4$ are hydrogen atoms, and when said $R_3$ is chosen from substituted and unsubstituted $C_1$–$C_4$ alkyl groups, X is not a an —$OR_5$ group, wherein $R_5$ is chosen from substituted and unsubstituted $C_1$–$C_4$ alkyl groups;

(ii) when said $R_2$ and said $R_4$ are hydrogen atoms, and when said $R_3$ is chosen from substituted and unsubstituted $C_1$–$C_4$ alkyl groups, X is not a $NR_6R_7$ group; and (iii) when said $R_2$, said $R_4$, and said Y, are hydrogen atoms, and when said X is a $NR_6R_7$ group, wherein said $R_6$ and $R_7$ are hydrogen atoms, said $R_3$ is not chosen from a fluorine atom, a chlorine atom and a bromine atom.

23. A composition for oxidation dyeing keratinous fibers comprising, in a medium suitable for dyeing:
(a) at least one oxidation base; and
(b) at least one coupler chosen from compounds of formula (I) and acid addition salts thereof:

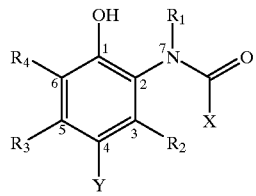

(I)

wherein:
$R_1$ is chosen from a hydrogen atom, linear and branched, saturated and unsaturated groups comprising from 1–15 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the provisos that:
(i) said $R_1$ does not comprise a group chosen from a peroxide group, a diazo group, a nitro group, and a nitroso group, and
(ii) said $SO_2$ group is not directly linked to the nitrogen at the 7-position of formula (I);
X is chosen from groups $OR_5$ and $NR_6R_7$, wherein
$R_5$ is chosen from linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) said $R_5$ does not comprise a group chosen from a peroxide group, a diazo group, a nitro group, and a nitroso group;
$R_6$ and $R_7$, which are identical or different, are each chosen from a hydrogen atom, linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) both said $R_6$ and $R_7$ do not comprise a group chosen from a peroxide group, a diazo group, a nitro group, and a nitroso group, and
said $R_6$ and $R_7$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R, wherein
R is chosen from linear, branched, saturated, and unsaturated, $C_1$–$C_6$ alkyl groups, optionally substituted with at least one halogen atom, wherein at least one carbon atom is optionally replaced by a unit chosen from an oxygen atom, a nitrogen atom, a sulfur atom, and a $SO_2$ group, and at least one branch of said branched $C_1$–$C_6$ alkyl group optionally forms at least one saturated or unsaturated 3- to 6-membered ring; with the proviso that:
(i) said R does not comprise a group chosen from a peroxide group, a diazo group, a nitro group, and a nitroso group;
wherein
said $R_1$ and said $R_5$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group; and
said $R_1$ and said $R_6$ optionally form a ring, chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;
$R_2$ and $R_3$, which are identical or different, are each chosen from a hydrogen atom, a halogen atom, and linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally form at least one 3- to 7-membered ring comprising at least one carbon atom, with the provisos that:
(i) said $R_2$ and said $R_3$ do not comprise a group chosen from a peroxide group, a diazo group, a nitro group, and a nitroso group; and
(ii) said $R_2$ and said $R_3$ are not directly linked to the benzene ring of formula (I) by a —NH—NH—;
$R_4$ is chosen from:
an atom chosen from hydrogen, chlorine, fluorine, and bromine,
a group chosen from methyl, trifluoromethyl, allyl, hydroxymethyl, methoxymethyl, 2-hydroxyethyl, aminomethyl, methylaminomethyl, methoxy, acetoxy and methylamino; and
a group —NH(CO)$R_{15}$ wherein $R_{15}$ is a unit of a group (G1), chosen from
methyl, ethyl, propyl, isopropyl, butyl, isobutyl, tert-butyl, pentyl, isopentyl, neopentyl, hexyl; cyclopropyl, cyclobutyl, cyclopentyl, cyclopentylmethyl, 3-cyclopentylpropyl, cyclohexyl, 2-cyclohexylethyl, norborn-2-yl, vinyl, 1-methylvinyl, 2-methylvinyl, 2,2- dimethylvinyl, allyl, 3-butenyl; phenyl, methylphenyl, dimethylphenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, naphth-1-yl, naphth-2-yl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl)methyl, (2-naphthyl)methyl; tetrahydrofuran-2-yl, furan-2-yl, 5-methyl-2-(trifluoromethyl)furan-3-yl, 2-methyl-5-phenylfuran-3-yl, thiophen-2-yl, (thiophen-2-yl)methyl, 3-chlorothiophen-2-yl, 2,5-dichlorothiophen-3-yl, benzothiophen-2-yl, 3-chlorobenzothiophen-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, indol-3-ylcarboxyl, pyridinyl, chloropyridinyl, dichloropyridinyl, 5-(bromo)pyridin-3-yl, piperazin-2-yl, quinoxal-2-yl; fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane; methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 2-chloroethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy; amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyridylamino, pyrid-3-ylamino, dimethylamino, 1-pyrrolidinyl and 4-morpholinyl;

wherein said $R_1$ and said $R_2$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

wherein said $R_2$ and said $R_5$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_5$ form a saturated ring comprising 5- to 7-members, said $R_5$ optionally is a bond;

wherein said $R_2$ and said $R_6$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_6$ form a saturated ring comprising 5- to 7-members, said $R_6$ optionally is a bond;

Y is chosen from:
a hydrogen atom;
a halogen atom;
a group chosen from —$OR_8$, —$SR_8$, and —NH—$SO_2R_8$, wherein
$R_8$ is chosen from:
linear and branched $C_1$–$C_8$ alkyl groups, optionally substituted with at least one group chosen from a halogen atom, a hydroxyl group, $C_1$–$C_4$ alkoxy groups, an amino group, amino($C_1$–$C_4$ alkyl) groups, a carboxyl group, and $C_1$–$C_4$ alkoxycarbonyl groups, wherein at least one branch of said branched $C_1$–$C_8$ alkyl groups optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
a benzyl group, optionally substituted with one or two oxy groups, with the proviso that:
(i) when $R_2$ is a hydroxyl group, Y is not a —NH—$SO_2R_8$ group;

provided that:
(i) when said $R_2$ and said $R_4$ are hydrogen atoms, and when said $R_3$ is chosen from substituted and unsubstituted $C_1$–$C_4$ alkyl groups, X is not a an —$OR_5$ group, wherein $R_5$ is chosen from substituted and unsubstituted $C_1$–$C_4$ alkyl groups;
(ii) when said $R_2$ and said $R_4$ are hydrogen atoms, and when said $R_3$ is chosen from substituted and unsubstituted $C_1$–$C_4$ alkyl groups, X is not a $NR_6R_7$ group; and (iii) when said $R_2$, said $R_4$, and said Y, are hydrogen atoms, and when said X is a $NR_6R_7$ group, wherein said $R_6$ and $R_7$ are hydrogen atoms, said $R_3$ is not chosen from a fluorine atom, a chlorine atom and a bromine atom.

24. A composition for oxidation dyeing keratinous fibers comprising, in a medium suitable for dyeing:
(a) at least one oxidation base; and
(b) at least one coupler chosen from compounds of formula (I) and acid addition salts thereof:

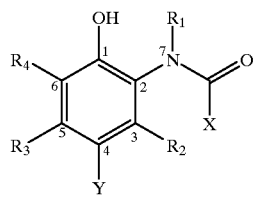

(I)

wherein:
$R_1$ is chosen from a hydrogen atom, linear and branched, saturated and unsaturated groups comprising from 1–15 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the provisos that:
(i) said $R_1$ does not comprise a group chosen from a peroxide group, a diazo group, a nitro group, and a nitroso group, and
(ii) said $SO_2$ group is not directly linked to the nitrogen at the 7-position of formula (I);

X is chosen from groups $OR_5$ and $NR_6R_7$, wherein
$R_5$ is chosen from linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) said $R_5$ does not comprise a group chosen from a peroxide group, a diazo group, a nitro group, and a nitroso group;

$R_6$ and $R_7$, which are identical or different, are each chosen from a hydrogen atom, linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) both said $R_6$ and $R_7$ do not comprise a group chosen from a peroxide group, a diazo group, a nitro group, and a nitroso group, and said $R_6$ and $R_7$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R, wherein
R is chosen from linear, branched, saturated, and unsaturated, $C_1$–$C_6$ alkyl groups, optionally substituted with at least one halogen atom, wherein at least one carbon atom is optionally replaced by a unit chosen from an oxygen atom, a nitrogen atom, a sulfur atom, and a $SO_2$ group, and at least one branch of said branched $C_1$–$C_6$ alkyl group optionally forms at least one saturated or unsaturated 3- to 6-membered ring; with the proviso that:
(i) said R does not comprise a group chosen from a peroxide group, a diazo group, a nitro group, and a nitroso group;

wherein
said $R_1$ and said $R_5$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group; and said $R_1$ and said $R_6$ optionally form a ring, chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

$R_2$ and $R_3$, which are identical or different, are each chosen from a hydrogen atom, a halogen atom, and linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally form at least one 3- to 7-membered ring comprising at least one carbon atom, with the provisos that:
(i) said $R_2$ and said $R_3$ do not comprise a group chosen from a peroxide group, a diazo group, a nitro group, and a nitroso group; and
(ii) said $R_2$ and said $R_3$ are not directly linked to the benzene ring of formula (I) by a —NH—NH—;

$R_4$ is chosen from:
an atom chosen from hydrogen, chlorine, and fluorine;
a group chosen from methyl, hydroxymethyl, aminomethyl, methoxy and methylamino; and
a group —NH(CO)$R_{16}$ wherein $R_{16}$ is a unit of a group (G3), chosen from:
methyl, ethyl, propyl, allyl, phenyl, tetrahydrofuran-2-yl, furan-2-yl, thiophen-2-yl, pyridinyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl and 4-morpholinyl;

wherein said $R_1$ and said $R_2$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

wherein said $R_2$ and said $R_5$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_5$ form a saturated ring comprising 5- to 7-members, said $R_5$ optionally is a bond;

wherein said $R_2$ and said $R_6$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_6$ form a saturated ring comprising 5- to 7-members, said $R_6$ optionally is a bond;

Y is chosen from:
a hydrogen atom;
a halogen atom;
a group chosen from —$OR_8$, —$SR_8$, and —NH—$SO_2R_8$, wherein
$R_8$ is chosen from:
linear and branched $C_1$–$C_8$ alkyl groups, optionally substituted with at least one group chosen from a halogen atom, a hydroxyl group, $C_1$–$C_4$ alkoxy groups, an amino group, amino($C_1$–$C_4$ alkyl) groups, a carboxyl group, and $C_1$–$C_4$ alkoxycarbonyl groups, wherein at least one branch of said branched $C_1$–$C_8$ alkyl groups optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
a benzyl group, optionally substituted with one or two oxy groups, with the proviso that:
(i) when $R_2$ is a hydroxyl group, Y is not a —NH—$SO_2R_8$ group;

provided that:
(i) when said $R_2$ and said $R_4$ are hydrogen atoms, and when said $R_3$ is chosen from substituted and unsubstituted $C_1$–$C_4$ alkyl groups, X is not a an —$OR_5$ group, wherein $R_5$ is chosen from substituted and unsubstituted $C_1$–$C_4$ alkyl groups;
(ii) when said $R_2$ and said $R_4$ are hydrogen atoms, and when said $R_3$ is chosen from substituted and unsubstituted $C_1$–$C_4$ alkyl groups, X is not a $NR_6R_7$ group; and
(iii) when said $R_2$, said $R_4$, and said Y, are hydrogen atoms, and when said X is a $NR_6R_7$ group, wherein said $R_6$ and $R_7$ are hydrogen atoms, said $R_3$ is not chosen from a fluorine atom, a chlorine atom and a bromine atom.

25. A composition according claim 1, wherein Y is a moiety chosen from:
an atom chosen from hydrogen, chlorine, fluorine, and bromine; and a group chosen from methoxy, ethoxy, propoxy, benzyloxy, phenoxy, —$OCH_2CH_2OCH_3$, —$OCH_2CH_2N(CH_3)_2$, —$OCH_2(CO)OH$, —$OCH_2(CO)OCH_3$, —$OCH_2(CO)OC_2H_5$, —$SCH_2CH_2CO_2H$, and —$NHSO_2CH_3$;
with the proviso that when $R_2$ is a hydroxyl group, Y is other than a —$NHSO_2CH_3$ group.

26. A composition according claim 25, wherein Y is a group chosen from a hydrogen atom; a chlorine atom; a methoxy group; a —$OCH_2(CO)OH$ group, and a —$OCH_2(CO)OCH_3$ group.

27. A composition for oxidation dyeing keratinous fibers comprising, in a medium suitable for dyeing:
(a) at least one oxidation base; and
(b) at least one coupler chosen from compounds of formula (I) and acid addition salts thereof:

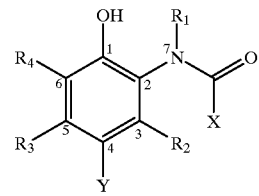

(I)

wherein at least one coupler of formula (I) is chosen from the Groups (i), (ii), (iii), and (iv) in which:
Group (i) is said at least one coupler of formula (I) wherein:
$R_1$ is a hydrogen atom;
X is a group chosen from methoxy, ethoxy, propyloxy, isopropyloxy, butyloxy, isobutyloxy, 2-hydroxyethoxy, 2-methoxyethoxy, allyloxy, amino, methylamino, ethylamino, propylamino, isopropylamino, butylamino, isobutylamino, 2-hydroxyethylamino, 2-methoxyethylamino, 3-hydroxypropylamino, 2,3-dihydroxypropylamino, allylamino, dimethylamino, diethylamino, di(2-hydroxyethyl)amino, pyrrolidin-1-yl, 3-hydroxypyrrolidin-1-yl, and 3,4-dihydroxypyrrolidin-1-yl;
$R_2$ is chosen from:
a group chosen from hydroxyl, amino, methylamino, 2-hydroxyethylamino and diethylamino;
a group —$NH(CO)R_{17}$, wherein $R_{17}$ is a unit of group (G4), said unit is chosen from a methyl group, a methoxymethyl group, a 2-carboxyethyl group, a methoxy group, an amino group, an ethylamino group, a 1-pyrrolidinyl group; a methanesulphonylamino group, an ethanesulphonylamino group, and a dimethylaminosulphonylamino group;

$R_3$ is chosen from a hydrogen atom, a chlorine atom, and a methyl group;

$R_4$ is chosen from a hydrogen atom, a chlorine atom, a fluorine atom, and a methyl group; and Y is chosen from a hydrogen atom, a chlorine atom, a methoxy group, and a —OCH$_2$(CO)OCH$_3$ group;

Group (ii) is said at least one coupler of formula (I) wherein:

$R_1$ is a hydrogen atom;

X is a group chosen from methoxy, ethoxy, propyloxy, isopropyloxy, butyloxy, isobutyloxy, 2-hydroxyethoxy, 2-methoxyethoxy, allyloxy, amino, methylamino, ethylamino, propylamino, isopropylamino, butylamino, isobutylamino, 2-hydroxyethylamino, 2-methoxyethylamino, 3-hydroxypropylamino, 2,3-dihydroxypropylamino, allylamino, dimethylamino, diethylamino, di(2-hydroxyethyl)amino, pyrrolidin-1-yl, 3-hydroxypyrrolidin-1-yl, and 3,4-dihydroxypyrrolidin-1-yl;

$R_2$ is chosen from a hydrogen atom and a methyl group;

$R_3$ is chosen from:
  a group chosen from hydroxyl, amino, methylamino, 2-hydroxyethylamino, diethylamino, methanesulphonylamino, ethanesulphonylamino and dimethylaminosulphonylamino; and
  a group —NH(CO)$R_{18}$, wherein $R_{18}$ is a moiety of group (G4), said moiety is chosen from a methyl group, a methoxymethyl group, a 2-carboxyethyl group, a methoxy group, an amino group, an ethylamino group, a 1-pyrrolidinyl group, a methanesulphonylamino group, an ethanesulphonylamino group, and a dimethylaminosulphonylamino group;

$R_4$ is chosen from a hydrogen atom, a chlorine atom, a fluorine atom, and a methyl group; and Y is chosen from a hydrogen atom, a chlorine atom, a methoxy group, and a —OCH$_2$(CO)OCH$_3$ group;

Group (iii) is said at least one coupler of formula (I) wherein:

$R_1$ is a hydrogen atom;

X is a group chosen from methoxy, ethoxy, propyloxy, isopropyloxy, butyloxy, isobutyloxy, 2-hydroxyethoxy, 2-methoxyethoxy, allyloxy, amino, methylamino, ethylamino, propylamino, isopropylamino, butylamino, isobutylamino, 2-hydroxyethylamino, 2-methoxyethylamino, 3-hydroxypropylamino, 2,3-dihydroxypropylamino, allylamino, dimethylamino, diethylamino, di(2-hydroxyethyl)amino, pyrrolidin-1-yl, 3-hydroxypyrrolidin-1-yl, and 3,4-dihydroxypyrrolidin-1-yl;

$R_2$ is chosen from a hydrogen atom, and a methyl group;

$R_3$ is chosen from a hydrogen atom, a chlorine atom, a methyl group, a methoxy group and a methylamino group;

$R_4$ is chosen from a group —NH(CO)$R_{19}$, wherein $R_{19}$ is a unit of group (G4), said unit is chosen from a methyl group, a methoxymethyl group, a 2-carboxyethyl group, a methoxy group, an amino group, an ethylamino group, a 1-pyrrolidinyl group; a methanesulphonylamino group, an ethanesulphonylamino group, and a dimethylaminosulphonylamino group; and Y is chosen from a hydrogen atom, a chlorine atom, a methoxy group, and a —OCH$_2$(CO)OCH$_3$ group; and Group (iv) is said at least one coupler of formula (I) wherein:

$R_1$ is a hydrogen atom;

X is a group chosen from methoxy, ethoxy, propyloxy, isopropyloxy, butyloxy, isobutyloxy, 2-hydroxyethoxy, 2-methoxyethoxy, allyloxy, amino, methylamino, ethylamino, propylamino, isopropylamino, butylamino, isobutylamino, 2-hydroxyethylamino, 2-methoxyethylamino, 3-hydroxypropylamino, 2,3-dihydroxypropylamino, allylamino, dimethylamino, diethylamino, di(2-hydroxyethyl)amino, pyrrolidin-1-yl, 3-hydroxypyrrolidin-1-yl, and 3,4-dihydroxypyrrolidin-1-yl;

$R_2$ is chosen from a hydrogen atom and a methyl group;

$R_3$ is chosen from a hydrogen atom, a methyl group and an ethyl group;

$R_4$ is chosen from a hydrogen atom, a chlorine atom, and a fluorine atom; and

Y is chosen from a hydrogen atom, a chlorine atom and a —OCH$_2$(CO)OCH$_3$ group provided that:

(i) when said $R_2$ and said $R_4$ are hydrogen atoms, and when said $R_3$ is chosen from substituted and unsubstituted $C_1$–$C_4$ alkyl groups, X is not a —OR$_5$ group, wherein $R_5$ is chosen from substituted and unsubstituted $C_1$–$C_4$ alkyl groups;

(ii) when said $R_2$ and said $R_4$ are hydrogen atoms, and when said $R_3$ is chosen from substituted and unsubstituted $C_1$–$C_4$ alkyl groups, X is not a NR$_6$R$_7$ group; and (iii) when said $R_2$, said $R_4$, and said Y are hydrogen atoms, and when said X is a NR$_6$R$_7$ group, wherein said $R_6$ and $R_7$ are hydrogen atoms, said $R_3$ is not chosen from a fluorine atom, a chlorine atom and a bromine atom.

28. A composition according to claim 1, wherein said at least one coupler of formula (I) is chosen from:

(2-Hydroxyphenyl)carbamic acid methyl ester,
(2-Hydroxyphenyl)carbamic acid ethyl ester,
(2-Hydroxyphenyl)carbamic acid 2-hydroxyethyl ester,
(2-Hydroxyphenyl)carbamic acid isopropyl ester,
1-(2-Hydroxyphenyl)urea,
3-(2-Hydroxyphenyl)-1-methylurea,
3-(2-Hydroxyphenyl)-1-ethylurea,
3-(2-Hydroxyphenyl)-1-(2-hydroxyethyl)urea,
3-(2-Hydroxyphenyl)-1-isopropylurea,
3-(2-Hydroxyphenyl)-1,1-dimethylurea,
3-(2-Hydroxyphenyl)-1,1-diethylurea,
3-(2-Hydroxyphenyl)-1,1-di(2-hydroxyethyl)urea,
(2-Hydroxy-5-chlorophenyl)carbamic acid methyl ester,
(2-Hydroxy-5-chlorophenyl)carbamic acid ethyl ester,
(2-Hydroxy-5-chlorophenyl)carbamic acid 2-hydroxyethyl ester,
(2-Hydroxy-5-chlorophenyl)carbamic acid isopropyl ester,
1-(2-Hydroxy-5-chlorophenyl)urea,
3-(2-Hydroxy-5-chlorophenyl)-1-methylurea, 3-(2-Hydroxy-5-chlorophenyl)-1-ethylurea,
3-(2-Hydroxy-5-chlorophenyl)-1-(2-hydroxyethyl)urea,
3-(2-Hydroxy-5-chlorophenyl)-1-isopropylurea,
3-(2-Hydroxy-5-chlorophenyl)-1,1-dimethylurea,
3-(2-Hydroxy-5-chlorophenyl)-1,1-diethylurea,
3-(2-Hydroxy-5-chlorophenyl)-1,1-di(2-hydroxyethyl)urea,
(2-Hydroxy-5-methoxyphenyl)carbamic acid methyl ester,
(2-Hydroxy-5-methoxyphenyl)carbamic acid ethyl ester,
(2-Hydroxy-5-methoxyphenyl)carbamic acid 2-hydroxyethyl ester,
(2-Hydroxy-5-methoxyphenyl)carbamic acid isopropyl ester,
3-(2-Hydroxy-5-methoxyphenyl)-1-(2-hydroxyethyl)urea,
3-(2-Hydroxy-5-methoxyphenyl)-1,1-di(2-hydroxyethyl)urea,
(2-Hydroxy-6-aminophenyl)carbamic acid methyl ester,
(2-Hydroxy-6-aminophenyl)carbamic acid ethyl ester,
(2-Hydroxy-6-aminophenyl)carbamic acid 2-hydroxyethyl ester,
(2-Hydroxy-6-aminophenyl)carbamic acid isopropyl ester,
1-(2-Hydroxy-6-aminophenyl)urea,
3-(2-Hydroxy-6-aminophenyl)-1-methylurea,
3-(2-Hydroxy-6-aminophenyl)-1-ethylurea,
3-(2-Hydroxy-6-aminophenyl)-1-(2-hydroxyethyl)urea,
3-(2-Hydroxy-6-aminophenyl)-1-isopropylurea,
3-(2-Hydroxy-6-aminophenyl)-1,1-dimethylurea,
3-(2-Hydroxy-6-aminophenyl)-1,1-diethylurea,
3-(2-Hydroxy-6-aminophenyl)-1,1-di(2-hydroxyethyl)urea,
(2-Hydroxy-4-aminophenyl)carbamic acid methyl ester,
(2-Hydroxy-4-aminophenyl)carbamic acid ethyl ester,
(2-Hydroxy-4-aminophenyl)carbamic acid 2-hydroxyethyl ester,
(2-Hydroxy-4-aminophenyl)carbamic acid isopropyl ester,
1-(2-Hydroxy-4-aminophenyl)urea,
3-(2-Hydroxy-4-aminophenyl)-1-methylurea,
3-(2-Hydroxy-4-aminophenyl)-1-ethylurea,
3-(2-Hydroxy-4-aminophenyl)-1-(2-hydroxyethyl)urea,
3-(2-Hydroxy-4-aminophenyl)-1-isopropylurea,
3-(2-Hydroxy-4-aminophenyl)-1,1-dimethylurea,
3-(2-Hydroxy-4-aminophenyl)-1,1-diethylurea,
3-(2-Hydroxy-4-aminophenyl)-1,1-di(2-hydroxyethyl)urea,
Pyrrolidine-1-carboxylic acid (4-amino-2-hydroxyphenyl)amide,
3-Hydroxypyrrolidine-1-carboxylic acid (4-amino-2-hydroxyphenyl)amide,
(2-Hydroxy-4-methylaminophenyl)carbamic acid methyl ester,
(2-Hydroxy-4-methylaminophenyl)carbamic acid ethyl ester,
(2-Hydroxy-4-methylaminophenyl)carbamic acid 2-hydroxyethyl ester,
(2-Hydroxy-4-methylaminophenyl)carbamic acid isopropyl ester,
1-(2-Hydroxy-4-methylaminophenyl)urea,
3-(2-Hydroxy-4-methylaminophenyl)-1-methylurea,
3-(2-Hydroxy-4-methylaminophenyl)-1-ethylurea,
3-(2-Hydroxy-4-methylaminophenyl)-1-(2-hydroxyethyl)urea,
3-(2-Hydroxy-4-methylaminophenyl)-1-isopropylurea,
3-(2-Hydroxy-4-methylaminophenyl)-1,1-dimethylurea,
3-(2-Hydroxy-4-methylaminophenyl)-1,1-diethylurea,
3-(2-Hydroxy-4-methylaminophenyl)-1,1-di(2-hydroxyethyl)urea,
(2-Hydroxy-4-(2-hydroxyethyl)aminophenyl)carbamic acid methyl ester,
(2-Hydroxy-4-(2-hydroxyethyl)aminophenyl)carbamic acid ethyl ester,
(2-Hydroxy-4-(2-hydroxyethyl)aminophenyl)carbamic acid 2-hydroxyethyl ester,
(2-Hydroxy-4-(2-hydroxyethyl)aminophenyl)carbamic acid isopropyl ester,
1-(2-Hydroxy-4-(2-hydroxyethyl)aminophenyl)urea,
3-(2-Hydroxy-4-(2-hydroxyethyl)aminophenyl)-1-methylurea,
3-(2-Hydroxy-4-(2-hydroxyethyl)aminophenyl)-1-ethylurea,
3-(2-Hydroxy-4-(2-hydroxyethyl)aminophenyl)-1-(2-hydroxyethyl)urea,
3-(2-Hydroxy-4-(2-hydroxyethyl)aminophenyl)-1-isopropylurea,
3-(2-Hydroxy-4-(2-hydroxyethyl)aminophenyl)-1,1-dimethylurea,
3-(2-Hydroxy-4-(2-hydroxyethyl)aminophenyl)-1,1-diethylurea,
3-(2-Hydroxy-4-(2-hydroxyethyl)aminophenyl)-1,1-di(2-hydroxyethyl)urea,
(2-Hydroxy-4-amino-5-chlorophenyl)carbamic acid methyl ester,
(2-Hydroxy-4-amino-5-chlorophenyl)carbamic acid ethyl ester,
(2-Hydroxy-4-amino-5-chlorophenyl)carbamic acid 2-hydroxyethyl ester,
(2-Hydroxy-4-amino-5-chlorophenyl)carbamic acid isopropyl ester,
1-(2-Hydroxy-4-amino-5-chlorophenyl)urea,
3-(2-Hydroxy-4-amino-5-chlorophenyl)1-methylurea,
3-(2-Hydroxy-4-amino-5-chlorophenyl)1-ethylurea,
3-(2-Hydroxy-4-amino-5-chlorophenyl)-1-(2-hydroxyethyl)urea,
3-(2-Hydroxy-4-amino-5-chlorophenyl)-1-isopropylurea,
3-(2-Hydroxy-4-amino-5-chlorophenyl)-1,1-dimethylurea,
3-(2-Hydroxy-4-amino-5-chlorophenyl)-1,1-diethylurea,
3-(2-Hydroxy-4-amino-5-chlorophenyl)-1,1-di(2-hydroxyethyl)urea,
(2-Hydroxy-4-methylamino-5-chlorophenyl)carbamic acid methyl ester,
(2-Hydroxy-4-methylamino-5-chlorophenyl)carbamic acid ethyl ester,
(2-Hydroxy-4-methylamino-5-chlorophenyl)carbamic acid 2-hydroxyethyl ester,
(2-Hydroxy-4-methylamino-5-chlorophenyl)carbamic acid isopropyl ester, 1-(2-Hydroxy-4-methylamino-5-chlorophenyl)urea,
3-(2-Hydroxy-4-methylamino-5-chlorophenyl)-1-methylurea,
3-(2-Hydroxy-4-methylamino-5-chlorophenyl)-1-ethylurea,
3-(2-Hydroxy-4-methylamino-5-chlorophenyl)-1-(2-hydroxyethyl)urea,
3-(2-Hydroxy-4-methylamino-5-chlorophenyl)-1-isopropylurea,
3-(2-Hydroxy-4-methylamino-5-chlorophenyl)-1,1-dimethylurea,
3-(2-Hydroxy-4-methylamino-5-chlorophenyl)-1,1-diethylurea,
3-(2-Hydroxy-4-methylamino-5-chlorophenyl)-1,1-di(2-hydroxyethyl)urea,
(2-Hydroxy-4-(2-hydroxyethyl)amino-5-chlorophenyl)carbamic acid methyl ester,
(2-Hydroxy-4-(2-hydroxyethyl)amino-5-chlorophenyl)carbamic acid ethyl ester,
(2-Hydroxy-4-(2-hydroxyethyl)amino-5-chlorophenyl)carbamic acid 2-hydroxyethyl ester,
(2-Hydroxy-4-(2-hydroxyethyl)amino-5-chlorophenyl)carbamic acid isopropyl ester,
1-(2-Hydroxy-4-(2-hydroxyethyl)amino-5-chlorophenyl)urea,
3-(2-Hydroxy-4-(2-hydroxyethyl)amino-5-chlorophenyl)-1-methylurea,
3-(2-Hydroxy-4-(2-hydroxyethyl)amino-5-chlorophenyl)-1-ethylurea,
3-(2-Hydroxy-4-(2-hydroxyethyl)amino-5-chlorophenyl)-1-(2-hydroxyethyl)urea,
3-(2-Hydroxy-4-(2-hydroxyethyl)amino-5-chlorophenyl)-1-isopropylurea,
3-(2-Hydroxy-4-(2-hydroxyethyl)amino-5-chlorophenyl)-1,1-dimethylurea,
3-(2-Hydroxy-4-(2-hydroxyethyl)amino-5-chlorophenyl)-1,1-diethylurea,
3-(2-Hydroxy-4-(2-hydroxyethyl)amino-5-chlorophenyl)-1,1-di(2-hydroxyethyl)urea,
(2-Hydroxy-4-amino-5-methoxyphenyl)carbamic acid methyl ester,
(2-Hydroxy-4-amino-5-methoxyphenyl)carbamic acid ethyl ester,
(2-Hydroxy-4-amino-5-methoxyphenyl)carbamic acid 2-hydroxyethyl ester,
(2-Hydroxy-4-amino-5-methoxyphenyl)carbamic acid isopropyl ester,
3-(2-Hydroxy-4-amino-5-methoxyphenyl) 1-(2-hydroxyethyl)urea,
3-(2-Hydroxy-4-amino-5-methoxyphenyl)-1,1-di(2-hydroxyethyl)urea,
(2-Hydroxy-4-methylamino-5-methoxyphenyl)carbamic acid methyl ester,
(2-Hydroxy-4-methylamino-5-methoxyphenyl)carbamic acid ethyl ester,
(2-Hydroxy-4-methylamino-5-methoxyphenyl)carbamic acid 2-hydroxyethyl ester,
(2-Hydroxy-4-methylamino-5-methoxyphenyl)carbamic acid isopropyl ester,
1-(2-Hydroxy-4-methylamino-5-methoxyphenyl)urea,
3-(2-Hydroxy-4-methylamino-5-methoxyphenyl)-1-methylurea,
3-(2-Hydroxy-4-methylamino-5-methoxyphenyl)1-ethylurea,
3-(2-Hydroxy-4-methylamino-5-methoxyphenyl)-1-(2-hydroxyethyl)urea,
3-(2-Hydroxy-4-methylamino-5-methoxyphenyl)-1-isopropylurea,
3-(2-Hydroxy-4-methylamino-5-methoxyphenyl)-1,1-dimethylurea,
3-(2-Hydroxy-4-methylamino-5-methoxyphenyl)-1,1-diethylurea,
3-(2-Hydroxy-4-methylamino-5-methoxyphenyl)-1,1-di(2-hydroxyethyl)urea,
(2-Hydroxy-4-(2-hydroxyethyl)amino-5-methoxyphenyl)carbamic acid methyl ester,
(2-Hydroxy-4-(2-hydroxyethyl)amino-5-methoxyphenyl)carbamic acid ethyl ester,
(2-Hydroxy-4-(2-hydroxyethyl)amino-5-methoxyphenyl)carbamic acid 2-hydroxyethyl ester,
(2-Hydroxy-4-(2-hydroxyethyl)amino-5-methoxyphenyl)carbamic acid isopropyl ester,
1-(2-Hydroxy-4-(2-hydroxyethyl)amino-5-methoxyphenyl)urea,
3-(2-Hydroxy-4-(2-hydroxyethyl)amino-5-methoxyphenyl)-1-methylurea,
3-(2-Hydroxy-4-(2-hydroxyethyl)amino-5-methoxyphenyl)-1-ethylurea,
3-(2-Hydroxy-4-(2-hydroxyethyl)amino-5-methoxyphenyl)-1-(2-hydroxyethyl)urea,
3-(2-Hydroxy-4-(2-hydroxyethyl)amino-5-methoxyphenyl)-1-isopropylurea,
3-(2-Hydroxy-4-(2-hydroxyethyl)amino-5-methoxyphenyl)-1,1-dimethylurea,
3-(2-Hydroxy-4-(2-hydroxyethyl)amino-5-methoxyphenyl)-1,1-diethylurea,
3-(2-Hydroxy-4-(2-hydroxyethyl)amino-5-methoxyphenyl)-1,1-di(2-hydroxyethyl)urea,
(2-Hydroxy-3-methoxycarbonylaminophenyl)carbamic acid methyl ester,
(2-Hydroxy-3-ethoxycarbonylaminophenyl)carbamic acid ethyl ester,
(2-Hydroxy-3-(2-hydroxyethoxy)carbonylaminophenyl)-carbamic acid 2-hydroxyethyl ester,
(2-Hydroxy-3-isopropoxycarbonylaminophenyl)carbamic acid isopropyl ester,
1-(2-Hydroxy-3-ureidophenyl)urea,
3-(2-Hydroxy-3-(3-methylureido)phenyl)-1-methylurea,
3-(2-Hydroxy-3-(3-ethylureido)phenyl)1-ethylurea,
3-(2-Hydroxy-3-(3-(2-hydroxyethyl)ureido)phenyl)-1-(2-hydroxyethyl)urea,
3-(2-Hydroxy-3-(3-isopropylureido)phenyl)1-isopropylurea,
3-(2-Hydroxy-3-(3,3-dimethylureido)phenyl)1,1-dimethylurea,
and their acid addition salts.

29. A composition according to claim 1, wherein said at least one coupler of formula (I) is chosen from:
(2-Hydroxy-4-aminophenyl)carbamic acid methyl ester,
(2-Hydroxy-4-aminophenyl)carbamic acid ethyl ester,
(2-Hydroxy-4-aminophenyl)carbamic acid 2-hydroxyethyl ester,
(2-Hydroxy-4-aminophenyl)carbamic acid isopropyl ester, 1-(2-Hydroxy-4-aminophenyl)urea,
3-(2-Hydroxy-4-aminophenyl)-1-methylurea,
3-(2-Hydroxy-4-aminophenyl)-1-ethylurea,
3-(2-Hydroxy-4-aminophenyl)-1-(2-hydroxyethyl)urea,
3-(2-Hydroxy-4-aminophenyl)-1-isopropylurea,
3-(2-Hydroxy-4-aminophenyl)-1,1-dimethylurea,
(2-Hydroxy-4-methylaminophenyl)carbamic acid methyl ester,
(2-Hydroxy-4-methylaminophenyl)carbamic acid ethyl ester,
(2-Hydroxy-4-methylaminophenyl)carbamic acid 2-hydroxyethyl ester,
(2-Hydroxy-4-methylaminophenyl)carbamic acid isopropyl ester,
1-(2-Hydroxy-4-methylaminophenyl)urea,
3-(2-Hydroxy-4-methylaminophenyl)-1-methylurea,
3-(2-Hydroxy-4-methylaminophenyl)-1-ethylurea,
3-(2-Hydroxy-4-methylaminophenyl)-1-(2-hydroxyethyl)urea,
3-(2-Hydroxy-4-methylaminophenyl)-1-isopropylurea,
3-(2-Hydroxy-4-methylaminophenyl)-1,1-dimethylurea,
(2-Hydroxy-4-(2-hydroxyethyl)aminophenyl)carbamic acid methyl ester,
(2-Hydroxy-4-(2-hydroxyethyl)aminophenyl)carbamic acid ethyl ester,
(2-Hydroxy-4-(2-hydroxyethyl)aminophenyl)carbamic acid 2-hydroxyethyl ester,
(2-Hydroxy-4-(2-hydroxyethyl)aminophenyl)carbamic acid isopropyl ester,
1-(2-Hydroxy-4-(2-hydroxyethyl)aminophenyl)urea
3-(2-Hydroxy-4-(2-hydroxyethyl)aminophenyl)-1-methylurea,
3-(2-Hydroxy-4-(2-hydroxyethyl)aminophenyl)-1-ethylurea,
3-(2-Hydroxy-4-(2-hydroxyethyl)aminophenyl)-1-(2-hydroxyethyl)urea,
3-(2-Hydroxy-4-(2-hydroxyethyl)aminophenyl)-1-isopropylurea,
3-(2-Hydroxy-4-(2-hydroxyethyl)aminophenyl)-1,1-dimethylurea,
(2-Hydroxy-4-amino-5-chlorophenyl)carbamic acid methyl ester,
(2-Hydroxy-4-amino-5-chlorophenyl)carbamic acid ethyl ester,
(2-Hydroxy-4-amino-5-chlorophenyl)carbamic acid 2-hydroxyethyl ester,
(2-Hydroxy-4-amino-5-chlorophenyl)carbamic acid isopropyl ester,
1-(2-Hydroxy-4-amino-5-chlorophenyl)urea,
3-(2-Hydroxy-4-amino-5-chlorophenyl)-1-methylurea,
3-(2-Hydroxy-4-amino-5-chlorophenyl)-1-ethylurea,
3-(2-Hydroxy-4-amino-5-chlorophenyl)-1-(2-hydroxyethyl)urea,
3-(2-Hydroxy-4-amino-5-chlorophenyl)-1-isopropylurea,
3-(2-Hydroxy-4-amino-5-chlorophenyl)-1,1-dimethylurea,
(2-Hydroxy-4-methylamino-5-chlorophenyl)carbamic acid methyl ester,
(2-Hydroxy-4-methylamino-5-chlorophenyl)carbamic acid ethyl ester,
(2-Hydroxy-4-methylamino-5-chlorophenyl)carbamic acid 2-hydroxyethyl ester,
(2-Hydroxy-4-methylamino-5-chlorophenyl)carbamic acid isopropyl ester,
1-(2-Hydroxy-4-methylamino-5-chlorophenyl)urea,
3-(2-Hydroxy-4-methylamino-5-chlorophenyl)-1-methylurea,
3-(2-Hydroxy-4-methylamino-5-chlorophenyl)-1-ethylurea,
3-(2-Hydroxy-4-methylamino-5-chlorophenyl)-1-(2-hydroxyethyl)urea,
3-(2-Hydroxy-4-methylamino-5-chlorophenyl)-1-isopropylurea,
3-(2-Hydroxy-4-methylamino-5-chlorophenyl)-1,1-dimethylurea,
(2-Hydroxy-4-(2-hydroxyethyl)amino-5-chlorophenyl)carbamic acid methyl ester,
(2-Hydroxy-4-(2-hydroxyethyl)amino-5-chlorophenyl)carbamic acid ethyl ester,
(2-Hydroxy-4-(2-hydroxyethyl)amino-5-chlorophenyl)carbamic acid 2-hydroxyethyl ester,
(2-Hydroxy-4-(2-hydroxyethyl)amino-5-chlorophenyl)carbamic acid isopropyl ester,
1-(2-Hydroxy-4-(2-hydroxyethyl)amino-5-chlorophenyl)urea,
3-(2-Hydroxy-4-(2-hydroxyethyl)amino-5-chlorophenyl)-1-methylurea,
3-(2-Hydroxy-4-(2-hydroxyethyl)amino-5-chlorophenyl)-1-ethylurea,
3-(2-Hydroxy-4-(2-hydroxyethyl)amino-5-chlorophenyl)-1-(2-hydroxyethyl)urea,
3-(2-Hydroxy-4-(2-hydroxyethyl)amino-5-chlorophenyl)-1-isopropylurea,
3-(2-Hydroxy-4-(2-hydroxyethyl)amino-5-chlorophenyl)-1,1-dimethylurea,
(2-Hydroxy-4-amino-5-methoxyphenyl)carbamic acid methyl ester,
(2-Hydroxy-4-amino-5-methoxyphenyl)carbamic acid ethyl ester,
(2-Hydroxy-4-amino-5-methoxyphenyl)carbamic acid 2-hydroxyethyl ester,
(2-Hydroxy-4-amino-5-methoxyphenyl)carbamic acid isopropyl ester,
3-(2-Hydroxy-4-amino-5-methoxyphenyl)-1-(2-hydroxyethyl)urea,
(2-Hydroxy-4-methylamino-5-methoxyphenyl)carbamic acid methyl ester,
(2-Hydroxy-4-methylamino-5-methoxyphenyl)carbamic acid ethyl ester,
(2-Hydroxy-4-methylamino-5-methoxyphenyl)carbamic acid 2-hydroxyethyl ester,
(2-Hydroxy-4-methylamino-5-methoxyphenyl)carbamic acid isopropyl ester,
1-(2-Hydroxy-4-methylamino-5-,methoxyphenyl)urea
3-(2-Hydroxy-4-methylamino-5-methoxyphenyl)-1-methylurea,
3-(2-Hydroxy-4-methylamino-5-methoxyphenyl)-1-ethylurea,
3-(2-Hydroxy-4-methylamino-5-methoxyphenyl)-1-(2-hydroxyethyl)urea,
3-(2-Hydroxy-4-methylamino-5-methoxyphenyl)-1-isopropylurea, 3-(2-Hydroxy-4-methylamino-5-methoxyphenyl)-1,1-dimethylurea, (2-Hydroxy-4-(2-hydroxyethyl)amino-5-methoxyphenyl) carbamic acid methyl ester, (2-Hydroxy-4-(2-hydroxyethyl)amino-5-methoxyphenyl) carbamic acid ethyl ester, (2-Hydroxy-4-(2-hydroxyethyl)amino-5-methoxyphenyl) carbamic acid 2-hydroxyethyl ester, (2-Hydroxy)-4-(2-hydroxyethyl)amino-5-methoxyphenyl)carbamic acid isopropyl ester, 1-(2-Hydroxy-4-(2-hydroxyethyl)amino-5-methoxyphenyl)urea, 3-(2-Hydroxy-4-(2-hydroxyethyl)amino-5-methoxyphenyl)-1-methylurea, 3-(2-Hydroxy-4-(2-hydroxyethyl)amino-5-methoxyphenyl)-1-ethylurea, 3-(2-Hydroxy-4-(2-hydroxyethyl)amino-5-methoxyphenyl)-1-(2-hydroxyethyl)urea, 3-(2-Hydroxy-4-(2-hydroxyethyl)amino-5-methoxyphenyl)-1-isopropylurea, 3-(2-Hydroxy-4-(2-hydroxyethyl)amino-5-methoxyphenyl)-1,1-dimethylurea, and their acid addition salts.

30. A composition according to claim 1, wherein said at least one coupler of formula (I) is chosen from:

(2-Hydroxy-4-aminophenyl)carbamic acid methyl ester, (2-Hydroxy-4-aminophenyl)carbamic acid ethyl ester, (2-Hydroxy-4-aminophenyl)carbamic acid 2-hydroxyethyl ester, (2-Hydroxy-4-aminophenyl)carbamic acid isopropyl ester, 1-(2-Hydroxy-4-aminophenyl)urea 3-(2-Hydroxy-4-aminophenyl)-1-methylurea, 3-(2-Hydroxy-4-aminophenyl)-1-ethylurea, 3-(2-Hydroxy-4-aminophenyl)-1-(2-hydroxyethyl)urea, 3-(2-Hydroxy-4-aminophenyl)-1-isopropylurea, 3-(2-Hydroxy-4-aminophenyl)-1,1-dimethylurea, (2-Hydroxy-4-amino-5-chlorophenyl)carbamic acid methyl ester, (2-Hydroxy-4-amino-5-chlorophenyl)carbamic acid ethyl ester, (2-Hydroxy-4-amino-5-chlorophenyl)carbamic acid 2-hydroxyethyl ester, (2-Hydroxy-4-amino-5-chlorophenyl)carbamic acid isopropyl ester, 1-(2-Hydroxy-4-amino-5-chlorophenyl)urea, 3-(2-Hydroxy-4-amino-5-chlorophenyl)-1-methylurea, 3-(2-Hydroxy-4-amino-5-chlorophenyl)-1-ethylurea, 3-(2-Hydroxy-4-amino-5-chlorophenyl)-1-(2-hydroxyethyl)urea, 3-(2-Hydroxy-4-amino-5-chlorophenyl)-1-isopropylurea, 3-(2-Hydroxy-4-amino-5-chlorophenyl)-1,1-dimethylurea, (2-Hydroxy-4-amino-5-methoxyphenyl)carbamic acid methyl ester, (2-Hydroxy-4-amino-5-methoxyphenyl)carbamic acid ethyl ester, (2-Hydroxy-4-amino-5-methoxyphenyl)carbamic acid 2-hydroxyethyl ester, (2-Hydroxy-4-amino-5-methoxyphenyl)carbamic acid isopropyl ester, 3-(2-Hydroxy-4-amino-5-methoxyphenyl)-1-(2-hydroxyethyl)urea, and their acid addition salts.

31. A composition according to claim 1, wherein said at least one coupler of formula (I) is present in an amount ranging from 0.0005 to 12% by weight relative to the total weight of the dyeing composition.

32. A composition according to claim 31, wherein said at least one coupler of formula (I) is present in an amount ranging from 0.005 to 6% by weight relative to the total weight of the dyeing composition.

33. A composition according to claim 1, wherein said at least one oxidation base is chosen from para-phenylenediamines, bisphenylalkylenediamines, para-aminophenols, ortho-aminophenols, heterocyclic bases, and acid addition salts thereof.

34. A composition according to claim 33, wherein said para-phenylenediamines are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N, N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)para-phenylenediamine, N-(β,γ-dihydroxypropyl)-para-phenylenediamine, N-(4'-aminophenyl)para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid addition salts thereof.

35. A composition according to claim 34, said para-phenylenediamines are chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and acid addition salts thereof.

36. A composition according to claim 33, wherein said bisphenylalkylenediamines are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis (ethyl)-N,N'-bis(4'-amino-3'-methylphenyl) ethylenediamine, 1,8-bis(2,5-diaminophenoxy)-3,5-dioxaoctane, and acid addition salts thereof.

37. A composition according to claim 33, wherein said para-aminophenols are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino- 2-methoxymethylphenol, 4-amino-2-aminomethylphenol, 4-amino-2-(β-hydroxyethylaminomethyl)phenol, 4-amino-2-fluorophenol, and acid addition salts thereof.

38. A composition according to claim 33, wherein said ortho-aminophenols are chosen from 2-aminophenol, 2-amino-5-methylphenol, 2-amino-6-methylphenol, 5-acetamido-2-aminophenol, and acid addition salts thereof.

39. A composition according to claim 33, wherein said heterocyclic bases are chosen from pyridine derivatives, pyrimidine derivatives, pyrazole derivatives and acid addition salts thereof.

40. A composition according to claim 39, wherein said pyridine derivatives are chosen from 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and acid addition salts thereof.

41. A composition according to claim 39, wherein said pyrimidine derivatives are chosen from 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine; and the pyrazolopyrimidine, pyrazolo[1,5-a]pyrimidine-3,7-diamine; 2-methylpyrazolo[1,5-a]pyrimidine-3,7-diamine; 5-methylpyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)aminono]ethanol, 2-[(7-aminopyrazolo[1,5-a]-pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, a corresponding tautomeric form thereof, when a tautomeric equilibrium exists, and acid addition salts thereof.

42. A composition according to claim 39, wherein said pyrazole derivatives are chosen from 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and acid addition salts thereof.

43. A composition according to claim 1, wherein said at least one oxidation base is present in an amount ranging from 0.0005 to 12% by weight relative to the total weight of the dyeing composition.

44. A composition according to claim 43, wherein said at least one oxidation base is present in an amount ranging from 0.005 to 6% by weight relative to the total weight of the dyeing composition.

45. A composition according to claim 1, further comprising at least one additional coupler chosen from meta-phenylenediamines, meta-aminophenols, meta-diphenols, heterocyclic couplers and acid addition salts thereof.

46. A composition according to claim 45, wherein said heterocyclic couplers are chosen from indole derivatives, indoline derivatives, pyridine derivatives, pyrazolones, and acid addition salts thereof.

47. A composition according to claim 45, wherein said at least one additional coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, and acid addition salts thereof.

48. A composition according to claim 45, wherein said at least one additional coupler is present in an amount ranging from 0.0001 to 10% by weight relative to the total weight of the dyeing composition.

49. A composition according to claim 48, wherein said at least one additional coupler is present in an amount ranging from 0.005 to 5% by weight relative to the total weight of the dyeing composition.

50. A composition according to claim 1, wherein said acid addition salts are chosen from a hydrochloride, a hydrobromide, a sulphate, a citrate, a succinate, a tartrate, a lactate and an acetate.

51. A composition according to claim 1, wherein said medium suitable for dyeing is chosen from media comprising water; and media comprising at least one organic solvent.

52. A composition according to claim 51, wherein said at least one organic solvent is chosen from $C_1$–$C_4$ alkanols; glycerol; glycols and glycol ethers; and aromatic alcohols.

53. A composition according to claim 52, wherein said $C_1$–$C_4$ alkanols are chosen from ethanol and isopropanol.

54. A composition according to claim 52, wherein said glycols and glycol ethers are chosen from 2-butoxyethanol, propylene glycol, monomethyl ether of propylene glycol, monoethyl ether and monomethyl ether of diethylene glycol.

55. A composition according to claim 52, wherein said aromatic alcohols are chosen from benzyl alcohol and phenoxyethanol.

56. A composition according to claim 51, wherein said at least one organic solvent is present in an amount ranging from 1 to 40% by weight relative to the total weight of the dyeing composition.

57. A composition according to claim 56, wherein said at least one organic solvent is present in an amount ranging from 5 to 30% by weight relative to the total weight of the dyeing composition.

58. A composition according to claim 1, wherein said dyeing composition has a pH ranging from 3 to 12 and the pH is adjusted by at least one agent for adjusting pH.

59. A composition according to claim 58, wherein said dyeing composition has a pH ranging from 5 to 11.

60. A composition according to claim 58, wherein said at least one agent for adjusting pH is chosen from acidifying and alkalinizing agents.

61. A composition according to claim 60, wherein said acidifying agents are chosen from inorganic and organic acids.

62. A composition according to claim 61, wherein said inorganic and organic acids are chosen from hydrochloric, orthophosphoric, sulfuric, and carboxylic acids.

63. A composition according to claim 62, said carboxylic acids are chosen from acetic, tartaric, citric, lactic and sulfonic acids.

64. A composition according to claim 60, wherein said alkalinizing agents are chosen from aqueous ammonia, alkali metal carbonates, alkanolamines, sodium hydroxides, potassium hydroxides and compounds of formula (II):

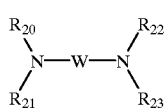

wherein W is a propylene residue, optionally substituted with a group chosen from a hydroxyl group and a $C_1$–$C_6$ alkyl group, $R_{20}$, $R_{21}$, $R_{22}$ and $R_{23}$, which are identical or different, are each chosen from a hydrogen atom, $C_1$–$C_6$ alkyl groups and $C_1$–$C_6$ hydroxyalkyl groups.

65. A composition according to claim 64, wherein said alkanolamines are chosen from mono-, di-, and triethanolamine, and derivatives thereof.

66. A composition according to claim 1, wherein said oxidation dyeing composition further comprises at least one direct dye.

67. A composition according to claim 1, wherein said oxidation dyeing composition further comprises at least one adjuvant used in hair dyeing compositions.

68. A composition according to claim 67, wherein said at least one adjuvant is chosen from anionic, cationic, nonionic, amphoteric and zwitterionic surfactants; anionic, cationic, nonionic, amphoteric and zwitterionic polymers, inorganic and organic thickeners, antioxidants, penetrating agents, sequestering agents, perfumes, buffers, dispersing agents, and conditioning agents.

69. A composition according to claim 68, wherein said conditioning agents are chosen from, modified and unmodified, volatile and nonvolatile silicones, film-forming agents, ceramides, preservatives, and opacifying agents.

70. A composition according to claim 1, wherein said unsaturated groups and said unsaturated $C_1$–$C_6$ alkyl groups are chosen from at least one double bond and at least one triple bond.

71. A composition according to claim 1, wherein said composition is a liquid, a cream, a gel, or any form suitable for dyeing keratinous fibers.

72. A composition according to claim 1, wherein said keratinous fibers are human hair.

73. A process for oxidation dyeing keratinous fibers comprising:

(1) applying to said fibers at least one dyeing composition comprising, in a medium suitable for dyeing:
    (a) at least one oxidation base; and
    (b) at least one coupler chosen from compounds of formula (I) and acid addition salts thereof:

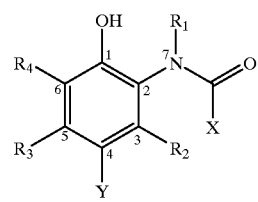

wherein:
$R_1$ is chosen from a hydrogen atom, linear and branched, saturated and unsaturated groups comprising from 1–15 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the provisos that:
  (i) said $R_1$ does not comprise a group chosen from a peroxide group, a diazo group, a nitro group, and a nitroso group, and
  (ii) said $SO_2$ group is not directly linked to the nitrogen at the 7-position of formula (I);
X is chosen from groups $OR_5$ and $NR_6R_7$, wherein
  $R_5$ is chosen from linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
    (i) said $R_5$ does not comprise a group chosen from a peroxide group, a diazo group, a nitro group, and a nitroso group;
  $R_6$ and $R_7$, which are identical or different, are each chosen from a hydrogen atom, linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
    (i) both said $R_6$ and $R_7$ do not comprise a group chosen from a peroxide group, a diazo group, a nitro group, and a nitroso group, and
  said $R_6$ and $R_7$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R, wherein
    R is chosen from linear, branched, saturated, and unsaturated, $C_1$–$C_6$ alkyl groups, optionally substituted with at least one halogen atom, wherein at least one carbon atom is optionally replaced by a unit chosen from an oxygen atom, a nitrogen atom, a sulfur atom, and a $SO_2$ group, and at least one branch of said branched $C_1$–$C_6$ alkyl group optionally forms at least one saturated or unsaturated 3- to 6-membered ring; with the proviso that:
(i) said R does not comprise a group chosen from a peroxide group, a diazo group, a nitro group, and a nitroso group;
wherein
said $R_1$ and said $R_5$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group; and
said $R_1$ and said $R_6$ optionally form a ring, chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;
$R_2$, $R_3$ and $R_4$, which are identical or different, are each chosen from a hydrogen atom, a halogen atom, and linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally form at least one 3- to 7-membered ring comprising at least one carbon atom, with the provisos that:
(i) said $R_2$, $R_3$ and $R_4$ do not comprise a group chosen from a peroxide group, a diazo group, a nitro group, and a nitroso group;
(ii) said $R_4$ is chosen from a group other than a hydroxyl group, a thio group, an amino group, and a substituted or unsubstituted sulphonylamino group; and
(iii) said $R_2$, $R_3$ and $R_4$ are not directly linked to the benzene ring of formula (I) by a —NH—NH—;
wherein
said $R_1$ and said $R_2$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;
wherein
said $R_2$ and said $R_5$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_5$ form a saturated ring comprising 5- to 7-members, said $R_5$ optionally is a bond;
wherein
said $R_2$ and said $R_6$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_6$ form a saturated ring comprising 5- to 7-members, said $R_6$ optionally is a bond;
Y is chosen from:
a hydrogen atom;
a halogen atom;
a group chosen from —$OR_8$, —$SR_8$, and —NH—$SO_2R_8$, wherein
$R_8$ is chosen from:
linear and branched $C_1$–$C_8$ alkyl groups, optionally substituted with at least one group chosen from a halogen atom, a hydroxyl group, $C_1$–$C_4$ alkoxy groups, an amino group, amino($C_1$–$C_4$ alkyl) groups, a carboxyl group, and $C_1$–$C_4$ alkoxycarbonyl groups, wherein at least one branch of said branched $C_1$–$C_8$ alkyl groups optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
a benzyl group, optionally substituted with one or two oxy groups, with the proviso that:
(i) when $R_2$ is a hydroxyl group, Y is not a —NH—$SO_2R_8$ group;
provided that:
(i) when said $R_2$ and said $R_4$ are hydrogen atoms, and when said $R_3$ is chosen from substituted and unsubstituted $C_1$–$C_4$ alkyl groups, X is not a an —$OR_5$ group, wherein $R_5$ is chosen from substituted and unsubstituted $C_1$–$C_4$ alkyl groups;
(ii) when said $R_2$ and said $R_4$ are hydrogen atoms, and when said $R_3$ is chosen from substituted and unsubstituted $C_1$–$C_4$ alkyl groups, X is not a $NR_6R_7$ group; and
(iii) when said $R_2$, said $R_4$, and said Y, are hydrogen atoms, and when said X is a $NR_6R_7$ group, wherein said $R_6$ and $R_7$ are hydrogen atoms, said $R_3$ is not chosen from a fluorine atom, a chlorine atom and a bromine atom; and
(2) developing a color with at least one oxidizing agent, wherein said oxidizing agent is combined at the time of use with said at least one dyeing compostion or said at least one oxidizing agent is applied simultaneously or sequentially to said at least one dyeing composition.

74. A process according to claim 73, wherein said at least one oxidizing agent is chosen from hydrogen peroxide, urea peroxide, alkali metal bromates, persalts, peracids, and enzymes.

75. A process according to claim 74, wherein said enzymes are chosen from peroxidases, laccases, tyrosinases and oxidoreductases.

76. A process for oxidation dyeing keratinous fibers comprising:
(1) applying to said fibers at least one dyeing composition comprising, in a medium suitable for dyeing:
    (a) at least one oxidation base; and
    (b) at least one coupler chosen from compounds of formula (I) and acid addition salts thereof:

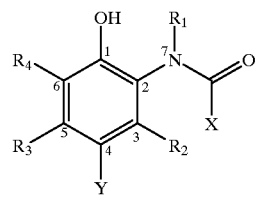

(I)

in which:
R$_1$ is chosen from a hydrogen atom, linear and branched, saturated and unsaturated groups comprising from 1–15 carbon atoms, optionally substituted with at least one halogen atom, wherein at least one carbon atom is optionally replaced by a unit chosen from an oxygen atom, a nitrogen atom, a sulfur atom, and a SO$_2$ group, and at least one branch of said branched groups optionally forms at least one 3- to 7-membered ring comprising at least one carbon atom, with the provisos that:
    (i) said R$_1$ does not comprise a group chosen from a peroxide group, a diazo group, a nitro group, and a nitroso group, and
    (ii) said SO$_2$ group is not directly linked to the nitrogen at the 7-position of formula (I);
X is chosen from groups OR$_5$ and NR$_6$R$_7$, wherein
    R$_5$ is chosen from linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a SO$_2$ group, and at least one branch of said branched groups optionally forms at least one 3- to 7-membered ring comprising at least one carbon atom, with the proviso that:
        (i) said R$_5$ does not comprise a group chosen from a peroxide group, a diazo group, a nitro group, and a nitroso group;
    R$_6$ and R$_7$, which are identical or different, are each chosen from a hydrogen atom, linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a SO$_2$ group, and at least one branch of said branched groups optionally forms at least one 3- to 7-membered ring comprising at least one carbon atom, with the proviso that:
        (i) both said R$_6$ and R$_7$ do not comprise a group chosen from a peroxide group, a diazo group, a nitro group, and a nitroso group, and
    said R$_6$ and R$_7$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R, wherein
        R is chosen from linear, branched, saturated, and unsaturated, C$_1$–C$_6$ alkyl groups, optionally substituted with at least one halogen atom, wherein at least one carbon atom is optionally replaced by a unit chosen from an oxygen atom, a nitrogen atom, a sulfur atom, and a SO$_2$ group, and at least one branch of said branched C$_1$–C$_6$ alkyl group optionally forms at least one saturated or unsaturated 3- to 6-membered ring; with the proviso that:
            (i) said R does not comprise a group chosen from a peroxide group, a diazo group, a nitro group, and a nitroso group;
wherein
    said R$_1$ and said R$_5$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
        (i) said R does not comprise a group chosen from a peroxide group, a diazo group, a nitro group, and a nitroso group; and
    said R$_1$ and said R$_6$ optionally form a ring, chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
        (i) said R does not comprise a group chosen from a peroxide group, a diazo group, a nitro group, and a nitroso group;
R$_2$, R$_3$, and R$_4$, which are identical or different, are each chosen from a hydrogen atom, a halogen atom, and linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a SO$_2$ group, and at least one branch of said branched groups optionally form at least one 3- to 7-membered ring comprising at least one carbon atom, with the provisos that:
    (i) said R$_2$, R$_3$ and R$_4$ do not comprise a group chosen from a peroxide group, a diazo group, a nitro group, and a nitroso group;
    (ii) said R$_4$ is chosen from a group other than a hydroxyl group, a thio group, an amino group, and a substituted or unsubstituted sulphonylamino group; and
    (iii) said R$_2$, R$_3$ and R$_4$ are not directly linked to the benzene ring of formula (I) by a —NH—NH—;
wherein
    said R$_1$ and said R$_2$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
        (i) said R does not comprise a group chosen from a peroxide group, a diazo group, a nitro group, and a nitroso group;

wherein
said $R_2$ and said $R_5$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_5$ form a saturated ring comprising 5- to 7-members, said $R_5$ optionally is a bond;
wherein
said $R_2$ and said $R_6$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_6$ form a saturated ring comprising 5- to 7-members, said $R_6$ optionally is a bond;
Y is chosen from:
a hydrogen atom;
a halogen atom;
a group chosen from —$OR_8$, —$SR_8$, and —NH—$SO_2R_8$, wherein
$R_8$ is chosen from:
linear and branched $C_1$–$C_8$ alkyl groups, optionally substituted with at least one group chosen from a halogen atom, a hydroxyl group, $C_1$–$C_4$ alkoxy groups, an amino group, amino($C_1$–$C_4$ alkyl) groups, a carboxyl group, and $C_1$–$C_4$ alkoxycarbonyl groups, wherein at least one branch of said branched $C_1$–$C_8$ alkyl group optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
a benzyl group, optionally substituted with one or two oxy groups, with the proviso that:
(i) when $R_2$ is a hydroxyl group, Y is not a —NH—$SO_2R_8$ group;
provided that:
(i) when said $R_2$ and said $R_4$ are hydrogen atoms, and when said $R_3$ is chosen from substituted and unsubstituted $C_1$–$C_4$ alkyl groups, X is not a an —$OR_5$ group, wherein $R_5$ is chosen from substituted and unsubstituted $C_1$–$C_4$ alkyl groups;
(ii) when said $R_2$ and said $R_4$ are hydrogen atoms, and when said $R_3$ is a substituted or unsubstituted $C_1$–$C_4$ alkyl group, X is not a $NR_6R_7$ group; and
(iii) when said $R_2$, said $R_4$, and said Y, are hydrogen atoms, and when said X is a $NR_6R_7$ group, wherein said $R_6$ and $R_7$ are hydrogen atoms, said $R_3$ is not chosen from a fluorine atom, chlorine atom and a bromine atom; and (2) developing a color with at least one oxidizing composition comprising, in a medium suitable for dyeing, at least one oxidizing agent present in an amount sufficient to develop a color, wherein said at least one oxidizing composition is combined at the time of use with said at least one dyeing composition,
(3) leaving said combination to act for a time ranging from 3 to 50 minutes, and
(4) rinsing said keratinous fibers, shampooing said keratinous fibers after said shampooing, and drying said keratinous fibers.
77. A process according to claim 76, wherein said at least one oxidizing agent is chosen from hydrogen peroxide, urea peroxide, alkali metal bromates, persalts, peracids, and enzymes.
78. A process according to claim 77, wherein said enzymes are chosen from peroxidases, laccases, tyrosinases and oxidoreductases.
79. A kit comprising two compartments, wherein:
a) a first compartment comprises at least one oxidizing composition; and
b) a second compartment comprises at least one dyeing composition comprising, in a medium suitable for dyeing:
i) at least one oxidation base, and
ii) at least one coupler chosen from compounds of formula (I), and acid addition salts thereof:

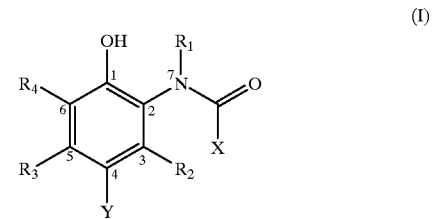

(I)

in which:
$R_1$ is chosen from a hydrogen atom, linear and branched, saturated and unsaturated groups comprising from 1–15 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the provisos that:
(i) said $R_1$ does not comprise a group chosen from a peroxide group, a diazo group, a nitro group, and a nitroso group, and
(ii) said $SO_2$ group is not directly linked to the nitrogen at the 7-position of formula (I);
X is chosen from groups $OR_5$ and $NR_6R_7$, wherein
$R_5$ is chosen from linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) said $R_5$ does not comprise a group chosen from a peroxide group, a diazo group, a nitro group, and a nitroso group;

$R_6$ and $R_7$, which are identical or different, are each chosen from a hydrogen atom, linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally forms at least one 3- to 7-membered ring comprising at least one carbon atom, with the proviso that:
(i) both said $R_6$ and $R_7$ do not comprise a group chosen from a peroxide group, a diazo group, a nitro group, and a nitroso group, and said $R_6$ and $R_7$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R, wherein
R is chosen from linear, branched, saturated, and unsaturated, $C_1$–$C_6$ alkyl groups, optionally substituted with at least one halogen atom, wherein at least one carbon atom is optionally replaced by a unit chosen from an oxygen atom, a nitrogen atom, a sulfur atom, and a $SO_2$ group, and at least one branch of said branched $C_1$–$C_6$ alkyl group optionally forms at least one saturated or unsaturated 3- to 6-membered ring; with the proviso that:
(i) said R does not comprise a group chosen from a peroxide group, a diazo group, a nitro group, and a nitroso group;

wherein
said $R_1$ and said $R_5$ optionally form a ring chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group; and said $R_1$ and said $R_6$ optionally form a ring, chosen from a saturated and an unsaturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

$R_2$, $R_3$, and $R_4$, which are identical or different, are each chosen from a hydrogen atom, a halogen atom, and linear and branched, saturated and unsaturated groups comprising from 1–20 carbon atoms, optionally substituted with at least one halogen atom, wherein at least one carbon atom is optionally replaced by a unit chosen from an oxygen atom, a nitrogen atom, a sulfur atom, and a $SO_2$ group, and at least one branch of said branched groups optionally form at least one 3- to 7-membered ring comprising at least one carbon atom, with the provisos that:
(i) said $R_2$, $R_3$ $R_4$ do not comprise a group chosen from a peroxide group, a diazo group, a nitro group, and a nitroso group;

(ii) said $R_4$ is chosen from a group other than a hydroxyl group, a thio group, an amino group, and a substituted or unsubstituted sulphonylamino group; and
(iii) said $R_2$, $R_3$ and $R_4$ are not directly linked to the benzene ring of formula (I) by a —NH—NH—;

wherein
said $R_1$ and said $R_2$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the proviso that:
(i) said R does not comprise a group chosen from a peroxide group, a diazo group, a nitro group, and a nitroso group;

wherein
said $R_2$ and said $R_5$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_5$ form a saturated ring comprising 5- to 7-members, said $R_5$ optionally is a bond;

wherein
said $R_2$ and said $R_6$ optionally form a saturated ring comprising 5- to 7-members, wherein said members are each chosen from a carbon atom, a nitrogen atom, an oxygen atom, a sulfur atom, and a carbonyl group, and said members are optionally substituted with 1 or 2 groups R as defined above, with the provisos that:
(i) said R does not comprise a group chosen from a peroxide group, a diazo group, a nitro group, and a nitroso group; and
(ii) when said $R_2$ and said $R_6$ form a saturated ring comprising 5- to 7-members, said $R_6$ optionally is a bond;

Y is chosen from:
a hydrogen atom;
a halogen atom;
a group chosen from —$OR_8$, —$SR_8$, and —NH—$SO_2R_8$, wherein
$R_8$ is chosen from:
linear and branched $C_1$–$C_8$ alkyl groups, optionally substituted with at least one group chosen from a halogen atom, a hydroxyl group, $C_1$–$C_4$ alkoxy groups, an amino group, amino($C_1$–$C_4$ alkyl) groups, a carboxyl group, and $C_1$–$C_4$ alkoxycarbonyl groups, wherein at least one branch of said branched $C_1$–$C_8$ alkyl group optionally forms at least one 3- to 6-membered ring;
a phenyl group, optionally substituted with one or two groups chosen from $C_1$–$C_4$ alkyl groups, a trifluoromethyl group, a carboxyl group, $C_1$–$C_4$ alkoxycarbonyl groups, a halogen atom, a hydroxyl group, $C_1$–$C_4$ alkoxy groups, an amino group and amino($C_1$–$C_4$ alkyl) groups; and
a benzyl group, optionally substituted with one or two oxy groups, with the proviso that:
(i) when $R_2$ is a hydroxyl group, Y is not a —NH—$SO_2R_8$ group;

provided that:
- (i) when said $R_2$ and said $R_4$ are hydrogen atoms, and when said $R_3$ is chosen from substituted and unsubstituted $C_1$–$C_4$ alkyl groups, X is not a an —$OR_5$ group, wherein $R_5$ is chosen from substituted and unsubstituted $C_1$–$C_4$ alkyl groups;
- (ii) when said $R_2$ and said $R_4$ are hydrogen atoms, and when said $R_3$ is a substituted or unsubstituted $C_1$–$C_4$ alkyl group, X is not a $NR_6R_7$ group; and
- (iii) when said $R_2$, said $R_4$ and said Y, are hydrogen atoms, and when said X is a $NR_6R_7$ group, wherein said $R_6$ and $R_7$ are hydrogen atoms, said $R_3$ is not chosen from a fluorine atom, chlorine atom and a bromine atom.

80. A process according to claim 73, wherein said unsaturated groups and said unsaturated $C_1$–$C_6$ alkyl groups are chosen from at least one double bond and at least one triple bond.

81. A process according to claim 76, wherein said unsaturated groups and said unsaturated $C_1$–$C_6$ alkyl groups are chosen from at least one double bond and at least one triple bond.

82. A kit according to claim 79, wherein said unsaturated groups and said unsaturated $C_1$–$C_6$ alkyl groups are chosen from at least one double bond and at least one triple bond.

* * * * *

UNITED STATES PATENT AND TRADEMARK OFFICE
CERTIFICATE OF CORRECTION

PATENT NO. : 6,635,091 B2
DATED : October 21, 2003
INVENTOR(S) : Jean-Baptiste Saunier et al.

It is certified that error appears in the above-identified patent and that said Letters Patent is hereby corrected as shown below:

Title Page,
Item [73], Assignee, "S. A.," should read -- S.A., --.

Column 29,
Line 50, "not a an -$OR_5$ group," should read -- not an -$OR_5$ group, --.

Column 31,
Line 51, "$C_1$-$C_6$ a alkyl groups," should read -- $C_1$-$C_6$ alkyl groups, --.

Column 33,
Line 36, "not a an -$OR_5$ group," should read -- not an -$OR_5$ group, --.

Column 37,
Line 36, "not a an -$OR_5$ group," should read -- not an -$OR_5$ group, --.

Column 38,
Line 55, after "N-($C_1$-$C_3$)alkyl-N-($C_1$-$C_3$)alkylamino", insert a comma.

Column 41,
Line 17, "not a an -$OR_5$ group," should read -- not an -$OR_5$ group, --.
Line 53, "from a ring," should read -- form a ring, --.
Line 60, "from a ring," should read -- form a ring, --.

Column 45,
Line 60, "not a an -$OR_5$ group," should read -- not an -$OR_5$ group, --.

Column 50,
Line 1, "not a an -$OR_5$ group," should read -- not an -$OR_5$ group, --.

Column 53,
Line 15, "not a an -$OR_5$ group," should read -- not an -$OR_5$ group, --.

Column 57,
Line 39, "not a an -$OR_5$ group," should read -- not an -$OR_5$ group, --.

Column 60,
Line 57, "not a an -$OR_5$ group," should read -- not an -$OR_5$ group, --.

UNITED STATES PATENT AND TRADEMARK OFFICE
CERTIFICATE OF CORRECTION

PATENT NO. : 6,635,091 B2
DATED : October 21, 2003
INVENTOR(S) : Jean-Baptiste Saunier et al.

It is certified that error appears in the above-identified patent and that said Letters Patent is hereby corrected as shown below:

Column 63,
Line 8, "hydroxyl gruop," should read -- hydroxyl group, --.

Column 64,
Line 60, "not a an -$OR_5$ group," should read -- not an -$OR_5$ group, --.

Column 68,
Line 62, "not a an -$OR_5$ group," should read -- not an -$OR_5$ group, --.

Column 72,
Line 4, "not a an -$OR_5$ group," should read -- not an -$OR_5$ group, --.
Line 15, after "according", insert -- to --.
Line 25, after "according", insert -- to --.

Column 76,
Line 48, "3-(2-Hydroxy-4-amino-5-chlorophenyl)1-methylurea," should read
-- 3-(2-Hydroxy-4-amino-5-chlorophenyl)-1-methylurea, --.
Line 49, "3-(2-Hydroxy-4-amino-5-chlorophenyl)1-ethylurea," should read
-- 3-(2-Hydroxy-4-amino-5-chlorophenyl)-1-ethylurea, --.

Column 77,
Lines 52-53, "3-(2-Hydroxy-4-amino-5-methoxyphenyl) 1-(2-hydroxyethyl)urea," should read -- 3-(2-Hydroxy-4-amino-5-methoxyphenyl)-1-(2-hydroxyethyl)urea, --.

Column 78,
Lines 1-2, "3-(2-Hydroxy-4-methylamino-5-methoxyphenyl)1-ethylurea," should read -- 3-(2-Hydroxy-4-methylamino-5-methoxyphenyl)-1-ethylurea, --.
Line 51, "3-(2-Hydroxy-3-(3-ethylureido)phenyl)1-ethylurea," should read
-- 3-(2-Hydroxy-3-(3-ethylureido)phenyl)-1-ethylurea, --.
Lines 54-55, "3-(2-Hydroxy-3-(3-isopropylureido)phenyl)1-isopropylurea," should read -- 3-(2-Hydroxy-3-(3-isopropylureido)phenyl)-1-isopropylurea, --.

Column 79,
Line 34, after "1-(2-Hydroxy-4-(2-hydroxyethyl)aminophenyl)urea", insert a comma.

Column 80,
Line 58, "1-(2-Hydroxy-4-methylamino-5-,methoxyphenyl)urea" should read
-- 1-(2-Hydroxy-4-methylamino-5-methoxyphenyl)urea, --.

UNITED STATES PATENT AND TRADEMARK OFFICE
CERTIFICATE OF CORRECTION

PATENT NO. : 6,635,091 B2
DATED : October 21, 2003
INVENTOR(S) : Jean-Baptiste Saunier et al.

It is certified that error appears in the above-identified patent and that said Letters Patent is hereby corrected as shown below:

Column 81,
Line 35, after "1-(2-Hydroxy-4-aminophenyl)urea", insert a comma.

Column 82,
Lines 26-27, "4-N, N-bis(β-hydroxyethyl)amino-2-methylaniline," should read
-- 4-N,N-bis(β-hydroxyethyl)amino-2-methylaniline, --.
Line 41, after "claim 34,", insert -- wherein --.

Column 83,
Lines 32-33, "2-[(3-aminopyrazolo[1,5-a]pyrimidin-7-yl)-(2-hydroxy-ethyl)aminono] ethanol," should read -- 2-[(3-aminopyrazolo[1,5-a]pyrimidin-7-yl)-(2-hydroxy-ethyl) amino]ethanol, --.

Column 88,
Line 47, "not a an $-OR_5$ group," should read -- not an $-OR_5$ group, --.

Column 91,
Line 57, "not a an $-OR_5$ group," should read -- not an $-OR_5$ group, --.

Column 93,
Line 44, "R, and said $R_6$" should read -- $R_1$ and said $R_6$ --.
Line 65, "$R_2$, $R_3$ $R_4$" should read -- $R_2$, $R_3$ and $R_4$ --.

Column 95,
Line 4, "not a an $-OR_5$ group," should read -- not an $-OR_5$ group, --.

Signed and Sealed this

Twenty-third Day of December, 2003

JAMES E. ROGAN
*Director of the United States Patent and Trademark Office*